(12) United States Patent
Hlatky

(10) Patent No.: US 8,679,835 B2
(45) Date of Patent: Mar. 25, 2014

(54) TUMOR-INITIATING CELLS AND METHODS OF USE

(75) Inventor: Lynn Hlatky, Boston, MA (US)

(73) Assignee: GeneSys Research Institute, Brighton, MA (US)

( * ) Notice: Subject to any disclaimer, the term of this patent is extended or adjusted under 35 U.S.C. 154(b) by 0 days.

(21) Appl. No.: 12/495,417

(22) Filed: Jun. 30, 2009

(65) Prior Publication Data
US 2010/0162419 A1  Jun. 24, 2010

Related U.S. Application Data

(60) Provisional application No. 61/133,497, filed on Jun. 30, 2008.

(51) Int. Cl.
*A01K 67/00* (2006.01)
*C12N 5/12* (2006.01)
*C12N 5/02* (2006.01)
*C12Q 1/02* (2006.01)
*A61K 39/00* (2006.01)

(52) U.S. Cl.
USPC ............ 435/346; 435/325; 435/378; 435/29; 435/377; 424/277.1

(58) Field of Classification Search
None
See application file for complete search history.

(56) References Cited

U.S. PATENT DOCUMENTS

2002/0102230 A1   8/2002   Wang et al.
2004/0142333 A1   7/2004   Lu et al.

OTHER PUBLICATIONS

Chakraborty (Cancer Research. 2000; 60:2512-2519).*
Kirsten Walen (In Vitro Cell. Dev. Biol.-Animal; Jun. 2004; 40: 150-158).*
Fridman et al. (Oncogene. 2003; 22: 9030-9040).*
Chen et al. (Experimental Neurology. 2006; 198: 129-135).*
International Search Report dated Nov. 25, 2009, corresponding to related application PCT/US09/03924.
Duelli et al., "Cell Fusion: A hidden enemy?" Cancer Cell, May 2003, vol. 3, pp. 445-448.
Terada et al., "Bone marrow cells adopt the phenotype of other cells by spontaneous cell fusion", Nature, vol. 416, Apr. 4, 2002, pp. 542-545.

* cited by examiner

*Primary Examiner* — Scott Long
(74) *Attorney, Agent, or Firm* — Edwards Wildman Palmer LLP; David G. Conlin; Richard B. Emmons

(57) ABSTRACT

Provided herein are an isolated or enriched population of tumor initiating cells derived from normal cells, cells susceptible to neoplasia, or neoplastic cells. Methods of use of the cells for screening for anti-hyperproliferative agents, and use of the cells for animal models of hyperproliferative disorders including metastatic cancer, diagnostic methods, and therapeutic methods are provided.

51 Claims, 20 Drawing Sheets

SEQUENCE LISTING

<160> NUMBER OF SEQ ID NOS: 1

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
cgtcacccgt cgacactcct gggtgacccc cacgtggtct tgtggcggcg tctgacggga    60
cg                                                                  62

TUMOR-INITIATING CELLS AND METHODS OF USE

CROSS-REFERENCE TO RELATED APPLICATION

This application claims the benefit of U.S. Provisional Application No. 61/133,497, filed on Jun. 30, 2008, the entire contents of which are incorporated herein by reference.

STATEMENT OF RIGHTS TO INVENTIONS MADE UNDER FEDERALLY SPONSORED RESEARCH

The work was supported by in part, by NASA grant NNJ06HA28G. The Government has certain rights in the invention.

BACKGROUND OF THE INVENTION

Thirty years of investigations into the molecular genetics and signaling of cancer cells have revealed cancer to be a genetic disease. The prevailing carcinogenesis paradigm asserts that cancer originates from a single cell which, through a series of well-defined mutations and selected clonal expansions, ultimately transforms into a cancer cell. Intense study has identified three critical gene classes which contribute to the carcinogenesis process: oncogenes, tumor-suppressor genes and DNA repair genes, sometimes referred to as stability genes. Beyond the abnormal regulation of these classic cancer genes, a number of additional processes which are common across cancer types have been identified as hallmarks of the disease. These include sustained angiogenesis, tissue invasion and metastasis, and unlimited replicative capacity. Cancer cells also exhibit genomic instability, where the progeny of cancer cells express increasing levels of chromosomal aberrations and allelic imbalance. Genomic instability generates the vast genotypic and phenotypic diversity found in all tumors, and it is the major obstacle in cancer treatment.

Despite these major inroads into elucidating the carcinogenesis process, there still remain large gaps in scientists' understanding of how mutations actually drive cell transformation and the subsequent cancer progression. Although gene mutations clearly contribute to cancer, no single mutated gene or combination of mutated genes occur in all or even in the majority of cancers. Moreover, it is not gene mutations, but primarily chromosome-level aberrations that occur in cells following transformation to the cancer state. Although it has long been assumed that cancers arise from mutated differentiated cells, there is now considerable interest in determining if instead it is mutated stem cells that are at the origin of cancer. Stem cells and cancer cells exhibit common properties such as the ability to continuously self-renew and differentiate. Although genomic instability is ubiquitous across cancers, the mechanisms that drive this instability are still undetermined. Inhibition of DNA repair or stability genes, alterations in mitosis genes, aberrant centromeres, aneuploidy, teleomere dysregulations and, for virus-linked cancers, virus-induced fusion of genetically-mutated cells, have all been suggested as causes of the instability. Finally, given that gene mutations and particularly chromosome aberrations decrease the fitness of a cell, it is not understood how cancer cell populations are able to sustain and proliferate in the face of the high degree of chromosomal damage per cell.

Although conventional treatments for neoplasia typically reduce the size of tumors, such responses can be transient. Many cancers will eventually recur, and these recurrences can be fatal. This observation has given rise to the hypothesis that cancer may originate in a small population of cancer stem cells that are responsible for the growth of tumors and that are resistant to conventional cancer therapies. Cancer stem cells are believed to be quite rare, and have been difficult to isolate. Methods for generating cells that are capable of initiating tumors and isolated populations of such cells are required for the identification of novel anti-neoplastic agents that are useful not only as chemotherapeutics, but that can prevent cancer relapse by targeting tumor-initiating cells that are capable of regenerating a tumor when anti-cancer therapy is completed.

SUMMARY OF THE INVENTION

The invention provides tumor-initiating cell compositions, methods for producing a tumor-initiating cell, the use of such cells for the identification of agents useful for the treatment or prevention of neoplasia and neoplasia relapse following chemotherapy or radiation therapy, as well as anti-neoplasia vaccines, and for the treatment of diseases and disorders associated with a deficiency in cell number.

The invention provides an isolated cell selected for having undergone at least one spontaneous cell-cell fusion, or a descendant of said cell, wherein said cell is self-renewing. Such cells can be used for the methods taught herein.

The invention further provides a tumor-initiating cell selected as having undergone spontaneous cell-cell fusion or a descendant of said cell. Tumor-initiating cells of the invention give rise to a neoplasia in vitro or in vivo under suitable growth conditions. Further, the tumor initiating cells of the invention exhibit one or more characteristic features as demonstrated herein. These characteristics include, but are not limited to, aneuploidy, increased cellular proliferation rate relative to a corresponding reference cell, periodically increased expression of VEGF, k-ras, myc, MMP-9, CD44 or Bcl-2 relative to a corresponding reference cell, periodically reduced expression of CDKn2A and p53 relative to a corresponding reference cell, formation of a colony in soft agar in vitro, and formation of a tumor in vivo.

The tumor initiating cells of the invention can be generated by the spontaneous fusion between a neoplastic cell and a neoplastic cell, a non-neoplastic cell and a neoplastic cell, or a non-neoplastic cell and a non-neoplastic cell. Cells for fusion can be obtained from essentially any source including, but not limited to immortalized cell lines, normal cells from a subject for example a subject identified as being prone to or having neoplasia. Normal or neoplastic cells can be obtained from a subject being prone to or having neoplasia. Cells for use in the invention can be any type of cell that does not normally undergo spontaneous cell fusion in the absence of disease, for example, a fibroblast or epithelial cell. Cells that undergo spontaneous fusion in the absence of disease include muscle cells, macrophages, and gametes in the formation of a zygote. The fused cells of the invention do not include cells that have undergone chemically induced fusion, as in the case of hybridomas, or virally induced fusion.

The invention also provides an isolated cell population of cells selected for having undergone at least one spontaneous cell-cell fusion or a descendant of such a cell. The cells are cultured under conditions sufficient to promote further fusion, wherein at least one cell of said population is a self-renewing tumor-initiating cell. For example, the cells are cultured at a relatively high density. In an embodiment, at least about 50-75% of the cell population are tumor-initiating cells or highly tumorogenic cells. In some embodiments at least, 80%, 85%, 90%, or 95% of the cells are tumor initiating cells or highly tumorigenic cells. Further, the tumor initiating cells in the population exhibit one or more characteristic features as demonstrated herein. These characteristics include, but are not limited to, aneuploidy, increased cellular proliferation rate relative to a corresponding reference cell, periodically increased expression of VEGF, k-ras, myc, MMP-9, CD44 or Bcl-2 relative to a corresponding reference cell, periodically reduced expression of CDKn2A and p53 relative to a corresponding reference cell, formation of a colony in soft agar in vitro, and formation of a tumor in vivo. In an embodiment, at least about 50% of the cells are aneuploid and show increased expression of an oncogene selected from the group consisting of k-ras, myc and Bcl-2, and show decreased expression of CDKn2A and p53 relative to a corresponding reference cell. In an embodiment, the expression of genes associated with hyperproliferation and neoplasia are synchronously differentially expressed within the population. Synchronously and differentially expressed markers include, but are not limited to, Myc, K-ras, Bcl-2, p53, CDKn2a, CD44, SPP1, and VEGF relative to a corresponding reference population. In an embodiment, at least 50%, 60%, 70%, 80%, or 90% of the cells synchronously differentially express at least 2, 3, 4, 5, 6, 7, or 8 of the markers.

The population of tumor initiating cells provided by the invention are highly tumorigenic. For example, the population of cells enriched for having undergone cell fusion has a tumor producing efficiency that is at least about 10-fold greater than a reference cell. Highly tumorigenic cells can also be identified by their ability to consistently form tumors from a small number of injected cells in a short period of time. For example, the populations of cells enriched for cells that have undergone fusion, can form tumors upon injection of at least about 10-500 cells of the population forms a tumor of about 1 cm diameter in at least about 50% of nude mice within about 2-6 weeks. The populations of cells enriched for cells that have undergone fusion can also form tumors in immune competent mice.

The population of tumor initiating cells of the invention can be generated by the spontaneous fusion between a neoplastic cell and a neoplastic cell, a non-neoplastic cell and a neoplastic cell, or a non-neoplastic cell and a non-neoplastic cell. Cells for fusion can be obtained from essentially any source including, but not limited to immortalized cell lines, normal cells from a subject for example a subject identified as being prone to or having neoplasia. Normal or neoplastic cells can be obtained from a subject being prone to or having neoplasia. Cells for use in the invention can be any type of cell that does not normally undergo spontaneous cell fusion in the absence of disease, for example, a fibroblast or epithelial cell. Cells that undergo spontaneous fusion in the absence of disease include muscle cells, macrophages, and gametes in the formation of a zygote. The fused cells of the invention do not include cells that have undergone chemically induced fusion, as in the case of hybridomas, or virally induced fusion.

The invention provides a method for the generation of highly tumorigenic cells in culture enriched for cells that have undergone fusion and culturing the cells at a relatively high density to allow the cells to further undergo spontaneous fusion to produce multinucleate cells, and subsequently partition off mononuclear cells from the multinucleate cell. In an embodiment, the isolated population of cells selected for having undergone at least one spontaneous cell-cell fusion, or a descendant of such a cell, are preferably conditions sufficient to promote further fusion include culturing the cells at a density of about 80%, 85% or 90% confluence. In a preferred embodiment, the cells are cultured under standard growth conditions for the specific cell line (e.g., tissue culture media, growth factors, antibiotics). In a preferred embodiment, the cells are grown in the absence of agents that promote cell fusion (e.g., chemical agents, viruses) and are not transformed with oncogenes or other agents that can promote aneuploidy (e.g., mitogens, DNA damaging agents).

Cells that have undergone fusion can be identified by any method. In an embodiment, cells having undergone fusion are identified by the use of vital dyes such as cytoplasmic vital dyes or membrane vital dyes. In an alternate embodiment, the cells having undergone fusion are identified by direct observation of cells that have more than one nucleus and the nuclei are not the result of a single cell division, i.e., the cell is not in G2 or M. Cells containing three or more nuclei, e.g., 3, 4, 5, 6, 7, 8, 9, 10, or more nuclei, can be identified as having undergone fusion. Cells can be selected by automated methods, for example using fluorescence activated cell sorting. In an embodiment, the cells can be selected manually.

The invention provides cells made by the methods of the invention. Cells made by the methods of the invention have one or more of the following characteristics. They are self-renewing, are capable of forming tumors in immune competent and immune incompetent mice, and are resistant to exposure to radiation and/or chemotherapeutic agents. Further, the cells made by the methods of the invention exhibit one or more characteristic features as demonstrated herein. These characteristics include, but are not limited to, aneuploidy, increased cellular proliferation rate relative to a corresponding reference cell, periodically increased expression of VEGF, k-ras, myc, MMP-9, CD44 or Bcl-2 relative to a corresponding reference cell, periodically reduced expression of CDKn2A and p53 relative to a corresponding reference cell, formation of a colony in soft agar in vitro, and formation of a tumor in vivo. In an embodiment, at least about 50% of the cells are aneuploid and show increased expression of an oncogene selected from the group consisting of k-ras, myc and Bcl-2, and show decreased expression of CDKn2A and p53 relative to a corresponding reference cell. In an embodiment, the expression of genes associated with hyperproliferation and neoplasia are synchronously differentially expressed within the population. Synchronously and differentially expressed markers include, but are not limited to, Myc, K-ras, Bcl-2, p53, CDKn2a, CD44, SPP1, and VEGF relative to a corresponding reference population. In an embodiment, at least 50%, 60%, 70%, 80%, or 90% of the cells synchronously differentially express at least 2, 3, 4, 5, 6, 7, or 8 of the markers.

The invention further provides compositions including a population of tumor initiating cells made by the methods of the invention. In a preferred embodiment, the population is an isolated and/or enriched population of tumor initiating cells.

The invention further provides methods of use of the cells of the invention. In embodiment, the invention provides a method for identifying an agent for the treatment or prevention of a neoplasia, hyperplasia or a hyperproliferative disorder using the cells of the invention. The method includes contacting a tumor-initiating cell or cell population with an agent; and detecting a decrease in cell fusion, survival, and/or proliferation relative to an untreated control cell or cell population.

The invention further provides a method for the identification of anti-neoplastic agents by identifying agents that inhibit cell fusion. The method includes contacting a population of cells cultured under conditions sufficient to induce spontaneous cell-cell fusion with an agent; and detecting a reduction in cell-cell fusion relative to an untreated control population. In the method, a reduction in multinucleate cell number in the treated population identifies an agent that inhibits cell-cell fusion. For example, the agent may increase cell death.

The invention further provides methods for the identification of agents that inhibit the partitioning of cells containing single nuclei from the multinucleate cell. The method includes maintaining the multinucleate cell in culture under conditions sufficient to generate mononucleate cells from a multinucleate cell, and identifying agents that result in a reduction in the generation of said cells relative to a corresponding control culture.

The invention also provides methods for selecting a therapeutic regimen for a subject, including generating a population of cells enriched for cells having undergone cell fusion from a subject having a neoplastic disease and culturing them under the methods of the invention to generate a population of tumor initiating cells, contacting the cell population with one or more agents, such as chemotherapeutic agents, and detecting a decrease in cell survival, proliferation, or cell-cell fusion relative to an untreated control cell or cell population; and identifying the agent as effective in a therapeutic regimen for said subject. The method can be used for identifying initial therapeutic agents, monitoring for continued response of the neoplasia to therapeutic agents, or identifying agents useful in the treatment of a relapse. In an embodiment, the cells are derived from normal cells of the subject. In an embodiment, the cells are derived from the neoplasia of the subject. In an embodiment, the cells are a combination of normal and neoplastic cells from the subject.

The method further provides immunogenic compositions for the treatment or prevention of a neoplasia in a subject using non-viable cells of the invention in an excipient for administration to a subject. In an embodiment, the composition further includes an adjuvant. In an embodiment, the cells are derived from the subject to whom the immunogenic composition is to be administered. In an embodiment, the cells are derived from a subject other than the individual to whom the immunogenic composition is to be administered. In an embodiment, the subject has or is prone to neoplasia. The method can be used for inducing an immune response in a subject against a neoplasia for the prevention or treatment of neoplasia. Such an immunotherapy can be used in conjunction with the administration of other anti-neoplastic agents, e.g., chemotherapy, or radiation therapy, and be administered prior to, concurrent with, or following chemotherapy or radiation therapy.

The invention further provides a method of immortalizing a primary cell in culture by selecting at least two cells as having undergone spontaneous cell-cell fusion in a primary cell culture; and culturing the selected cells under conditions that promote further cell-cell fusion, thereby generating an immortalized cell. In an embodiment, the selected cells are multinucleate. In an embodiment, the cells are maintained in culture for sufficient time to allow partitioning of the multinucleate cells in culture to generate a population having at least 50% mononucleate aneuploid cells.

The invention further includes a non-human animal, preferably a non-human mammal having at cell or a population of tumor-initiating cells of the invention. In an embodiment, the cells are present in sufficient number to allow for formation of a tumor in the mammal.

The invention also includes the use of the tumor initiating cells of the invention to generate a differentiated cell by administration of growth factors or other agents to promote differentiation. The exact factors to be used depend on the type of differentiated cell desired. The invention further includes methods for amelioration or treatment of diseases or disorders associated with cell insufficiency by administering the differentiated cells of the invention to a subject in need thereof. The invention further includes a composition including a differentiated cell of the invention formulated for administration to a subject.

Definitions

"Aneuploid" or "aneuploidy" refers to a cell having an abnormal number of chromosomes relative to a corresponding reference cell. Most cells that are not undergoing cell division are diploid (2N). Cells in the G2 or M phase of growth can have 4N chromosomes.

By "anti-fusion agent" is meant an agent that can reduce the frequency or rate of cell-cell fusion. In particular, an anti-fusion agent inhibits any step in the process of cell fusion. In one embodiment, an anti-fusion agent acts by preventing the fusion of cells to produce multinucleate cells or by preventing the fusion of multinucleate cells to create tumor-initiating or highly tumorogenic cells having a single nucleus. In another embodiment, an anti-fusion agent acts by killing cells undergoing cell-cell fusion.

By "cell-cell fusion" is meant the melding of two or more cells to form a multinucleate cell. A cell that has recently undergone fusion is identified by the presence of two or more nuclei within a single cytoplasm, is identified using a detectable marker (e.g., quantum dots) to identify a single cytoplasm resulting from cell fusion, or is identified using any other method known in the art and described herein. Cells descended from a fused progenitor cell may contain a single nucleus that has split off from a multinucleate cell. Spontaneous cell-cell fusions described herein do not include cell fusions associated with virally induced cell fusions, with hybridoma cell fusions, or with cell fusions that occur during normal development. Specifically excluded from the definition of cells that arise during spontaneous cell-cell fusion are macrophages, myofibrils, or other cells that normally fuse in mammals under non-disease conditions. Spontaneous cell-cell fusions of the invention are generated in the absence of a virus. Virally fused cells are specifically excluded from the definition of cells that arise during spontaneous cell-cell fusion.

The term "detectable" refers to an agent that when linked with a nucleic acid molecule or protein of interest, or present in the cytoplasm or membrane not specifically attached to any protein or nucleic acid, facilitates detection. Detection is via any means known in the art, including spectroscopic, photochemical (e.g., luciferase, GFP), biochemical, immunochemical, chemical means, or direct observation. For example, useful labels include radioactive isotopes, magnetic beads, metallic beads, colloidal particles, fluorescent dyes, electron-dense reagents, enzymes (e.g., horseradish peroxidase, alkaline phosphatase), biotin, digoxigenin, or haptens. In particular embodiments, a detectable agent is one that can be readily observed, preferably in a quantitative manner, such as a fluorescent tag that has a specific wavelengths of absorption and emission to allow detection of the compound associated with the detectable label. Detectable labels include vital dyes for use with living cells, wherein the dye has little or no effect on cell viability, growth, and function.

As used herein, "descended from", "descended from a progenitor cell", and the like is understood as a cell that is produced by mitosis, or meiosis, or a result of the separation of at least one nucleus and some cytoplasm from a multinucleate cell.

As used herein, an "enriched population" or "population enriched for" cells having a desired characteristic comprises at least about 50% of cells having the characteristic that defines the population. An enriched population preferably has at least 70%, at least 75%, at least 80%, at least 85%, at least 90%, at least 95%, or at least 99% cells having the particular phenotype, genotype, or other characteristic that defines the population.

By "free of viruses" or "virus-free" is understood as containing no detectable virus. Preferably, a culture that is virus-free contains no detectable fusogenic virus, by any standard detection method, including diagnostic methods, PCR or other nucleic acid based method; western blot, ELISA, or other immune based method, viral culture methods, or any other methods known in the art.

As used herein, a "tumor-initiating cell" is a cell that has undergone cell-cell fusion, or a descendant of such a cell that is capable of generating a neoplasia under appropriate conditions in vitro or in vivo or which is capable of self-renewal. A cell that has undergone cell fusion has at least one of the following characteristics: has 2 nuclei wherein the nuclei did not arise from a single cell division and that typically divide asynchronously; or has at least 3 nuclei, preferably at least 4, 5, 6, 7, 8, 9, or 10 nuclei; or has been observed directly to undergo cell fusion; or observed indirectly to have undergone cell fusion by use of markers (e.g., GFP, RFP) or vital dyes.

As used herein, a "highly tumorogenic cell" exhibits at least about a 10-fold increase in tumorigenicity as compared to a corresponding reference cell. Preferably, a highly tumorogenic cell exhibits at least about a 20-fold, 50-fold, or 100-fold increase in tumorigenicity as compared to a corresponding reference cell. For example, a highly tumorogenic cell produces a tumor of 1 cm diameter in at least about 50%, 60%, 70%, 80% or more of nude mice from 1000 cells, 500 cells in less than 8 wks, 6 wks, 4 wks, 3, wks, 2, wks, 1 wk; or 100 cells, 75 cells, 50 cells, 25 cells, 10 cells, or 5 cells in less than about 12 weeks, 10 weeks, 8 weeks, 6 weeks, or even as little as 3 or 4 weeks.

A highly tumorogenic cell has a high tumor producing efficiency or a high colony producing efficiency, preferably as compared to a control cell. As used herein, "tumor producing efficiency", "efficiency of tumor production", and the like are determined by the number of cells required to produce a tumor in a specific percentage of animals within a specific time frame. For example, if 1000 of a first class of cells can produce tumors in 80% of animals at 2 months, and 100 of a second class of cells can produce tumors in 80% of animals at 2 months, the second class of cells are 10-fold more efficient than the first class of cells in producing tumors. Similarly, efficiency can be based on the percent of animals in which a tumor is produced when the cell number is held constant. Similarly, the number of colonies formed on soft agar from a first class of cells can be compared to the number of colonies formed on soft agar from a second class of cells.

As used herein, "multinucleate cell" is understood as a cell having more than one nucleus. For example, at least about 2, 3, 4, 5, 6, 7, 8, 9, or more nuclei.

A "mononuclear cell" or a "cell having a single nucleus" has one nucleus. A mononuclear cell can be aneuploid.

As used herein, a "normal cell" is a control cell. In particular, a normal cell is derived from a healthy tissue. Preferably, the normal cell does not include any known mutations that predispose the cell to transformation, and does not display apparent hyperplasia, abnormal or uncontrolled hyperproliferation, or reduced cell death or apoptosis (e.g., a non-cancer cell). In particular embodiments, a "normal cell" is not a naturally occurring, non-disease associated multinucleate cell, such as a myofibril, a macrophage, or bone marrow derived stem cells, or a naturally occurring, non-disease associated fused cell such as a gamete. As used herein, a neoplastic cell is a cell that displays apparent hyperplasia or abnormal or uncontrolled hyperproliferation or reduced cell death or apoptosis (e.g., a cancer cell, cells immortalized in culture, a transformed cell).

As used herein, "selecting" is understood as identifying and isolating or enriching for a cell having a desired characteristic. The selected members can be isolated from their original environment and can be pooled. In one embodiment, cells are selected for having undergone fusion. Alternatively, or in addition, selection can be performed based on the expression or the absence of expression of one or more proteins. Protein markers for which cells may be selected include, but are not limited to, CD44, CD24, B38.1, CD2, CD3, CD10, CD14, CD16, CD31, CD45, CD64, CD140b, and ESA. A cell can be selected for being "positive" for a marker, "low" for a marker, or "negative" for a marker, or for being positive, low, or negative for any of a combination of a number of markers. Cells that are positive exhibit detectable levels of a marker. Where the level of a marker in a cell is described as increased or decreased, the level is measured relative to the levels present in a reference cell (e.g., an untreated control cell). Methods for selecting cells are well known and include fluorescence activated cell sorting (FACS) and manual cell selection. The specific method of selection is not a limitation of the instant invention. Selection can be performed based on visual identification of cells having the desire properties, i.e., multinucleate cells. Selection can be performed for cells that may or may not have fused based on the mixing or absence of mixing of detectable cytoplasmic markers or labels (e.g., vital dyes, fluorescent proteins such as green FP and red FP), the amount of nuclear staining with more fluorescence indicative of more nuclei, or the size of cells.

By "population" is meant at least 2 cells. In a preferred embodiment, population is at least 5, 10, 50, 100, 500, 1000, or more cells.

By "obtain" is meant purchasing, synthesizing, or otherwise acquiring.

As used herein, a percent confluence is understood as the amount of surface area of a tissue culture dish or other container that is covered by adherent cells. Cells can be grown at essentially any density, depending on cell type.

As used herein "periodically increased expression" or "periodically reduced expression" or "periodically modulated expression" refers to a cyclic alteration in the level of a polypeptide or nucleic acid molecule over some period of time. Typically, the level of the polypeptide or nucleic acid molecule varies synchronously in at least about 25%, 50%, 75%, or even 100% of the population.

As used herein, "synchronous" is understood to mean coordinated. Synchronous can refer to cell division, i.e., cells that cycle synchronously, or expression of specific markers at different splits (i.e., p8, p9, etc), or both.

By "agents typically present in cell culture" is meant agents that are generally required for cell survival in vitro. Such agents include growth media (e.g., DMEM, F12, MEM, RPMI available commercially), growth factors in the form of purified growth factors or animal serum (e.g., bovine serum, fetal bovine serum, horse serum), antibiotics (e.g., penicillin, streptomycin, tetracycline), and nutrients (e.g., sugar). It is understood that the agents present in the media will depend upon the cell type. "Agents not typically in media" include agents that induce mutations or cell fusion, infectious agents, agents that induce DNA damage, agents that induce cell cycle arrest in non-confluent cultures.

By "isolated" is meant a material that is free to varying degrees from components which normally accompany it as found in its native state. "Isolate" denotes a degree of separation from original source or surroundings. For example, an isolated cell can be removed from an animal and placed in a culture dish or another animal. Isolated is not meant as being removed from all other cells. A polypeptide or nucleic acid is isolated when it is about 80% free, 85% free, 90% free, 95% free from other cellular material, or culture medium when produced by recombinant techniques, or substantially free of chemical precursors or other chemicals when chemically synthesized. An "isolated polypeptide" or "isolated polynucleotide" is, therefore, a substantially purified polypeptide or polynucleotide, respectively.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

By "reference" is meant a standard or control condition.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res., 19:5081 (1991); Ohtsuka et al., J. Boil. Chem. 260:2605-2608 (1985); Rossolini et al., Mol. Cell. Probes, 8:91-98 (1994)). The term nucleic acid is used interchangeably with gene, cDNA, mRNA, oligonucleotide, and polynucleotide.

The terms "identical" or percent "identity," in the context of two or more nucleic acids or polypeptide sequences, refer to two or more sequences or subsequences that are the same or have a specified percentage of amino acid residues or nucleotides that are the same (e.g., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

By "analog" is meant a molecule that is not identical, but has analogous functional or structural features.

By "small molecule" is meant a compound having a molecular weight of no more than about 1500 daltons, 1000 daltons, 750 daltons, 500 daltons. A small molecule is not a nucleic acid or polypeptide.

As used herein, the term "polymerase chain reaction" (PCR) refers to the methods of U.S. Pat. Nos. 4,683,195, 4,683,202, and 4,965,188, all of which are hereby incorporated by reference, directed to methods for increasing the concentration of a segment of a target sequence in a mixture of genomic DNA without cloning or purification. As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "recombinant DNA molecule" as used herein refers to a DNA molecule, which is comprised of segments of DNA joined together by means of molecular biological techniques.

As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

By "detecting" or "detection" and the like is meant the process of performing the steps for determine if an analyte is present. The amount of analyte present may be none or below the level of detection of the method.

As used herein, a "theranostic" is understood to describe the process of diagnostic therapy for individual patients to tailor a treatment for them based on the test results. The method includes determining if and which drug will work best for a given individual, and/or a monitoring method to determine changes in the therapeutic needs of the patient, e.g., due to the development of drug resistance. In an embodiment, a tumor-initiating cell of the invention is generated for a subject. Tumor-initiating cells are produced using normal cells, cells derived from a hyperplasia, or cells derived from a neoplasia (e.g., tumor).

By "ameliorate" is meant decrease, suppress, attenuate, diminish, arrest, or stabilize the development or progression of a disease.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. More than one dose may be required for prevention of a disease or condition.

As used herein, the terms "prevent," "preventing," "prevention," "prophylactic treatment" and the like refer to reducing the probability of developing a disorder or condition in a subject, who does not have, but is at risk of or susceptible to developing a disorder or condition. More than one dose may be required for prevention of a disease or condition.

By "alteration" is meant a positive or negative alteration. In one embodiment, the alteration is in the expression level or biological activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

The term "neoplasia" or "hyperproliferative disorder" includes malignancies characterized by excess cell proliferation or growth, or reduced cell death. In specific embodiments, the term "cancer" includes but is not limited to carcinomas, sarcomas, leukemias, and lymphomas. The term "cancer" also includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor. Tumors include solid tumors (i.e., non-blood tumors) and blood tumors.

As used herein, "obtaining" is understood as purchase, procure, manufacture, or otherwise come into possession of the desired material.

Cells and/or subjects may be treated and/or contacted with one or more anti-neoplastic treatments including, surgery, chemotherapy, radiotherapy, gene therapy, immune therapy or hormonal therapy, or other therapy recommended or proscribed by self or by a health care provider.

The term "subject" includes organisms which are capable of suffering from cancer or other disease of interest who could otherwise benefit from the administration of a compound or composition of the invention, such as human and non-human animals. Preferred human animals include human patients suffering from or prone to suffering from cancer or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. A human subject can be referred to as a patient.

A method for "predicting" or "diagnosing" as used herein refers to a clinical or other assessment of the condition of a subject based on observation, testing, or circumstances.

The term "differential" or "differentially" generally refers to a statistically significant different level in the specified property or effect. Preferably, the difference is also functionally significant. Thus, "differential binding or hybridization" is a sufficient difference in binding or hybridization to allow discrimination using an appropriate detection technique. Likewise, "differential effect" or "differentially active" in connection with a therapeutic treatment or drug refers to a difference in the level of the effect or activity that is distinguishable using relevant parameters and techniques for measuring the effect or activity being considered. Preferably the difference in effect or activity is also sufficient to be clinically significant, such that a corresponding difference in the course of treatment or treatment outcome would be expected, at least on a statistical basis.

The polymerase chain reaction (PCR) is a widely known method for amplifying nucleic acids. Of the PCR techniques, RT-PCR (Reverse Transcription-PCR), competitive RT-PCR and the like are used for detecting and quantifying a trace amount of mRNA, and show their effectiveness.

In recent years, a real-time quantitative detection technique using PCR has been established (TaqMan PCR, Genome Res., 6 (10), 986 (1996), ABI PRISM.™ Sequence Detection System, Applied Biosystems). This technique measures the amount of nucleic acids using a particular fluorescent-labeled probe (TaqMan probe). More specifically, this technique utilizes the following principles: For example, a fluorescent-labeled probe having a reporter dye at the 5' end and a quencher dye at the 3' end is annealed to the target DNA, and the DNA is subjected to normal PCR. As the extension reaction proceeds, the probe is hydrolyzed from the 5' end by the 5'-3' exonuclease activity possessed by DNA polymerase. As a result, the reporter dye at the 5' end is separated from the quencher dye at the 3' end, thereby eliminating the FRET (Fluorescence Resonance Energy Transfer, the reduction in fluorescence intensity owing to the decrease in the energy level of the reporter dye caused by the resonance of the two fluorescent dyes) effect produced by the spatial proximity between the two dyes, and increasing the fluorescence intensity of the reporter dye that has been controlled by the quencher dye. The target nucleic acid can be selectively quantified and detected in real-time by measuring the increase of the fluorescence intensity.

The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The language "therapeutically effective amount" or a "therapeutically effective dose" of a compound is the amount necessary to or sufficient to provide a detectable improvement in of at least one symptom associated or caused by the state, disorder or disease being treated. The therapeutically effective amount can be administered as a single dose or in multiple doses over time. Two or more compounds can be used together to provide a "therapeutically effective amount" to provide a detectable improvement wherein the same amount of either compound alone would be insufficient to provide a therapeutically effective amount.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the unstratified population. (Such a treatment may be ineffective in a subgroup that can be identified by the expression profile or profiles.) "Less effective" means that the treatment results in a therapeutically significant lower level of pharmacological effectiveness and/or a therapeutically greater level of adverse physiological effects, e.g., greater liver toxicity.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

In reference to response to a treatment, the term "tolerance" refers to the ability of a patient to accept a treatment, based, e.g., on deleterious effects and/or effects on lifestyle. Frequently, the term principally concerns the patients perceived magnitude of deleterious effects, such as nausea, weakness, dizziness, and diarrhea, among others. Such experienced effects can, for example, be due to general or cell-specific toxicity, activity on non-target cells, cross-reactivity on non-target cellular constituents (non-mechanism based), and/or side effects of activity on the target cellular substituents (mechanism based), or the cause of toxicity may not be understood. In any of these circumstances one may identify an association between the undesirable effects and variances in specific genes or responses of the cells from the subject to contact with an agent ex vivo.

Also in other embodiments, the method of selecting a treatment includes eliminating a treatment, where the presence or absence of certain profiles or responses of the enriched population of tumor-initiating cells from the subject to contact with an agent is indicative that the treatment will be ineffective or contra-indicated, e.g., would not reduce tumor size, would not stop tumor growth, and/or metastasis. In other preferred embodiments, in cases in which undesirable side-effects may occur or are expected to occur from a particular therapeutic treatment, the selection of a method of treatment can include identifying both a first and second treatment, where the first treatment is effective to treat the disease or condition, and the second treatment reduces a deleterious effect of the first treatment.

Usually, the treatment will involve the administration of a compound preferentially active or safe in patients with certain profiles or responses of the enriched population of tumor-initiating cells from the subject to contact with an agent ex vivo. The administration may involve a combination of compounds. Thus, in preferred embodiments, the method involves identifying such an active compound or combination of compounds, where the compound is less active or is less safe or both when administered to a patient having a different profile.

Also in some embodiments, the method of selecting a treatment involves selecting a method of administration of a compound, combination of compounds, or pharmaceutical composition, for example, selecting a suitable dosage level and/or frequency of administration, and/or mode of administration of a compound. The method of administration can be selected to provide better, preferably maximum therapeutic benefit. In this context, "maximum" refers to an approximate local maximum based on the parameters being considered, not an absolute maximum.

Also in this context, a "suitable dosage level" refers to a dosage level that provides a therapeutically reasonable balance between pharmacological effectiveness and deleterious effects. Often this dosage level is related to the peak or average serum levels resulting from administration of a drug at the particular dosage level.

Described herein, according to one aspect, are methods of predicting responsiveness of a tumor to therapeutic treatment by determining the response of the enriched population of tumor-initiating cells from the subject to an agent.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A shows confocal microscope images of MLF-MLF, MLF-LLC, and LLC-LLC fused cells. The presence of red (Qtracker® 655, Invitrogen) and green (Qtracker® 525, Invitrogen) quantum dots (Qdots) within a single cytoplasm identified fused cells. Nuclei are stained with To-Pro®-3 (Invitrogen) and given a blue pseudocolor. All photos are reconstructed z-stack images. Scale bar is 10 mm. The MLF-MLF cell fusion (left) is detected at an early stage, arrows point to Qdots being exchanged through the filopodia linking the two cells. Fusion of cells in different cell cycle phases is detected. Note both interphase nuclei and prophase nuclei within the same cell, LLC-LLC (right) and MLF-LLC (right). FIG. 1B shows FACS data from sorting of fused cells. Representative flow cytometry dot plots for the populations. FIG. 1C provides histograms showing the percentage of cell-cell fusions during twenty-four hours. Data is compiled from three separate biological replicate sorts with primary lung fibroblasts from different mice. Solid bars indicate % of cells detected which exhibited both red and green Qdots: 12.9±5.2% MLF-MLF, 24.8±14.6 for LLC-LLC, and 16.4±2.5 for MLF-LLC. The dashed bars take into account the fact that for the MLF-MLF and LLC-LLC cultures, twice as many cell-cell fusions must occur than are detectable by this methodology. MLF-LLC fusions are all directly detectable. FIG. 1D provides histograms showing the percentage of double-labeled cells detected after 24 hours. Data was compiled from three separate biological replicate sorts, in the case of the MLF using primary lung fibroblasts from different mice. Solid bars indicate % of cells detected which exhibited both red and green Qdots: 12.9%±5.2 (25.8±10.4% after compensation for calculated unseen green-green/red-red exchanges—striped bar) double-labeled MLF, 24.8%±14.7 (49.6%±29.4) double-labeled LLC, and 29.4±0.2% (58.8%±0.4) double-labeled MLF-MLFp25 cells. FIG. 1E is a schematic depicting the isolation and subsequent culturing of cells undergoing spontaneous cell-cell mixing in vitro. Red and green cells (labeled with Qdots) were co-cultured for 24 hours and then sorted for cells undergoing horizontal cell-cell exchange events (here depicted as yellow). Following further in vitro culturing the cells were injected into mice to assess tumorigenicity of the different populations.

FIG. 2A shows morphological changes in fused cells as detected via immunofluorescent staining of F-actin (red) with nuclear stain To-Pro®-3. Fused cells from early passages form syncytia (blue). Scale bar is 10 mm. MLF-MLF p4 exhibits organized F-actin stress fibers, not seen in MLF-LLC passages. For MLF-MLF cells transformation occurs around p13, accompanied by dramatic changes in both nuclei and F-actin (as compared to MLF p13 cells). Severed actin is detected along with the shape change occurring at that same passage. By MLF-MLFp17 cells have a phenotype strongly resembling the tumor line LLC. This occurs for MLF-LLC cells by p12. FIG. 2B shows measurements of average cell and nuclear area for MLF, LLC, and MLF-MLF p8, p10, p12, p13, p16, and p24 populations. These measures oscillate as a function of passage, consistent with cell-cell fusions and the emergence of smaller cells in which there has been a reassortment and repackaging of the nuclear material. The ratio settles to about the same value as that of the original LLC cells. FIG. 2C shows increasing rates of cell proliferation for fused fibroblasts (MLF-MLF) vs. non-fused (MLF) fibroblasts and increasing cell proliferation rates for MLF-MLF as a function of passage in culture (i.e. p8, p17 and p29). This is analogous to the increase in proliferation rate seen during the progression of tumor cells (Rubin 2007). FIG. 2D shows Hoffman modulation contrast image of population of MLF-MLFp13 undergoing transformation in culture as compared to MLFp7 or p31 cells. The transformed morphology of the vast majority of the MLF-MLFp13 population is noted. Black scale bar is 50 μm.

FIG. 3A shows the results of a soft agar transformation assay. Cultures of MLF, MLF-MLF p1 and MLF-MLF p7 show no transformed cell colonies, while MLF-MLF p17 and LLC show high transformation. Quantification indicates MLF-MLF p17 had 1137+−66 colonies, considerably more than the 776±515 scored for LLC and 0 colonies for MLF, MLF-MLF p1 and MLF-MLF p7 cultures. All dishes were seeded at 5000 cells, separate biological and three technical replicates were pooled. FIG. 3B shows a cytogenetic analysis of karyotype for cell populations via M-FISH for MLF-MLF p8 and MLF-MLF p17. MLF-MLF p8 showed extensive aneuploidy. MLF-MLF p17 had aneuploidy, a high degree of allele losses and gains and a significant number of translocations.

FIG. 4A shows representative tumors in C57/B16 mice after injection of $10^6$ MLF-MLF p8 or MLF-MLF p17 cells. Scale bars are 0.5 cm. Discrete multiple tumor nodules were characteristic of the MLF-MLF p17 tumors. Histological sections from MLF-MLF p8 and MLF-MLF p17 tumors stained with H&E demonstrate invasion of tumor cells into muscle tissue. Black scale bar for H&E is 100 μm. FIG. 4B shows tumor growth plotted for MLF-MLF p8, n=4 (blue), MLF-MLF p17, n=10 (red) and LLC, n=5 (black) populations in C57/B6 mice. Nonfused MLFs, n=10 (solid green) and MLFs loaded with Qdots®, n=10 (open green), were implanted as controls. For MLF-MLF p8, 50% (2/4) of the implants formed malignant tumors after a lag period of greater than 25 days. For MLF-MLFp17, 100% (10/10) grew malignant tumors with essentially no lag period, 2 days, the same as the murine epithelial Lewis lung carcinoma line.

FIGS. 6A and 6D shows orchestrated cyclic gene regulation detected for the classic genes associated with cancer, which include the oncogenes Myc, Kras, and Bcl-2; the tumor suppressors p53 and CDKn2a; the metastasis genes CD44 and SPP1 (OPN); and the angiogenesis gene VEGF, as measured by RT-PCR as a function of passage after fusion. Both CD44 and SPP1 (OPN) are also associated with normal cell-cell fusion. A synchronized regulation of cancer genes over the whole population was observed consequent to transformation. No such regulation was seen for these same genes in the control unsorted MLF population as a function of passage. FIGS. 6B and 6C shows immunofluorescent staining for CD44 (green) and MMP9 (green) and OPN (red) for MLF-MLF cells. Staining of Lewis lung carcinoma cells, LLC, is shown for reference. Nuclei stained with To-Pro®-3. Scale bars are 10 mm. Low to negligible levels of CD44 and MMP-9 were seen in cells of the early MLF-MLF passages but high levels of both were detected in later passages.

FIG. 7A shows a plot of the first time and average lag time for tumor onset as a function of number of injected MLF-MLF p25 cells. The results are seen to be nearly linear on the log plot. FIGS. 7B and 7C show plots of tumor growth (volume) for MLF-MLFp25 and MLF-MLFp24 cells: $10^6$ cells (n=12), 5000 cells (n=12), 500 cells (n=10), 50 cells (n=10), and 5 cells (n=10) were injected into C57B16 mice. The table shows both the numbers of mice at each dilution that had visible subcutaneous tumor burden and the numbers of mice that were sacrificed to date due to tumor burden, subcutaneous or internal. Note for some mice injected with only 5 or 50 cells, subcutaneous tumors appeared and then regressed. FIG. 7D shows a plot of the average lag time for tumor onset as a function of number of injected MLF-MLF p25 cells. The results are seen to be nearly linear on the log plot and closely fit the equation y=62.42−9.56× log 10(x), where y is the average lag time to tumor onset and x is the number of cells injected (red dashed line) (R2=0.997).

FIG. 8A shows the karyotype of the primary human adult prostate epithelial cells, confirming a normal composition. FIG. 8B shows flow cytometry dot plots. Cultures of the karyotypically normal prostate epithelial cell population were labeled with red (Qtracker 655) or green (Qtracker 525) quantum dots, co-cultured for 24 hours and then sorted for double-labeled cells, indicative of cell-cell exchange events. Left plot shows the uniformity of co-cultured cell population. Right plot shows cells as function of red or green Qtracker and the gating for double positives, Epi-Epi, cells (Gate R2=19.06%). FIG. 8C shows confocal microscopic images of prostate epithelial co-cultures. FIG. 8C, Panels A and B show the presence of red and green quantum dots within a single cytoplasm identified cells actively involved in cytoplasmic exchange. FIG. 8C, panels C and D show cell structure filaments stained with F-actin (red) including both quantum dots. Blue corresponds to nuclei stained with To-Pro-3. Scale bar is 10 µm. FIG. 8D shows bright field microscopic images of prostate epithelial cell cultures. FIG. 8D, panel a is an image of the original prostate epithelial cell population pre-sort (passage 4). FIG. 8D, panels b-f are representative images of double-labeled, Epi-Epi, post-sort (passage 2) exhibiting altered cellular and population morphology and characteristic of transformed cell population in vitro. Scale bar 200 µm.

FIG. 10, panel a shows a subcutaneous tumor on nude mouse injected with 50,000 transformed cells. Upper arrow points to site of subcutaneous injection and lower arrow to tumor. FIG. 10, panel a1 is a histological image of a tumor slice stained with hemotoxylin and eosin (H&E) revealing well-differentiated adenocarcinoma morphology. FIG. 10, panel b is an image of calcified lymph node (lower arrow) present close to prostate region and distinctly enlarged prostate coagulating gland (upper arrow). FIG. 10, panel b1 is a histological image of prostate tissue from FIG. 10, panel b stained with H&E showing cancer cells invading mouse prostate. FIG. 10, panel c shows a solid tumor mass found near abdomen. FIG. 10, panel c1 is a histological image stained with H&E showing cancer cells infiltrating intestine lumen. FIG. 10, panel d shows that subcutaneous injection of 100,000 fused cells led to growth of internal tumor mass near chest cavity. FIG. 10, panel d1 is a histological image of H&E staining of the tumor in FIG. 10, panel d. FIG. 10, panel e shows an enlarged prostate from tumor burden (arrow). FIG. 10, panels e1, e2, and e3 are histological images of H&E staining showing human prostate cancer cells invading and fully integrating into the mouse prostate. FIG. 10, panel f shows examples of metastatic kidney tumor (note size and discoloration). FIG. 10, panel f1 is a histological image of H&E staining of the tumor in FIG. 10, panel f. FIG. 10, panel g shows lung tumor after serial in vivo passing. FIG. 10, panel g1 is a histological image of H&E staining of the tumor in FIG. 10, panel g. FIG. 10, panel h show kidneys, spine (left arrow) and infiltrated lymph node (right arrow). FIG. 10, panel h1 is a histologically image of H&E staining showing cancer cells infiltrating bone. FIG. 10, panel i shows metastasis in liver. FIG. 10, panel i1 is a histological image of H&E staining showing invading tumor cells in liver. Tissue/organs/animal scale bar: 3 mm. H&E scale bar: 100 µm.

FIG. 11A shows immunohistochemical detection of human PSA protein. FIG. 11A, panels a, b, and c show that high PSA expression (3-4) was detected in cancer cells infiltrating the mouse prostate. Clean staining PSA detected only in tumor cells which had invaded the prostate region after subcutaneous injection on the mouse back. FIG. 11A, panel d shows PSA expression in subcutaneous tumor. FIG. 11A, panels e and f shows PSA expression in lung tumor. Scale bar: 50 µm. FIG. 11B shows fluorescence in situ hybridization (FISH) on prostate tumor tissue sections. FISH was performed on frozen tissue sections with a probe for human PSA (green). The nuclei of the cells were stained with To-Pro-3 (blue). The first row demonstrates no detection in lung tissue from a control mouse that was injected with single-labeled post-sort Epi cells. No tumors were detected at sacrifice or by histology in any of the control mice. The next three rows demonstrate positive PSA detection in mouse tumors that originated from transformed, Epi-Epi cells. The white scale bar represents 10 µm. FIG. 11C shows immunofluorescent staining on frozen tissue. The first row demonstrates no antibody staining for PSA in lung tissue from a control mouse injected with single-labeled post-sort Epi cells. The next three rows demonstrate positive PSA (red) in mouse tumor tissue that originated from the transformed double-labeled Epi-Epi p2 cells. Nuclei were stained with To-Pro-3 (blue). The white scale bar represents 20 µm. FIG. 11D depicts upregulation of PSA mRNA detected along with downregulation of NKX3-A mRNA and PAWR mRNA in Epi-Epi cells in vitro undergoing transformation in vitro. RT-PCR analysis was conducted as a function of in vitro passage for the human prostate epithelial cells, both pre and post sort. RT-PCR analysis demonstrated that following their sorting and subsequent culturing the double-labeled cells, Epi-Epi, increased expression of PSA to >10× over that of the original unsorted population. PSA upregulation was seen to coincide with the downregulation of the well-known prostate tumor suppressor genes, NKX3-A and PAWR. No upregulation of PSA or downregulation of the tumor suppressor genes was seen for the control single-labeled Epi cell populations. Rather these control population cells showed a transient decrease in PSA and increase in the tumor suppressor genes. The data are normalized to the prostate epithelial cell population before sorting. FIG. 11E depicts Western blot analysis detecting human PSA in tissue taken from tumor-bearing mice but not from control mice. Anti-human PSA western of cell lysates from liver of control mice (injected with Epi cells from the single-labeled sort) (lane 1), tumor-infiltrated prostatic lymph node (lane 2), and lung tumor (lane 3).

DETAILED DESCRIPTION OF THE INVENTION

Figure 1:
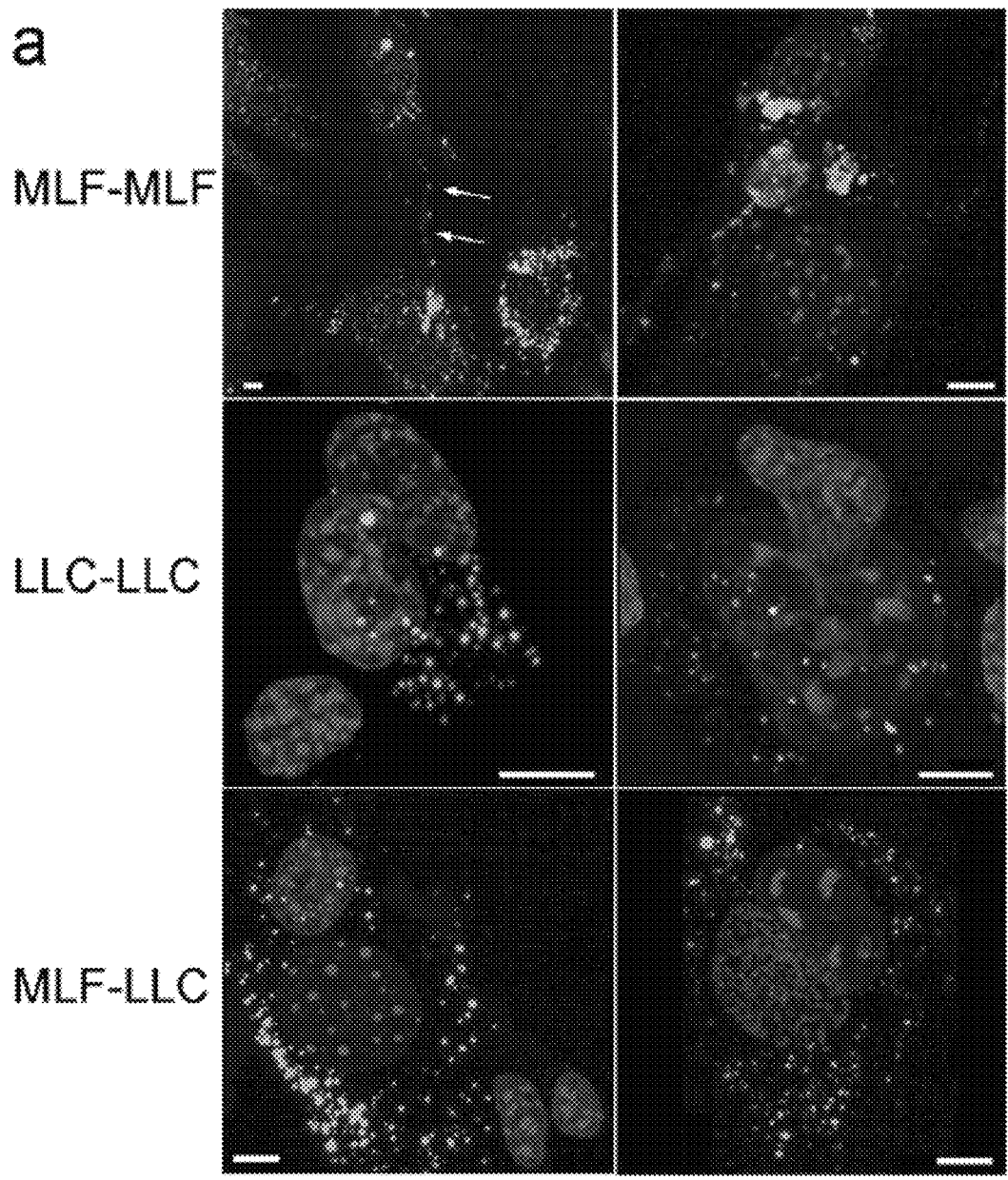
FIGS. 1A-1E relate to spontaneous cell fusion in vitro. Cultures of primary murine lung fibroblasts (MLF), Lewis lung carcinoma (LLC) cells and co-cultures were labeled, cultured for twenty-four hours and then sorted for fusion events.
Figure 1:
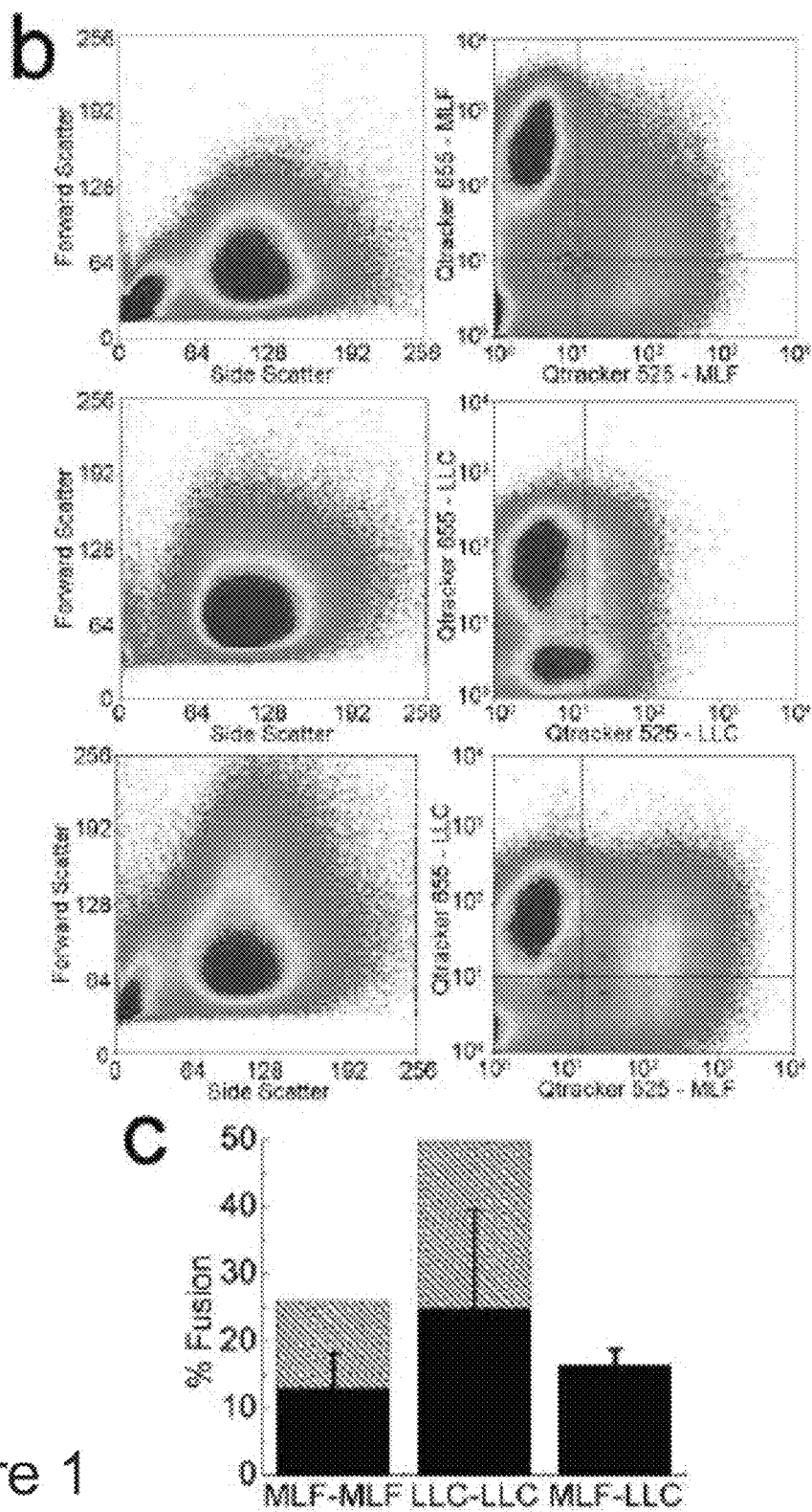
Figure 1:
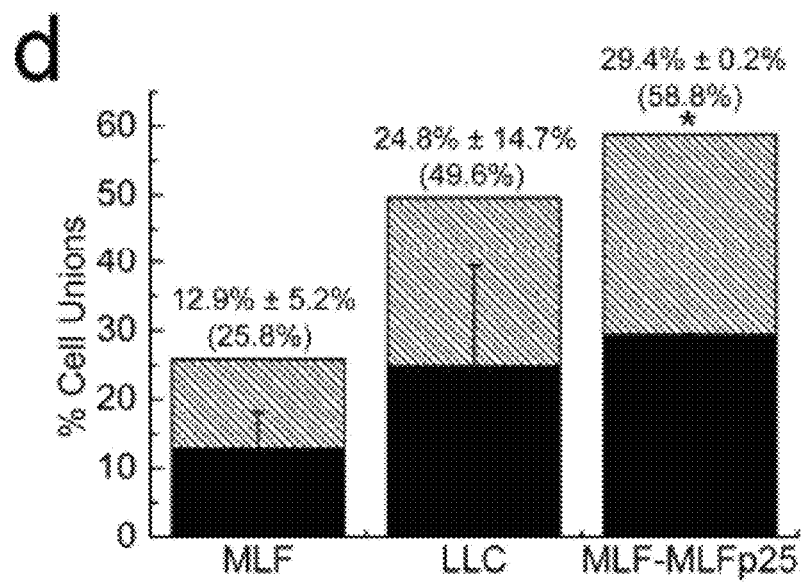
Figure 1:
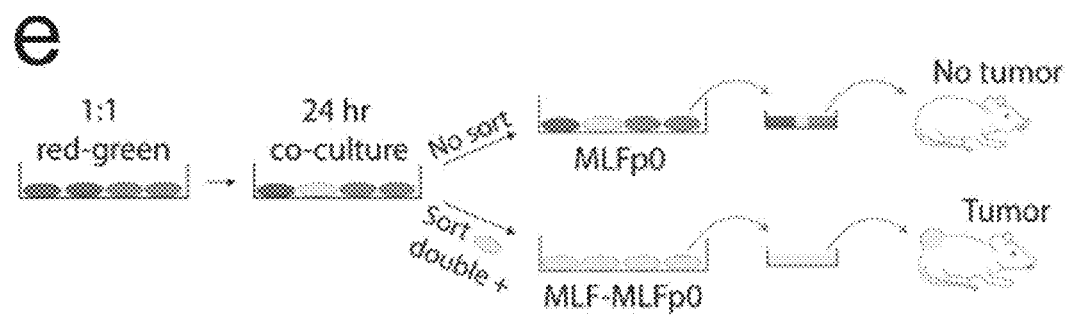

The invention provides tumor-initiating cell compositions, methods for producing a tumor-initiating cell, and the use of such cells for the identification of agents useful for the treatment or prevention of neoplasia and for the treatment or prevention of relapse following chemotherapy or radiation therapy. Desirably, tumor-initiating cells of the invention are self-renewing and stem-cell like. Accordingly, the invention further provides methods for driving the differentiation of a tumor-initiating cell of the invention towards a differentiated phenotype.

The invention is based, at least in part, on the discovery that selection and culturing of cells created in cell-cell fusion events generates one or more neoplastic cells. Such cells are capable of producing neoplasia in vitro or in vivo. As described in more detail below, the selection of cells that have undergone spontaneous cell fusion among primary adult murine fibroblasts or human prostate epithelial cells in vitro was sufficient to create a population of cells that induced high-grade malignant tumors in vivo with 100% efficiency. Despite the absence of viral, genetic or other manipulations, these cells exhibited the classic hallmarks of cancer. Careful characterization of mouse fibroblasts selected in this way revealed changes characteristic of cancer, including aneuploidy; chromosome-level aberrations, upregulated oncogenes (myc, k-ras, EGFR, Bcl-2), downregulated tumor suppressor genes (CDKn2a), upregulated invasion, metastasis and angiogenic genes (MMP9, CD44, OPN, VEGF), genomic instability, and a continuously increasing proliferation rate.

Strikingly, the dysregulation of oncogenesis genes occurred simultaneously with the transformation event. These results indicate that a classic cancer cell genotype need not arise through selection acting on random mutations, but rather can arise as part of a deterministic, programmed genomic response to spontaneous cell fusion events. In sum, spontaneous cell-cell fusions can initiate and drive the essential aspects of carcinogenesis, including transformation, progression, invasion, metastasis and self renewal thereby providing further mechanistic understanding of cancer induction.

Spontaneous cell-cell fusion as provided herein is not driven by viruses, synthetic agents, or inserted heterologous genetic material (e.g., oncogenes). As described herein, the fusion process is driven by the selection of cells that have undergone fusion. If desired, such cells can be grown under conditions that sufficient to promote multiple rounds of fusion, thereby generating multinucleate cells. These multinucleate cells are precursors of tumor-initiating mononuclear cells. Tumor-initiating cells of the invention are used to generate animal models of metastatic cancer and cancer in nude mice, as well as in non-immune compromised animals.

Methods for Generating Tumor-Initiating Cells

Tumor-initiating cells of the invention are generated by establishing primary cells in culture and selecting those that have undergone fusion according to the methods described herein or any other method known in the art. In one embodiment, such cells are grown in culture at a relatively high density (plating at about 80% confluence) or under other conditions sufficient to promote further cell-cell fusion events. In a preferred embodiment, cells are identified as having fused by detecting the exchange of soluble cytoplasmic markers, such as Qdots® which are vital dyes that do not induce cell fusion, or cells can be derived from transgenic animals, such as mice, that express fluorescent proteins, such as green fluorescent protein (GFP) or red fluorescent protein (RFP) in a tissue of interest. In one alternative embodiment, detectable markers incorporated in the cell membrane can be used. Cells with at least two distinct detectable markers are co-cultured for preferably at least about eight and more preferably for at least about twenty-four hours. Cells having the two distinct markers are identified as having fused. Cells are also identified as having fused if they have two nuclei that are not a result of mitosis or meiosis. Cells having at least three nuclei have clearly undergone cell fusion.

While the examples provided herein specifically describe methods for selecting tumor-initiating cells from fibroblast and epithelial cultures, the invention is not so limited. Cells for use in the methods of the invention can be isolated from a number of sources, including, for example, from a tissue of a patient. In one embodiment, the isolated cells are autologous cells obtained from healthy tissue or from a neoplasia biopsy from a subject. The cells from biopsy are expanded in culture. Such cells are isolated using techniques known to those skilled in the art. For example, a tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with digestive enzymes (e.g., trypsin, chymotrypsin, collagenase, elastase, hyaluronidase, DNase, pronase, and dispase). Mechanical disruption can be accomplished by scraping the surface of the organ, the use of grinders, blenders, sieves, homogenizers, pressure cells, or sonicators. For a review of tissue disruption techniques, see Freshney, (Culture of Animal Cells. A Manual of Basic Technique, 2d Ed., A. R. Liss, Inc., New York, Ch. 9, pp. 107-126, 1987).

Once a tissue has been reduced to a suspension of individual cells, the suspension can be fractionated into subpopulations. This may be accomplished using standard techniques (e.g., cloning and positive selection of specific cell types or negative selection, i.e., the destruction of unwanted cells). Selection techniques include separation based upon differential cell agglutination in a mixed cell population, freeze-thaw procedures, differential adherence properties of the cells in the mixed population, filtration, conventional and zonal centrifugation, unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, Ch. 11 and 12, pp. 137-168, 1987). The use of autologous cells, is preferred. As described herein, such cells are used for the selection of individualized therapeutic agents for the subject from whom the cells are derived or from another subject. Alternatively, such cells are used for the production of antineoplasia vaccines for the subject from whom the cells are derived or from another subject. Methods of therapy selection and for vaccine production are described below.

Based on results reported herein, tumor-initiating cells are more resistant to chemotherapeutic agents, radiation, and other insults due to their ability to recombine to correct genetic damage induced by the insults. Therefore, it should be possible to identify a subpopulation of tumor-initiating cells by their resistance to insults. Cells are cultured at a sufficiently high density (at least 80% confluent) preferably for sufficient time to allow for more than one round of cell fusion, at least about 24 hours, preferably about 48 to 72 hours. Cells are then subjected to an insult sufficient to kill most of the cells. Dead cells are removed, and the remaining viable cells are transferred to a culture of high density (e.g., at least about 80% confluent).

Figure 6:
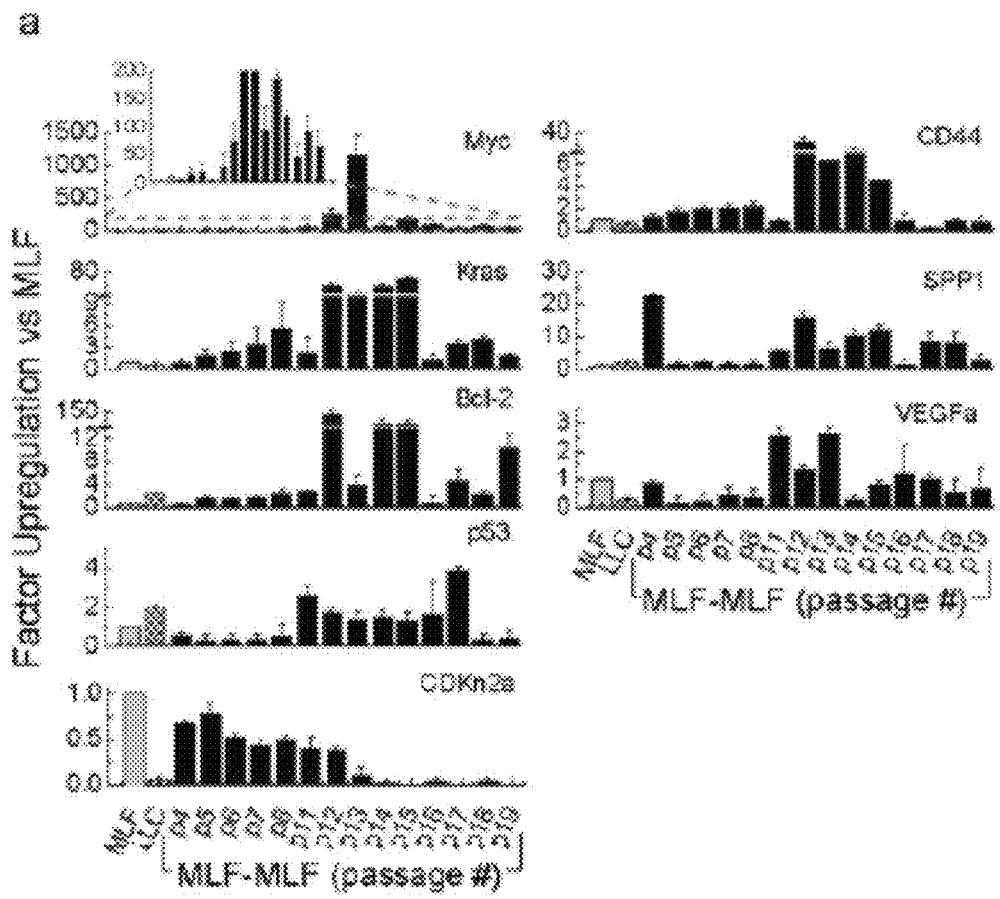
FIGS. 6A-6D show a molecular characterization of the transformation process. Protein and RNA of genes associated with carcinogenesis for fused fibroblasts, as a function of passage.
Figure 6:
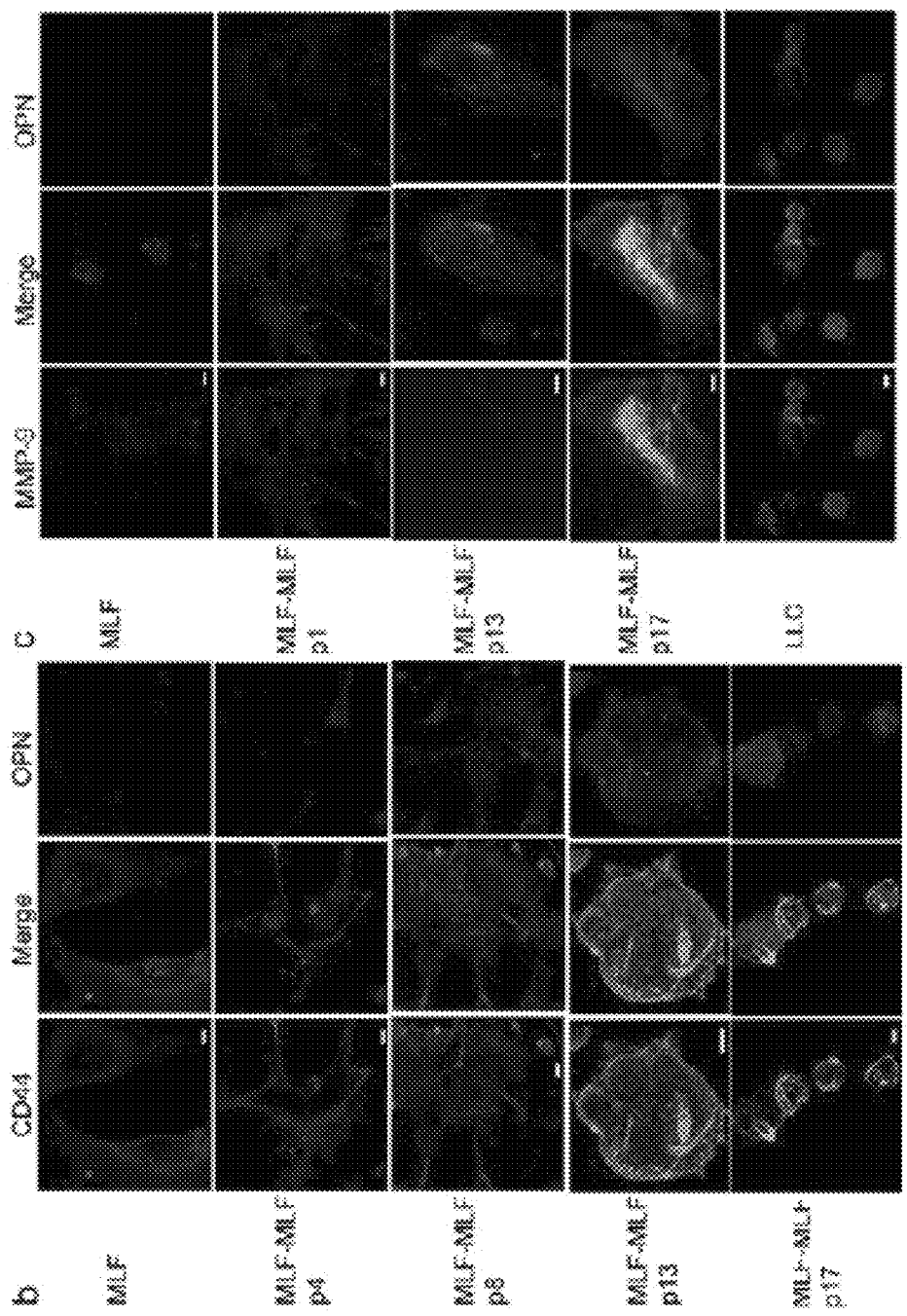
Figure 6:
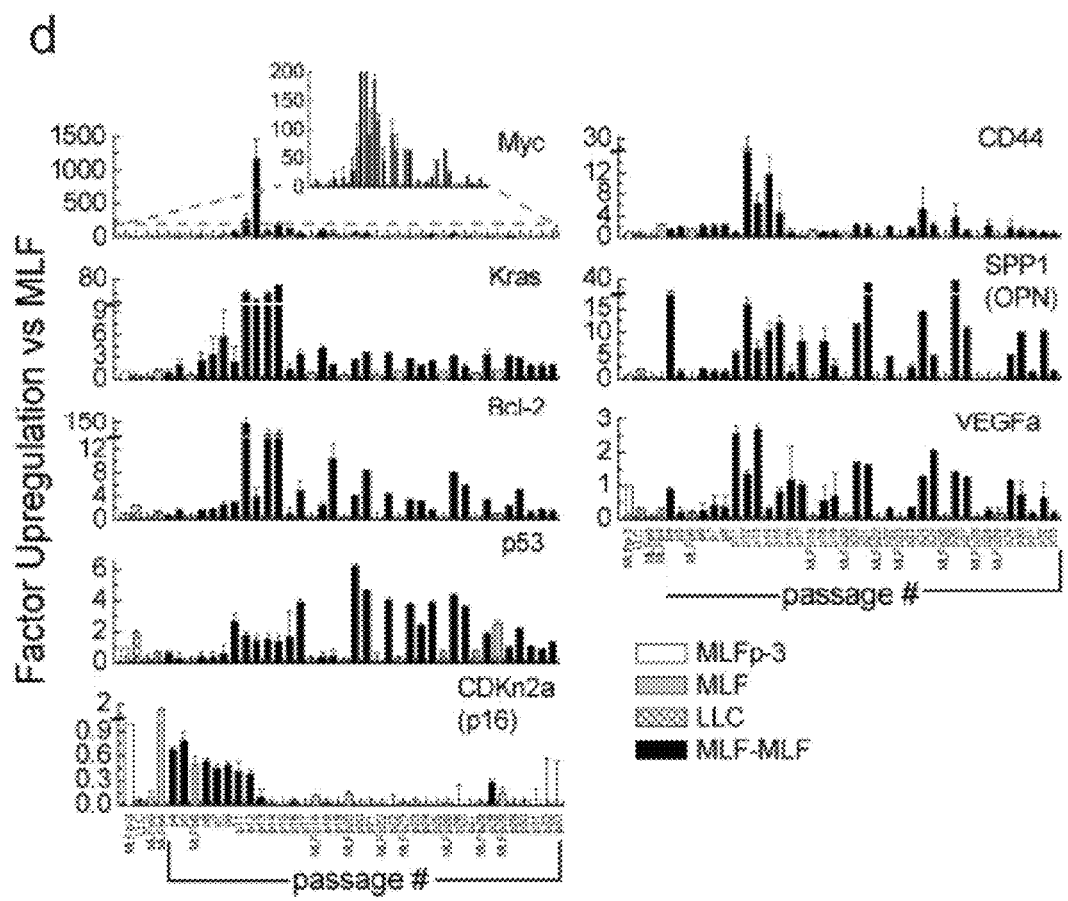

Cells that have undergone fusion can be identified based on marker expression. As disclosed herein, tumor-initiating cells of the invention undergo a program of synchronous expression and non-expression of specific cell markers (e.g., increased expression of classic oncogenes, such as myc, k-ras, EGFR, Bcl-2, decreased expression of tumor suppressor gene CDKn2a, increased expression of invasion, metastasis and angiogenic genes MMP9, CD44, OPN, VEGF). If desired, cells are co-cultured at sufficiently high density to promote further fusion events. In one embodiment, cells are cultured for sufficient time to allow for more than one round of cell fusion, and selected for expression and/or non-expression of cell markers. Appropriate markers can be selected based on the data in FIG. 6.

Fluorescent labels allow for the sorting of cells that have fused using a fluorescent activated cell sorter (FACS) machine. Cells can also be sorted manually. The specific method of sorting and isolation is not a limitation of the invention. The isolated subpopulation of cells are plated at a high density of at least about 80% confluent to promote further cell fusion.

The isolation of the subpopulation of cells results in a culture that is both synchronous in the expression of markers, and therefore not surprisingly synchronous in the progression of a series of morphological changes, from mononucleate, to multinucleate, to cytoskeletal collapse, to mononuclear cells with high nuclear to cytoplasmic ratio.

Screening Assays

The invention provides for the selection of tumor-initiating cells. Such cells may be used to identify novel therapeutic agents for the treatment of neoplasia. Without wishing to be bound by theory, cell-cell fusion may be the original step that gives rise to a neoplasia or to a neoplastic precursor cell. Accordingly, compositions of the invention are useful to identify agents that reduce the generation, proliferation, and/or survival of such cells.

As reported herein, tumor-initiating cells progress through a series of phenotypic stages in culture. Interruption of the process at any step will likely disrupt the formation of tumor-initiating cells. Methods for screening agents for therapeutic activity are well known in the art. It is understood that initial screening methods in vitro typically lead to the further testing of compounds both in vitro and in vivo. Screening assays can be combined to characterize agents with potential therapeutic activity. Agents can be selected based on functional or structural homology (e.g., chemotherapeutic agents, kinase inhibitors), combinatorial chemistry libraries, natural compound libraries, approved drug libraries, peptide libraries, etc. Agents can also be rationally selected based on their known function. Osteopontin, for example, is likely to be useful to inhibit production of a tumor-initiating cell because of its biological activity as an inhibitor of cell fusion. In all screening assays, agents are preferably tested in duplicate or triplicate and appropriate controls, preferably both positive and negative, are run to allow for determining relative activity of the agent. The ability to design proper controls is within the ability of those of skill in the art.

In vivo, tumor cells may not synchronously proceed through the steps observed herein to generate tumor-initiating cells or a synchronous program of marker expression. Therefore, an effective therapeutic intervention may, if desired, include administration of a combination of compounds that disrupt different steps in the process. Similarly, administration of an agent to disrupt the formation of tumor-initiating cells in combination with one or more known chemotherapeutic agents may also be useful.

The invention provides for the generation of isolated cultures enriched for cells that are synchronous as they proceed through the steps of cell fusion, multinucleate cell formation, and partitioning into mononuclear cells. Isolated cultures of tumor-initiating cells are prepared, and agents are added to the cultures at discrete time points—prior to fusion, prior to partition of mononuclear cells from the multinucleate cell, or after partition of mononuclear cells from the multinucleate cell. It is noted that the formation of tumor-initiating cells can be accomplished by specifically killing the multinucleate cells or the mononuclear cells partitioned from the multinucleate cell. Agents that prevent fusion by killing the initial cell population prior to fusion may also be useful. The exact times for administration of agents and detection of changes in growth or other phenotypic or genotypic changes can be readily determined by those of skill in the art.

Agents can also be tested for their ability to reduce tumorogenicity of cells in either a soft agar growth assay or a tumorogenicity assay in animals, such as rats or mice. Such methods are described herein and well known to those of skill in the art.

Screening for Agents that Inhibit Cell Fusion or the Growth of the Descendants of Such Cells Cell-cell fusion results in the generation of highly tumorogenic and metastatic cells. Such cells may be responsible for tumor resistance to chemotherapeutic agents or to radiotherapy. However, chemotherapeutic agents have necessarily been tested for activity against bulk tumor because no methods for isolating cancer stem cells. Using the tumor-initiating cells of the invention, therapeutic and prophylactic agents can now be tested for the ability to disrupt cell fusion, the ability to inhibit production of mononuclear cells from a multinucleate cell, and/or to inhibit the generation of tumor-initiating and/or metastatic cells of the invention. Agents can also be tested for their ability to kill rare tumor-initiating cells that are resistant to conventional chemotherapeutic agents and radiation therapy. Such agents can include single agents or libraries of compounds with or without structural of functional similarities.

Cells that have undergone fusion are identified using cytoplasmic vital dyes, by nuclear staining to identify cells with at least 4N DNA content or multinucleate cells that are not in the G2 or M phase of the cell cycle, or by direct observation of the cells. In one embodiment, cells are sorted using a FACS machine and plated into multiwell plates at a density of at least 80% to promote cell fusion.

To identify agents that inhibit cell fusion, agents are added to the wells at or around the time of plating, or at the latest prior to the initiation of cell fusion. The agent is preferably applied to wells in duplicate or triplicate with appropriate control wells (e.g., vehicle control, positive control) for comparison. Appropriate time frames can vary between cell types and be readily determined by empirical observation. The amount of cell fusion is determined, for example, by direct observation or by FACS analysis after the desired time period after exposure to the agent (e.g., about 12 hours, 24 hours, 48 hours, 72 hours or longer). In one embodiment, compounds are administered at a dose that does not kill the cells, but instead inhibits fusion. Compounds found to inhibit fusion can be tested and characterized, for example, for the ability to reduce the formation of colonies on soft-agar or to reduce tumor formation in mice. Agents found to inhibit cell fusion are useful in treating or preventing the progression of hyperplasia to more severe disease or hyperproliferative disorders. Agents that may inhibit fusion include, but are not limited to, CD44 antagonists, CD 133, and osteopontin.

To identify agents that kill fused, multinucleate cells, cells able to undergo fusion are selected at plated at a density of at least about 80% confluency and allowed to undergo fusion until at least about 50% of the cells are multinucleate prior to contacting the cells with the agent. The agent is preferably applied to wells in duplicate or triplicate with appropriate control wells (e.g., vehicle control, positive control) for comparison. Appropriate time frames can vary between cell types and be readily determined by empirical observation. The amount of viable multinucleate cells are determined for example by direct observation or FACS analysis after the desired time period after exposure to the agent (e.g., about 12 hours, 24 hours, 48 hours, 72 hours or longer). Wells are also observed for the generation of mononucleate cells in response to the agent. Agents found to kill fused cells or prevent formation of single nucleate cells from the fused cell can be tested and characterized further for example for the ability to reduce the formation of colonies on soft-agar or to reduce tumor formation or halt tumor growth in mice. Agents may or may not be useful in killing the bulk of tumor cells in animal models; however, upon killing of the most tumorogenic cells, the tumor should cease to grow and eventually die.

To identify agents that kill mononucleate cells derived from multinucleate cells, cells able to undergo fusion are selected at plated at a density of at least about 80% confluency, allowed to undergo fusion until at least about 80% of the cells are multinucleate, and subsequently produce multinucleate cells prior to contacting the cells with the agent. The agent is preferably applied to wells in duplicate or triplicate with appropriate control wells (e.g., vehicle control, positive control) for comparison. Appropriate time frames can vary between cell types and be readily determined by empirical observation. The amount of viable cells are determined for example by direct observation or FACS analysis after the desired time period after exposure to the agent (e.g., about 12 hours, 24 hours, 48 hours, 72 hours or longer). Agents found to kill mononucleate cells from fused cells can be tested and characterized further for example for the ability to reduce the formation of colonies on soft-agar or to reduce tumor formation or halt tumor growth in mice. Agents may or may not be useful in killing the bulk of tumor cells in animal models; however, upon killing of the most tumorogenic cells, the tumor should cease to grow and eventually die.

Therapy Selection

The highly tumorogenic cells provided herein can be generated from normal or from neoplastic cells. It is known that different cancers respond to different therapeutic agents, or combinations of agents, differently depending on the specific characteristics of the tumor, and the genetic makeup of the subject in whom the tumor is present. Tests have been developed to characterize tumors, including, for example, the Oncotype DX by Genomic Health, which contains sixteen genes associated with breast cancer and five control genes. This test can predict the likelihood of cancer recurrence and provide information regarding which chemotherapeutic interventions are likely to be most useful. However, such a test can only look at the bulk properties of the tumor and cannot provide information on highly tumorogenic cells that may be present in the population.

Normal and/or abnormal cells are obtained from an individual diagnosed with cancer. Primary cultures are generated using methods appropriate to the specific cell type to be cultured. Rates of generation of fused cells can be compared between the normal cells in culture and the abnormal cells in culture. A higher rate of generation of fused cells in the culture may suggest increased malignancy of the tumor.

Normal and/or abnormal cells that have been grown in culture to obtain an enriched population of tumor-initiating cells can be tested for response to a panel of approved chemotherapeutic agents. Depending on the stage of the tumor in the subject, different compounds can be tested at different phases of the culturing of the cells for the ability to inhibit fusion and/or kill cells. Chemotherapeutic agents that can be tested include, but are not limited to alkylating and alkylating-like agents such as nitrogen mustards (Chlorambucil, Chlormethine, Cyclophosphamide, Ifosfamide, Melphalan, Bendamustine, Uramustine), nitrosoureas (Carmustine, Fotemustine, Lomustine, Streptozocin); platinum (alkylating-like): (Carboplatin, Cisplatin, Oxaliplatin, Triplatin tetranitrate, Satraplatin), alkyl sulfonates (Busulfan, Treosulfan); hydrazines (Procarbazine, Dacarbazine, Temozolomide); and aziridines (ThioTEPA); antimetabolites such as folic acid analogs (Aminopterin, Methotrexate, Pemetrexed, Raltitrexed); purine analogs (Cladribine, Clofarabine, Fludarabine, Mercaptopurine, Pentostatin, Thioguanine); and pyrimidine analogs (Capecitabine, Cytarabine, Decitabine, Fluorouracil, Floxuridine, Gemcitabine); spindle poison/mitotic inhibitor Taxane (Docetaxel, Larotaxel, Paclitaxel); Vinca (Vinblastine, Vincristine, Vindesine, Vinorelbine); cytotoxic/antitumor antibiotics of the anthracycline family (Daunorubicin, Doxorubicin, Epirubicin, Idarubicin, Mitoxantrone, Pixantrone, Valrubicin); *streptomyces* (Actinomycin, Bleomycin, Mitomycin, Plicamycin); Hydroxyurea; topoisomerase inhibitors Camptotheca (Camptothecin, Topotecan, Irinotecan, Rubitecan); Podophyllum: (Etoposide, Teniposide); CI monoclonal antibodies; receptor tyrosine kinase (Cetuximab, Panitumumab, Trastuzumab); CD20 (Rituximab, Tositumomab); and other chemotherapeutic agents (Alemtuzumab, Bevacizumab, Gemtuzumab) Photosensitizers Aminolevulinic acid, Methyl aminolevulinate, Porfimer sodium, Verteporfin Tyrosine kinase inhibitors Axitinib, Bosutinib, Cediranib, Dasatinib, Erlotinib, Gefitinib, Imatinib, Lapatinib, Lestaurtinib, Nilotinib, Semaxanib, Sorafenib, Sunitinib, Vandetanib Cyclin-dependent kinase inhibitor Seliciclib Other retinoids (Alitretinoin, Tretinoin), Fusion protein (Aflibercept)-Altretamine, Amsacrine, Anagrelide, Arsenic trioxide, Asparaginase (Pegaspargase), Bexarotene, Bortezomib, Celecoxib, Denileukin diftitox, Elesclomol, Estramustine, Irofulven, Ixabepilone, Masoprocol, Mitotane, Oblimersen, Testolactone, Tipifarnib, Trabectedin.

Response of the enriched tumor-initiating cell population to the agent in culture is likely predictive of the response of the tumor in vivo. The usefulness of the method can be tested in animal models of cancer.

Anti-Neoplasia Vaccines

Anti-neoplasia vaccines are useful as therapeutics for the treatment of specific types of cancer. Advantageously, these vaccines may be tailored to treat the cancers of particular individuals, by generating vaccines that target specific tumor antigens expressed on a tumor in a subject. Anti-neoplasia vaccines of the invention are particularly useful because they provide for the targeting of tumor-initiating cells that are responsible for neoplasia relapse. Anti-neoplasia vaccines typically contain inactivated tumor cells or tumor antigens that stimulate a patient's immune system. The immune system responds to this stimulation by generating immunoresponsive cells that target the neoplasia. In particular embodiments, anti-neoplasia vaccines of the invention desirably target tumor-initiating cells, thereby preventing relapses of the neoplasia. Unlike vaccines for other diseases that prevent the occurrence of the disease, anti-neoplasia vaccines are typically administered after a subject has been identified as having a neoplasia.

Anti-neoplasia cell vaccines are produced using the cellular compositions of the invention, which are generated as described herein. In particular, a tumor-initiating cell is produced by isolating fibroblasts, epithelial cells, or other cells from a subject and/or isolating a tumor cell from the subject. In one approach, primary cells are isolated and cultured in vitro. Cells that have undergone cell-cell fusion in vitro are selected according to a methods described herein (e.g., using quantum dots, identifying cells having one or more nuclei). If desired, the cells are cultured at high density to promote further fusion events. Preferably, the cells are cultured at high density, and passaged between at least about 3-25 times (e.g., 3, 5, 7, 8, 9, 10, 11, 12, 13, 14, 15, 16, 17, 18, 19, 20, 21, 22, 23, 24, 25). Cells generated by this process are highly tumorogenic. The cells are killed and injected into the patient where the tumor-initiating cell antigens stimulate an immune response. Desirably, the immune system targets the small population of tumor-initiating cells that carry one or more antigens that was displayed on the dead cells. In other embodiments, selected cells are cultured together with isolated tumor cells, and tumor cell-normal cell (e.g., fibrobast, epithelial cell) fusions are selected. In still other embodiments, tumor cell-tumor cell fusions are selected.

In particular embodiments, cells of the invention synchronously express particular antigens, which allows for the analysis of protein expression at various points during the fusion process. Identification of antigens expressed prior to or during fusion allows for the production of a vaccine that prevents cell fusion.

The methods provided herein can also be used for the generation of a vaccine for specific treatment of neoplasias in individuals. Cells are obtained from normal or neoplastic cells from the individual and cultured to identify markers present on tumor-initiating cells. Rapid methods of screening for recombinant antibodies, such as single chain humanized antibodies, can be performed to select an agent appropriate for treatment of cancer in a specific individual.

Antigen vaccines use tumor-specific antigens—proteins displayed on a tumor cell—to stimulate the immune system. By injecting these antigens systemically or into the neoplastic area of the patient, the immune system produces antibodies or cytotoxic T lymphocytes to attack neoplastic cells that carry that specific antigen. Multiple antigens can be used in this type of vaccine to vary the immune system response.

Typically vaccines are prepared in an injectable form, either as a liquid solution or as a suspension. Solid forms suitable for injection may also be prepared as emulsions, or with the polypeptides encapsulated in liposomes. The cells are injected in any suitable carrier known in the art. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

Adjuvants are immunostimulating agents that enhance vaccine effectiveness. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Vaccines are administered in a manner compatible with the dose formulation. By an effective amount is meant a single dose, or a vaccine administered in a multiple dose schedule, that is effective for the treatment or prevention of a disease or disorder. Preferably, the dose is effective to inhibit the growth of a neoplasm. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgment of the practitioner.
Test Compounds and Extracts In general, agents that inhibit cell-cell fusion, that increase cell death or otherwise reduce the proliferation or survival of a tumor-initiating cell of the invention are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have anti-neoplastic activity further fractionation of the positive lead extract is necessary to isolate molecular constituents responsible for the observed effect. Thus, the goal of the extraction, fractionation, and purification process is the careful characterization and identification of a chemical entity within the crude extract that is useful as a neoplasia therapeutic. Methods of fractionation and purification of such heterogenous extracts are known in the art. If desired, compounds shown to be useful as therapeutics are chemically modified according to methods known in the art.

Pharmaceutical Therapeutics

The invention provides a simple means for identifying compositions (including nucleic acids, peptides, small molecule inhibitors, and antibodies) useful as therapeutics for the treatment or prevention of a neoplasia. Accordingly, a chemical entity discovered to have medicinal value using the methods described herein is useful as a drug or as information for structural modification of existing compounds, e.g., by rational drug design. Such methods are useful for screening agents having an effect on a variety of neoplasias associated with viral infections.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of neoplasia. Generally, amounts will be in the range of those used for other agents used in the treatment of other diseases associated with neoplasia.

The administration of a compound for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York).

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Control release dosage forms are known in the art.

As indicated above, the pharmaceutical compositions according to the invention may be in the form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Solid Dosage Forms For Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed. Control release dosage forms are known in the art.

The solid tablet compositions may include a coating adapted to protect the composition from unwanted chemical changes, (e.g., chemical degradation prior to the release of the active anti-neoplasia therapeutic substance). The coating may be applied on the solid dosage form in a similar manner as that described in *Encyclopedia of Pharmaceutical Technology*, supra.

At least two anti-tumor intitiating cell agent or anti-cell fusion agent and an anti-neoplasia therapeutics may be mixed together in the tablet, or may be partitioned using methods routine in the art.

Therapeutic Methods

Agents identified as acting as agents that inhibit cell-cell fusion or that otherwise increase cell death or reduce the survival or proliferation of a tumor-initiating cell are useful for preventing or ameliorating a neoplastic disease. In one therapeutic approach, an agent identified as described herein is administered to the site of a potential or actual disease-affected tissue or is administered systemically. The dosage of the administered agent depends on a number of factors, including the size and health of the individual patient. For any particular subject, the specific dosage regimes should be adjusted over time according to the individual need and the professional judgment of the person administering or supervising the administration of the compositions.

The therapeutic methods of the invention (which include prophylactic treatment) in general comprise administration of a therapeutically effective amount of a composition described herein, such as a anti-neoplasia vaccine of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which neoplasia or hyperplasia may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Methods for Inducing the Differentiation of a Tumor-Initiating Cell

As reported herein, spontaneous cell-cell fusions can initiate and drive the essential aspects of carcinogenesis, including transformation, progression, invasion, metastasis and self renewal. Given that the tumor-initiating cells of the invention are self-sustaining and stem-cell like, it is likely that they can be driven to form a variety of differentiated cell types. Accordingly, the invention provides for the treatment of diseases and disorders associated with a deficiency in cell number. Many diseases associated with a deficiency in cell number are characterized by an increase in cell death. Such diseases include, but are not limited to, neurodegenerative disorders, stroke, myocardial infarction, ischemic injury, or hepatic insufficiency. Injuries associated with trauma can also result in a deficiency in cell number in the area sustaining the wound. Methods of the invention ameliorate such diseases, disorders, or injuries by generating cells that can supplement the deficiency. Such cells are generated by driving the differentiation of a tumor-initiating cell of the invention towards a differentiated phenotype.

In various embodiments, the tumor-initiating cells of the invention are driven to differentiate in vitro using any agent that promotes the differentiation of a stem cell. Exemplary agents include, but are not limited to, any one or more of activin A, adrenomedullin, acidic FGF, basic fibroblast growth factor, angiogenin, angiopoietin-1, angiopoietin-2, angiopoietin-3, angiopoietin-4, angiostatin, angiotropin, angiotensin-2, bone morphogenic protein 1, 2, or 3, cadherin, collagen, colony stimulating factor (CSF), endothelial cell-derived growth factor, endoglin, endothelin, endostatin, endothelial cell growth inhibitor, endothelial cell-viability maintaining factor, ephrins, erythropoietin, fibronectin, granulocyte macrophage colony stimulating factor (GM-CSF), hepatocyte growth factor, human growth hormone, IFN-gamma, LIF, insulin, insulin-like growth factor-1 or -2 (IGF), interleukin (IL)-1 or 8, platelet derived endothelial growth factor (PDGF), retinoic acid, trans-retinoic acid, stem cell factor (SCF), TNF-alpha, TGF-beta, VEGF-A, VEGF-B, VEGF-C, VEGF-D, VEGF-E, VEGF, and VEGF164. Agents comprising growth factors are known in the art to differentiate stem cells. Such agents are expected to be similarly useful for inducing the differentiation of a tumor-initiating cell. In an embodiment, such agents are used to promote differentiation of tumorogenic cells to increase susceptibility to chemotherapeutic agents.

Differentiated cells are identified as differentiated, for example, by the expression of markers, by cellular morphology, or by the ability to form a particular cell type (e.g., ectodermal cell, mesodermal cell, endodermal cell, adipocyte, myocyte, neuron). Those skilled in the art can readily determine the percentage of differentiated cells in a population using various well-known methods, such as fluorescence activated cell sorting (FACS). Preferable ranges of purity in populations comprising differentiated cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Purity cells or their progenitors can be determined according to the marker profile within a population. Dosages can be readily adjusted by those skilled in the art (e.g., a decrease in purity may require an increase in dosage).

Differentiated cells of the invention can be provided directly to a tissue or organ of interest (e.g., by direct injection). In one embodiment, cells of the invention are provided to a site where an increase in the number of cells is desired, for example, due to disease, damage, injury, or excess cell death. Alternatively, cells of the invention can be provided indirectly to a tissue or organ of interest, for example, by administration into the circulatory system. If desired, the cells are delivered to a portion of the circulatory system that supplies the tissue or organ to be repaired or regenerated.

Advantageously, cells of the invention engraft within the tissue or organ. If desired, expansion and differentiation agents can be provided prior to, during or after administration of the cells to increase, maintain, or enhance production or differentiation of the cells in vivo. Compositions of the invention include pharmaceutical compositions comprising differentiated cells or their progenitors and a pharmaceutically acceptable carrier. Administration can be autologous or heterologous. For example, cells obtained from one subject, can be administered to the same subject or a different, compatible subject. Methods for administering cells are known in the art, and include, but are not limited to, catheter administration, systemic injection, localized injection, intravenous injection, intramuscular, intracardiac injection or parenteral administration. When administering a therapeutic composition of the present invention (e.g., a pharmaceutical composition), it will generally be formulated in a unit dosage injectable form (solution, suspension, emulsion).

Formulations

Cellular compositions of the invention comprising differentiated cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the cells (e.g., differentiated cells) utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the differentiated cells or their progenitors. The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

A method to potentially increase cell survival when introducing the cells into a subject is to incorporate cells or their progeny (e.g., in vivo, ex vivo or in vitro derived cells) of interest into a biopolymer or synthetic polymer. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included expansion or differentiation factors. Additionally, these could be in suspension, but residence time at sites subjected to flow would be nominal. Another alternative is a three-dimensional gel with cells entrapped within the interstices of the cell biopolymer admixture. Again, expansion or differentiation factors could be included with the cells. These could be deployed by injection via various routes described herein.

Those skilled in the art will recognize that the polymeric components of the compositions should be selected to be chemically inert and will not affect the viability or efficacy of the differentiated cells or their progenitors as described in the present invention. This will present no problem to those skilled in chemical and pharmaceutical principles, or problems can be readily avoided by reference to standard texts or by simple experiments (not involving undue experimentation), from this disclosure and the documents cited herein.

Dosages

One consideration concerning the therapeutic use of differentiated cells of the invention or their progenitors is the quantity of cells necessary to achieve an optimal effect. In general, doses ranging from 1 to $4 \times 10^7$ cells may be used. However, different scenarios may require optimization of the amount of cells injected into a tissue of interest. Thus, the quantity of cells to be administered will vary for the subject being treated. In a preferred embodiment, between $10^4$ to $10^8$, more preferably $10^5$ to $10^7$, and still more preferably, 1, 2, 3, 4, 5, 6, 7×$10^7$ stem cells of the invention can be administered to a human subject.

Fewer cells can be administered directly a tissue where an increase in cell number is desirable. Preferably, between $10^2$ to $10^6$, more preferably $10^3$ to $10^5$, and still more preferably, $10^4$ differentiated cells or their progenitors can be administered to a human subject. However, the precise determination of what would be considered an effective dose may be based on factors individual to each subject, including their size, age, sex, weight, and condition of the particular subject. As few as 100-1000 cells can be administered for certain desired applications among selected patients. Therefore, dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active stem cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

If desired, cells of the invention are delivered in combination with (prior to, concurrent with, or following the delivery of) agents that increase survival, increase proliferation, enhance differentiation, and/or promote maintenance of a differentiated cellular phenotype. In vitro and ex vivo applications of the invention involve the culture of differentiated cells or their progenitors with a selected agent to achieve a desired result. Cultures of cells (from the same individual and from different individuals) can be treated with expansion agents prior to, during, or following differentiation to increase the number of differentiated cells. Similarly, differentiation agents of interest can be used to generate a differentiated cell from a tumor-initiating cell. Differentiated cells can then be used for a variety of therapeutic applications (e.g., tissue or organ repair, regeneration, treatment of an ischemic tissue, or treatment of myocardial infarction). If desired, differentiated cells of the invention are delivered in combination with other factors that promote cell survival, differentiation, or engraftment. Such factors, include but are not limited to nutrients, growth factors, agents that induce differentiation, products of secretion, immunomodulators, inhibitors of inflammation, regression factors, hormones, or other biologically active compounds.

Delivery Methods

Compositions of the invention (e.g., cells in a suitable vehicle) can be provided directly to an organ of interest, such as an organ having a deficiency in cell number as a result of injury or disease. Alternatively, compositions can be provided indirectly to the organ of interest, for example, by administration into the circulatory system. Compositions can be administered to subjects in need thereof by a variety of administration routes. Methods of administration, generally speaking, may be practiced using any mode of administration that is medically acceptable, meaning any mode that produces effective levels of the active compounds without causing clinically unacceptable adverse effects. Such modes of administration include intramuscular, intra-cardiac, oral, rectal, topical, intraocular, buccal, intravaginal, intracisternal, intracerebroventricular, intratracheal, nasal, transdermal, within/on implants, e.g., fibers such as collagen, osmotic pumps, or grafts comprising differentiated cells, etc., or parenteral routes. The term "parenteral" includes subcutaneous, intravenous, intramuscular, intraperitoneal, intragonadal or infusion. A particular method of administration involves coating, embedding or derivatizing fibers, such as collagen fibers, protein polymers, etc. with therapeutic proteins. Other useful approaches are described in Otto, D. et al., J. Neurosci. Res. 22: 83 and in Otto, D. and Unsicker, K. J. Neurosci. 10: 1912.

In one approach, differentiated cells derived from cultures of the invention are implanted into a host. The transplantation can be autologous, such that the donor of the cells is the recipient of the transplanted cells; or the transplantation can be heterologous, such that the donor of the cells is not the recipient of the transplanted cells. Once transferred into a host, the re-differentiated cells are engrafted, such that they assume the function and architecture of the native host tissue.

In another approach, differentiated cells derived from cultures of the invention are implanted into a host. The transplantation can be autologous, such that the donor of the cells is the recipient of the transplanted cells; or the transplantation can be heterologous, such that the donor of the cells is not the recipient of the transplanted cells. The differentiated cells are then engrafted, such that they assume the function and architecture of the native host tissue. Differentiated cells and the progenitors thereof can be cultured, treated with agents and/or administered in the presence of polymer scaffolds. If desired, agents described herein are incorporated into the polymer scaffold to promote cell survival, proliferation, enhance maintenance of a cellular phenotype. Polymer scaffolds are designed to optimize gas, nutrient, and waste exchange by diffusion. Polymer scaffolds can comprise, for example, a porous, non-woven array of fibers. The polymer scaffold can be shaped to maximize surface area, to allow adequate diffusion of nutrients and growth factors to the cells. Taking these parameters into consideration, one of skill in the art could configure a polymer scaffold having sufficient surface area for the cells to be nourished by diffusion until new blood vessels interdigitate the implanted engineered-tissue using methods known in the art. Polymer scaffolds can comprise a fibrillar structure. The fibers can be round, scalloped, flattened, star-shaped, solitary or entwined with other fibers. Branching fibers can be used, increasing surface area proportionately to volume.

Unless otherwise specified, the term "polymer" includes polymers and monomers that can be polymerized or adhered to form an integral unit. The polymer can be non-biodegradable or biodegradable, typically via hydrolysis or enzymatic cleavage. The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon®, nylon silicon, and shape memory materials, such as poly(styrene-block-butadiene), polynorbornene, hydrogels, metallic alloys, and oligo(ε-caprolactone)diol as switching segment/oligo(p-dioxanone)diol as physical crosslink. Other suitable polymers can be obtained by reference to The Polymer Handbook, 3rd edition (Wiley, N.Y., 1989).

Kits

The invention provides kits for the practice of the methods of the invention. The kit can include, for example, an enriched population of tumor-initiating cells for growth in culture and instructions for use. The cells can be used to practice any of the methods of the invention including drug screening and the generation of models of cancer in mammals.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

This invention is further illustrated by the following examples, which should not be construed as limiting.

EXAMPLES

Example 1

Cell-Cell Exchange In Vitro

The question of whether fusion of normal primary cells, without transgenic alteration, can create allelic imbalances and other molecular repartitionings sufficient to transform these cells into cancer cells was investigated. That is, can cell-cell fusion, in and of itself, lead to carcinogenic cell transformation, without the need to invoke specific gene mutations. If fusion can transform normal cells into cancer cells, then further fusion events between tumor cells or between tumor and host cells may be what drives and sustains cancer progression. To these ends, the ability of primary murine lung fibroblasts (MLF) and murine Lewis lung carcinoma cells (LLC) to undergo cell-cell fusion was investigated in vitro. The cytoplasm of cells was labeled with different colored Qdots® to detect cell-cell exchanges and fusions. These particular constructs, designed for cell labeling in vitro, are taken up in the cytoplasm, by endocytosis, and remain there once internalized. They have been reported not to induce fusion events and to be non-toxic to live cells (Murasawa et al. 2005, Gopalakrishnan et al. 2006). This cytoplasmic marking system was also used in lieu of reporter constructs to minimize interference with cellular chromosome integrity.

In these experiments, high levels of cell-cell exchanges and fusions were observed among murine lung fibroblasts (MLF) cells, among LLC cells, and between MLF and LLC cells following 24 hour culturing (FIGS. 1A-1D). Replicate MLF cultures were labeled with red and green with Qdots, respectively, and co-cultured. Following 24 hours of co-culture the cell population was sorted for double-labeled (red/green) cells. These cells are referred to as "MLF-MLF" cells, as they contain cytoplasmic material from at least two MLF cells, either with the accompanying nuclei (e.g., cell fusion or cell engulfment) or without (cytoplasm transfer only).

The findings demonstrated that spontaneous cell "unions" of these various sorts are frequent in MLF cultures. The sorted cells exhibited morphological features indicative of fusion, including the presence of two or even three nuclei within one cytoplasm. Inspection of the degree of DNA condensation within nuclei indicated that cells often fused while in different phases of their respective cell cycles, confirming that the presence of two nuclei was not a consequence of nuclear division (FIG. 1A, fusion of a prophase cell with an interphase cell). Cytoskeletal-mediated activity analogous to that observed during developmental fusion was also detected, specifically, the extension of filopodia linking fusing cells (FIG. 1A). In a small number of fused cells, an entire cell appeared inside the second cell. Such cells are consistent with what has been described by Overholtzer et al. (2007) as entosis. Countering the idea that cell-cell fusion is a rare event, the level of fusion detected in these cultures was considerable (25.8%±10.4 MLF-MLF, 49.6%±29.2 LLC-LLC, and 16.4%±2.5 MLF-LLC) (FIGS. 1B and 1C).

Additionally, it is noted when these MLF-MLFp25 cells where assayed for the degree of cell-cell exchange within the population using the Qdot double-labeled cell assay described above, an average of 58.8%±0.4% double-labeled cells was detected (FIG. 1D). This observation indicates that the MLF-MLFp25 cell population has, during passage, transitioned to one where cells are uniformly engaged in very high cell-cell exchange activity. This result contrasted with the 25.8%±10.4% detected from the original MLF population and the 49.6%±29.2% detected with LLC cells. Not only were more cell-cell exchanges in the MLF-MLFp25 cell population significantly detected than in the original MLF population, but the tight reproducibility of the results compared to both MLF and LLC showed that MLF-MLFp25 were a highly regulated population of cells.

The results demonstrate that a significant amount of material exchange among cells is ongoing, at least in culture, even over short periods. These data demonstrate that spontaneous cell-cell exchange and fusion of single cells in tissue culture can be a common occurrence. This suggests that when cells in vivo are liberated from the proper three dimensional tissue constraints and extracellular matrix attachments that normally prevent such interactions, the role of cell-cell fusion might also be significant. The prospect that basement membrane detachment might facilitate cell fusion adds an additional mechanistic consideration to the important body of literature reporting that the aberrant three dimensional architecture can modulate carcinogenic conversion (Bissell et al. 2005, Rubin 2006, Wang et al. 1998, Kass et al. 1994, Overholtzer et al. 2007). Taken together, the data suggest cell-cell exchange is a fundamental means of dynamic communication between cells that are allowed to comingle, which can be amplified inappropriately to generate aberrant unstable cells, including overtly fused cells, triggering an overall carcinogenesis program.

Example 2

Cell-Cell Fusion Gives Rise to Transformed Fibroblasts

The isolation of a pure population of double-labeled cells, actively engaged in cell-cell exchange, proved important to establishing the relationship between cell fusion and cell transformation. Given that the sorted fused cells were, for the most part tetraploid, further cell-cell fusions between these cells enabled up to a geometric increase in cell ploidy. In this way, complex cell fusion events (involving three or more nuclei within a cell) that might normally occur over much longer time scales, or not at all, were accelerated. Isolating cells that had fused within the last 24 hours assured the presence of fusion competent cells and also synchronized the cells with respect to that fusion event (once cells fuse there is a relaxation time before cells are again fusion competent).

To characterize this transformation, a detailed investigation into the structural, functional, and molecular response of the population of these double-labeled cells as a function of passage after the initial exchanges was undertaken (FIGS. 2A-2D, 3A and 3B, 4A and 4B, 6A-6D). Double-labeled cell populations were tracked in vitro. LLC-LLC cultures grew similarly to LLC cultures. By passage four (p4), MLF-MLF cultures were growing well and were more resistant to modulations in microenvironmental conditions than the MLFs from which they were derived. A ubiquitous early stage in the generation of the MLF-MLF, MLF-LLC and LLC-LLC fused cells was the presence of multiple nuclei within the cell, i.e. the formation of syncytia and heterokaryons (Harris et al. 1969, Ogle et al. 2005). Although most cells contained two nuclei following the original sort, further culturing lead to subsequent fusions and the accumulation of additional nuclei per cell. In later passages it was not uncommon to detect 5-6 nuclei (e.g. FIG. 2a MLF-MLFp4, MLF-LLCp6). Populations of fused fibroblasts, MLF-MLF, were tracked in vitro for over fifty passages.

Figure 2:
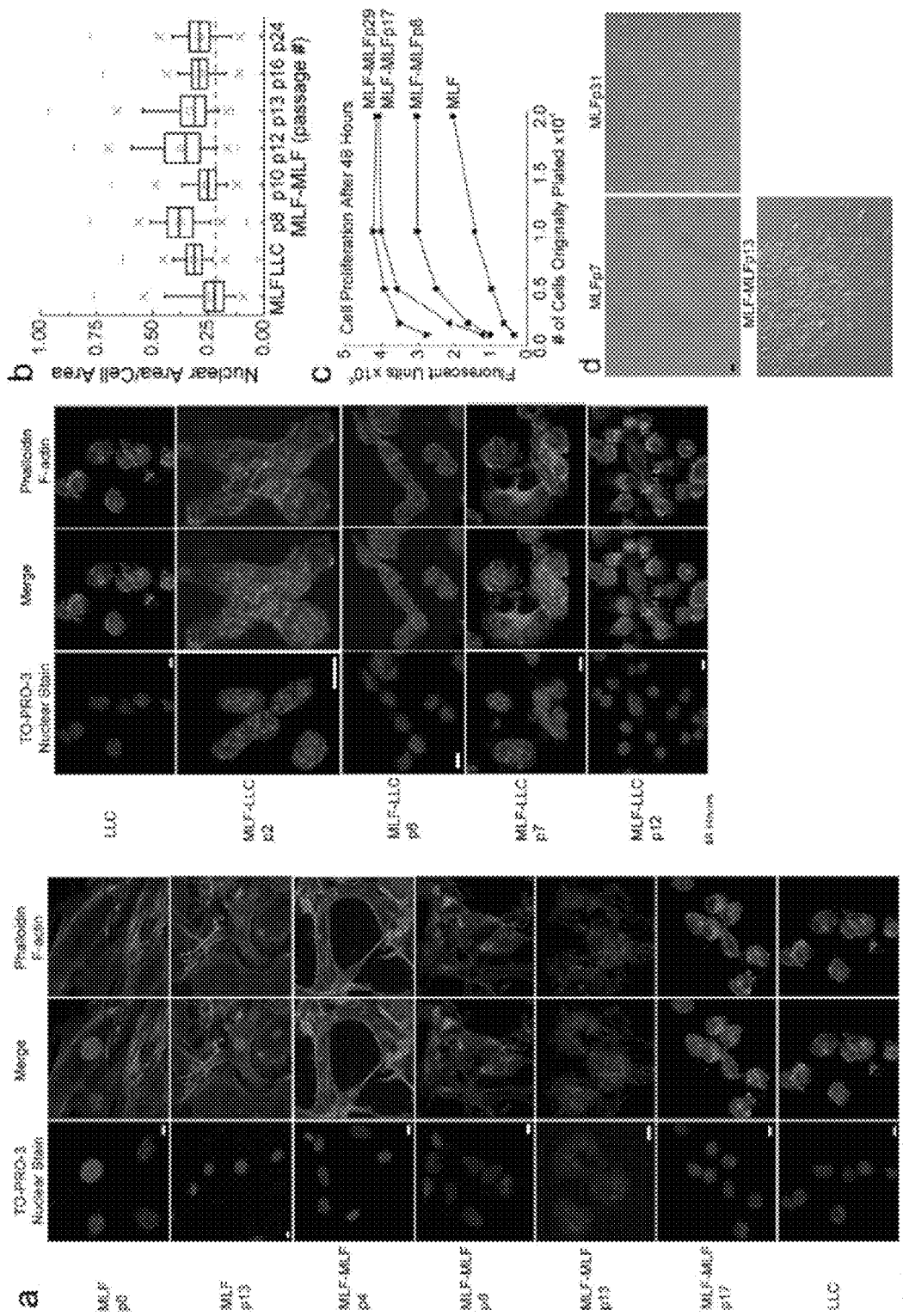
FIGS. 2A-2D show the production of fused cells as function of passage in vitro.

Unlike primary MLF cultures, MLF-MLF cultures grew faster with continued passaging (FIG. 2C). MLF-MLF maintained a flat, adherent "fibroblast-like" morphology up to passage thirteen (p13). At p13 a dramatic shift occurred not only in the form and character of the majority of cells (FIGS. 2A, 2B, 2D), evidenced by cellular and nuclear alterations (FIG. 2A) sweeping structural changes e.g. increased nuclear/cytoplasmic ratios (FIGS. 2A and 2B, loss of filamentous actin (FIG. 2A), and adoption of a rounded, less adherent cell morphology (FIGS. 2A and 2D). These physical changes accompanied alterations in the molecular fingerprint (FIG. 6B), indicating a massive synchronized transformation of the population.

Cells transitioned from an extended and adherent phenotype (and often multinucleate cells) to a spherical, lightly-adherent morphology, reminiscent of stem cell cultures. The population-wide nature of the transformation was in sharp contrast to the well-documented spontaneous transformations frequently noted within murine cell populations, which are focal and occur at very low frequency (e.g., 10 focal transformants per 100,000 NIH-3T3 cells, Chow et al., 1994). Accompanying the changes in size and shape of the emergent cells was a pronounced alteration in the cell cytoskeleton, with the disruption and eventual loss of filamentous actin by passage thirteen (FIG. 2A). This loss of filamentous actin is consistent with the actin disruption that has been observed in cells following tumorigenic conversion (Folger and Pardee 1999).

It is also known that disruption of filamentous actin prevents fusion of macrophages (deFife and Jenney 1999). In the present study, actin disruption may function in an analogous manner by preventing further fusion and/or enhancing an "anti-fusion" or a "fission" process, resulting in the predominately multinucleate cell population giving way to a population of small, round, mononucleate cells (FIGS. 2A, 2B, 2D). As shown in FIG. 2A, the MLF-MLFp17 cells no longer resembled the MLF cells from which they were derived but phenotypically and morphologically resembled the murine epithelial lung tumor (LLC) cells. Similar morphological conversions occurred in the MLF-LLC cells by p12, at which time they were indistinguishable from the original LLC cells. No such morphological transitions occurred in the MLF populations over the more than 30 passages in culture (FIGS. 2A, 2D, and 6A-6D). Without being bound to a particular theory, the striking morphologic transition to epithelial-like mononucleated cells detected for the MLF-MLF cell populations shows that transformations in vivo could easily go undetected, and an essential population-level role in initiating carcinogenesis could be overlooked.

Quantification of the average nuclear area/cellular area for the MLF-MLF cells is shown as a function of passage (FIG. 2B). As observed over p8, p10, p12, p13, p16, and p24, the ratio of nuclear-to-cellular area oscillated with passage, mirroring the chromosome content variations expected from cycles of cell-cell fusions, followed by losses and repartitionings of nuclear material into smaller cells. At later passages, this ratio asymptotes to a value similar to that for LLC cells and is somewhat higher than that for the MLF cells from which they were derived (FIG. 2B).

Example 3

Transformation of Fused Fibroblasts in Culture

Figure 3:
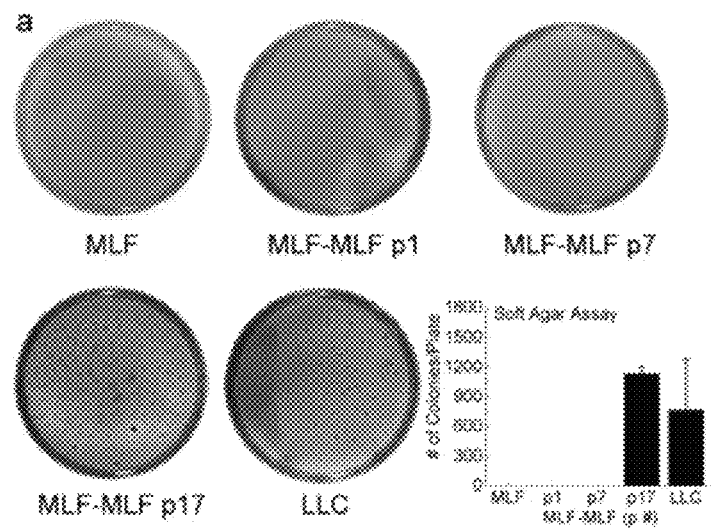
FIGS. 3A and 3B show that fused fibroblasts undergo transformation in vitro.
Figure 3:
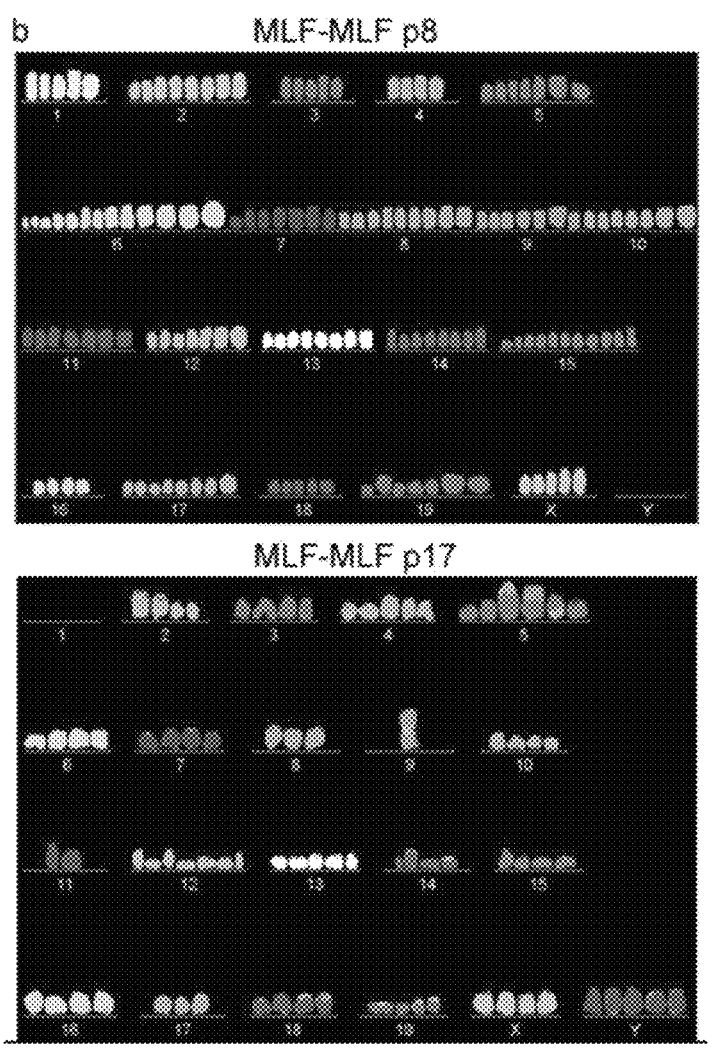
Figure 4:
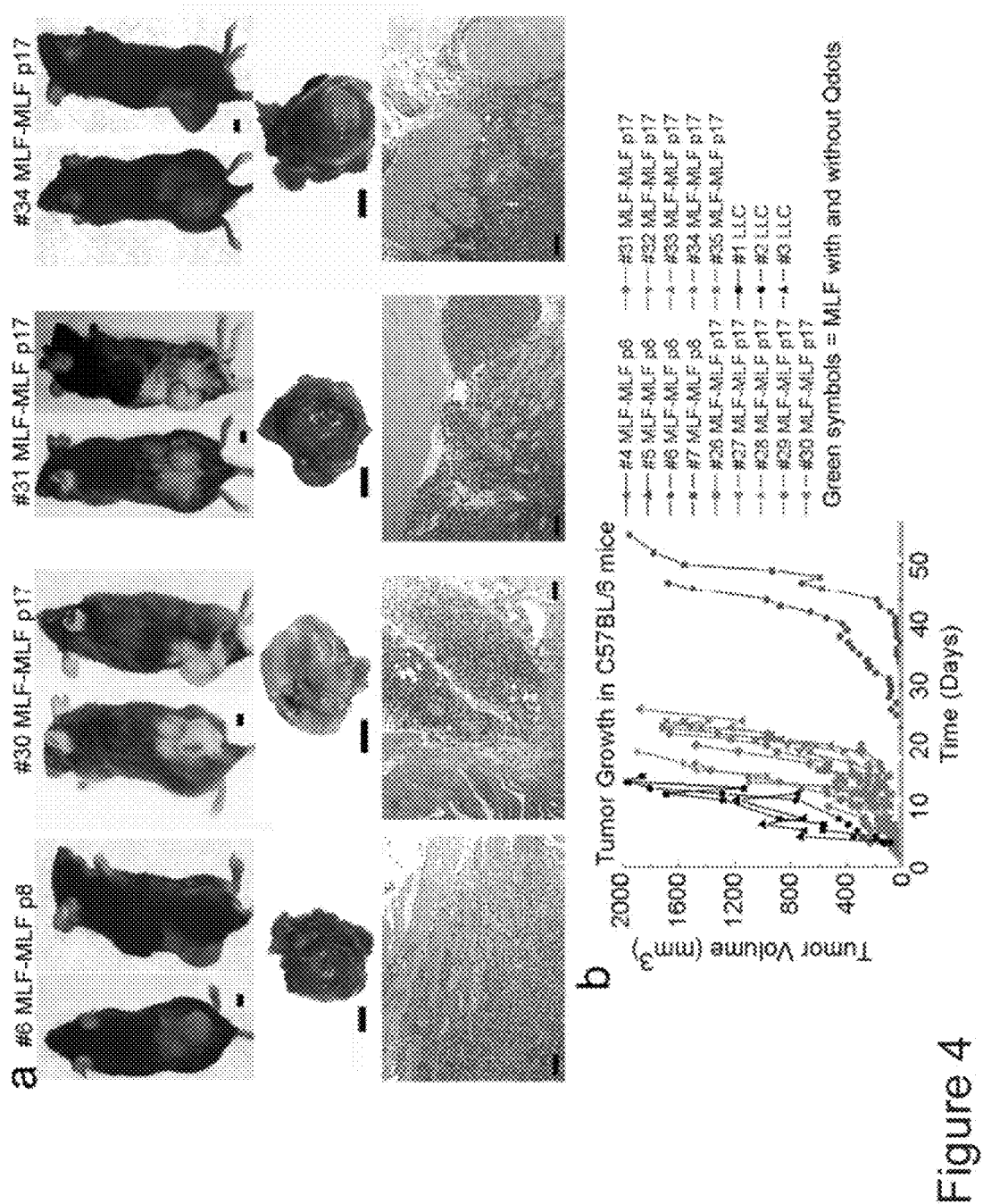
FIGS. 4A and 4B show that fused fibroblasts induce invasive malignant tumors in vivo.

To verify that spontaneously fused fibroblasts had indeed undergone carcinogenic transformation the classic measures of carcinogenic transformation employed by investigators were used to show creation of tumor cells with defined genetic elements (Hahn et al. 1999), the ability of the cells to form colonies in soft agar in vitro (FIG. 3A) and to form tumors in vivo (FIGS. 4A and 4B). In the soft agar assay, no transformed cells were detected in pre-passage thirteen cultures, but a dramatic emergence of a transformed cell population was observed in post-passage thirteen cultures. Additionally, as expected, the normal fibroblast (MLF) populations contained no transformed cells, whereas the lung tumor (LLC) populations contained large numbers of transformed cells. About 60% more cell colonies were measured for the MLF-MLFp17 population than for the aggressive epithelial carcinoma line, LLC (FIG. 3A). This highly tumorogenic phenotype was concurrent with a decrease in expression of CD44 demonstrating that expression of CD44 is not essential to establishment of tumors or growth in soft agar. The MLF-MLF p17 cells also yielded on average about 60% more cell colonies in the soft agar assay than did the LLC cells plated at the same density (FIG. 3A). Paralleling the reduced variance seen in the frequency of cell-cell exchange events among sorted MLF-MLFp25 cells vs LLC cells (FIG. 1D), the variance in ability to form colonies was much reduced for the MLF-MLFp17 when compared to that of the LLC line.

Since the same colony growth assay was used as a measure of transformation efficacy in vitro, these results can be contrasted with the studies using the defined genetic elements, large-T, hTERT and ras, to engineer human cancer cells (Hahn et al. 1999). The MLF-MLFp17 populations demonstrated 1137±66 colonies per 5000 cells plated (approx 23%), whereas the human cells transfected with oncogenic genes yielded approx 150 colonies per 10,000 cells plated (<1.5%). Notwithstanding differential difficulties in achieving transformation in human vs. mouse cells, it remains that the level of transformation attained in these studies—by simply modulating cell population dynamics and isolating naturally fused cells without genetic intervention—exceeded that realized by a strategic transfection of oncogenic genes specifically selected to accomplish that end.

In the Hahn et al., 1999, classic transfection study, the human cells took 60 population doublings in culture post-transfection to obtain the less than 1.5% transformation. Without being bound to any particular theory, events beyond the oncogene transfections, including heightened cell-cell exchanges, assisted in triggering cell destabilization and ultimate transformation. It also heightens confidence that the cell transformation model generated through the amplification of normal cell processes, which lack the introduced mechanistic biases inherent to genetic transfection, is well-positioned to reveal genetic, biochemical, and structural steps involved in the transition of normal cells to cancer cells that remain, to date, not available through preconceived oncogene manipulation alone.

Example 4

Production of Fused Fibroblasts In Vitro, Parallels Cancer-Cell Progression In Vivo Strikingly, MLF-MLF cells were generated in vitro in a manner analogous to the progression of cancer cell populations in vivo. Like spontaneously arising cancer, the spontaneously fused fibroblast populations: transformed (FIG. 3A); developed genomic instability (FIG. 3B); increased aneuploidy (FIG. 3B); acquired chromosome-level aberrations, including losses and gains of homologues and translocations (FIG. 3B); increased cellular proliferation rate (FIG. 2C); and upregulated classic oncogenes, e.g. k-ras, myc and Bcl-2, while downregulating tumor suppressor genes and apoptosis genes, e.g. CDKn2A and p53 (FIG. 6B). RNA and protein studies revealed increases in invasion and metastasis-related genes e.g. MMP-9, CD44 (FIG. 6A) and upregulated angiogenic genes e.g. VEGF (FIG. 6B). All these classic characteristics of cancer developed simply as a function of passage after enrichment of the fused cell population and mimic the progressive development of these same characteristics in vivo during tumor progression. This suggests that many of the observed "hallmarks" of cancer progression (Hanahan and Weinberg 2000) are not dictated by, random mutations, followed by in vivo pressures and selection of cell-level genetic attributes, but can arise, even in 2D culture, as orchestrated, programmed responses driven by cell-cell fusion events.

Along with developing these molecular and behavioral hallmarks of cancer cells, the structure and phenotype of the fused-fibroblasts converged to exhibit standard pathological features used in the diagnosis of lung and other cancers. These included various cell and nuclear size and shape criteria, e.g. the expression of a high and variable nucleus/cell ratio and abnormally sized and shaped nuclei (FIGS. 2A and 2B) (Franklin 2000, Zink et al. 2004). Central to the in vivo carcinogenic process is the onset of genomic instability following cell transformation. As anticipated, mFISH results verified the genomic instability of these cells. All MLF-MLF cultures exhibited aberrant, aneuploid, unstable genomes which progressed to display the type of chromosome-level aberrations and individual karyotypic diversity observed in solid tumors (Vogelstein and Kinzler 2004, Fabarius et al. 2003) (FIG. 3B). Specifically, karyograms of five cells from the MLF-MLFp8 culture exhibited chromosome numbers ranging from 56-143 (haploid 20) and showed gains and losses of specific homologues. For the MLF-MLFp17 culture, karyograms exhibited from 78-86 chromosomes, again with considerable gains and losses of homologues, but now accompanied by translocation-type chromosome aberrations (FIG. 3B). These findings are in line with data from human cancers which are known to exhibit on the order of 60-90 chromosomes per cell (haploid 23). The fact that in this model, MLF-MLF chromosome number per cell increases and then converges to aneuploid values with lesser variance, is consistent with the multiple cell fusions and subsequent repartitioning into smaller cellular contents, as seen in FIGS. 2A-2D. In types of esophageal and colorectal cancers, tetraploid cells are observed as an intermediate step in the development of aneuploid tumor cells (Margolis 2005), which is consistent with cell-cell fusion of diploid cells proceeding and contributing to the development of aneuploidy.

Example 5

Spontaneously-Fused Fibroblasts Induce Malignant Tumors In Vivo

Remarkably, when spontaneously fused, adult fibroblasts that had undergone no genetic manipulation were implanted in mice, aggressive tumors resulted. Both MLF-MLFp8 and MLF-MLFp17 cells induced high-grade malignant tumors (FIGS. 4A and 4B). Parallel control experiments conducted with unsorted, nonfused fibroblasts (MLF) from various passages (MLFp-3, MLFp-2, MLFp0, MLFp9, MLF p19) with and without Qdots®, were conducted, with subcutaneous injection of (FIG. 1a). The MLFp0 populations tested were labeled with either the same concentration of Q dots used for the sort (50 nM), or twice the concentration (100 nM). No tumor growth was detected for any of the mice in these control groups, up to 16 months after cell injection. FIGS. 4A and 4B shows the growth curves and representative photos for MLF-MLFp8 and MLF-MLFp17 tumors. Tumor growth curves for Lewis lung carcinoma (LLC) studies conducted in parallel are shown for comparison. For the MLF-MLFp8 the frequency of tumor incidence was 50% (2/4) with a considerable lag period of about twenty days before tumor growth was detectable. By contrast, 100% (10/10) of animals injected with MLF-MLFp17 had tumors detectable just two days after injection, with their rate of growth increasing to approach that of LLC.

These results are consistent with the high percentage of transformed cells in the p17 population, as detected by the soft agar assay in vitro (FIG. 3A). The fact that MLF-MLFp8 populations, which exhibited no transformed cells in vitro, grew tumors in vivo after an extended lag time, is also consistent with the in vitro results, when it is considered that the additional lag time to tumor appearance (18 days) roughly matched the number of days it took the p8 population to transform in vitro (as p13). The increase in tumor frequency and the much shortened lag period for MLF-MLFp17 demonstrate how the tumorigenic potential of the MLF-MLF population naturally advances in vitro, analogous to the same process observed in tumors in vivo.

Figure 5:
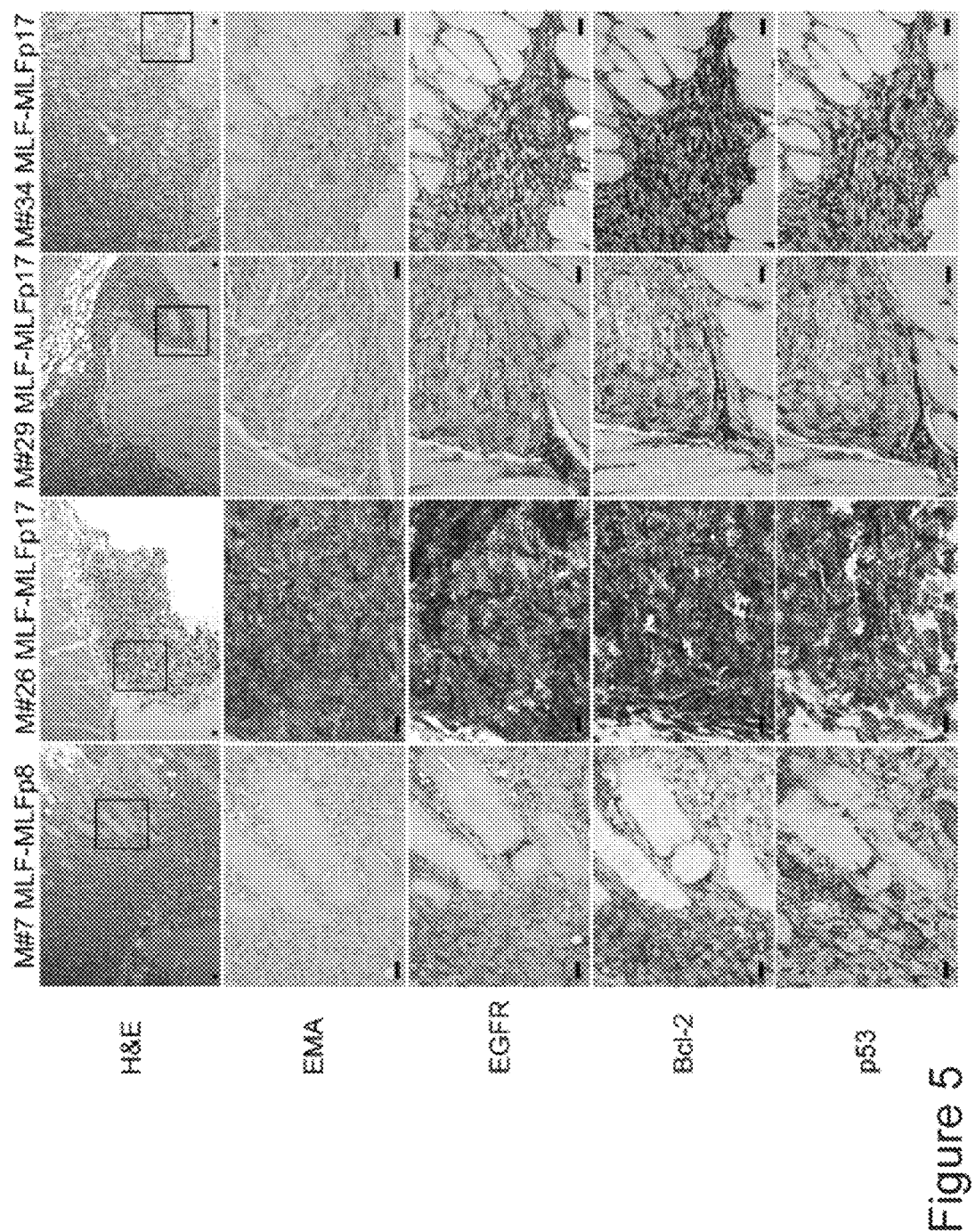
FIG. 5 shows staining MLF-MLF p8 and MLF-MLF p17 with a panel of antibodies for cancer related proteins. Column: H&E; EMA (Epithelial Membrane Antigen), EGFR (Epidermal Growth Factor Receptor), anti-apoptotic proto-oncogene Bcl-2; and tumor suppressor p53. Note absence of EMA in these tumors is taken to be an indicator of their stromal cell origin, while the presence of significant EMA tumor staining from a site in mouse 26 is taken to be an indicator of their epithelial cell origin, although the tumor in mouse 26 originated from the same non-genetically altered lung fibroblasts. Considerable EGFR and Bcl-2 are detected in these tumors. Both these proteins are highly expressed in lung cancers. The black scale bars are 20 μm.

All tumors grown from MLF-MLF p8 and p17 cells were malignant, as demonstrated by their invasion into the adjacent muscle tissue (FIGS. 4A and 4B). In keeping with their fibroblast origin, the tumors appeared histologically comparable to high-grade sarcomas based on cellular organization and a general lack of epithelial membrane antigen (EMA) staining (FIG. 5, mouse 26 (M#26)). Yet surprisingly, malignant cells in distinct regions of p17 tumors stained positive for the carcinoma marker EMA (FIG. 5). Because the injected cancer cells were of stromal origin, without wishing to be bound by theory, this result would suggest that either mesenchymal-epithelial transition (MET) or cell-cell fusions between stromal and epithelial cells in vivo had occurred. This raises again the issue of whether all cancers categorized as epithelial, actually originate from epithelial cells.

Fusion may have significant implications for the observation that cells in carcinomas can express both epithelial and mesenchymal features, and that epithelial mesenchymal transitions, EMT, are observed in tumors (Trimboli et al. 2008). In general, the MLF-MLF tumors were highly proliferative, with little necrosis despite their large size. In contrast to the MLF-MLFp8 tumors, MLF-MLFp17 tumors appeared multilobular as if composed of an aggregate of smaller tumors originating from multiple cell foci (FIGS. 4A and 4B). This observation supports the recent proposition that a defining characteristic of advanced malignancy may be the seeding of local metastases into which the tumor continually expands (Norton and Massague 2006, Enderling et al., submitted).

In keeping with this macroscopic observation, pathological analysis confirmed the existence of multiple distinct sites with different malignant grades in some p17 tumors. Histological sections from both the p8 and p17 tumors exhibited considerable staining for the oncogenic anti-apoptosis protein Bcl-2 and the activated membrane receptor EGFR (FIG. 5). These proteins, elevated in a vast number of tumor types, play central roles in the development and progression of lung and other cancers and are major therapeutic targets (Sithanandam and Anderson 2008, Adams and Cory 2002). The switching on of these proteins further indicates the extent to which MLF-MLF cancers molecularly mimic spontaneously arising cancers, including carcinomas. All the p8 and p17 tumors continued to grow malignant tumors in new animals when serially passaged mouse to mouse (9 times to date) and in all cases malignant tumors developed, indicating self-renewal capability. Despite continued passage (>50 passages) in vitro the transformed MLF-MLF populations remained tumorigenic. Injections of 500,000 MLF-MLFp58 cells yielded tumors in 2/2 mice (Table 1). Invasive cancers consistently developed in the lungs when MLF-MLFp33 cells were administered by tail vein. Even single colonies of about 1000 cells cloned from individual MLF-MLFp25 cells were determined to be tumorigenic in mice over many generations.

Example 6

Orchestrated Regulation of Cancer Genes

Remarkably, the isolation and subsequent culturing of double-labeled cells was sufficient to orchestrate the synchronous carcinogenic cell transformation observed (FIGS. 2A-2D, 3A and 3B), and trigger the synchronized regulation of individual genes, as measured over twenty-seven in vitro passages. This strongly suggests an orchestrated program of gene regulation was turned on in the fused cells—one which provides a window to the carcinogenesis process up to, during, and through transformation. The time-dependent regulation of critical oncogenes and tumor suppressor genes in MLF-MLF cells, from passage four though nineteen is shown in FIG. 6A. A unique pattern in the transcription of these genes was observed. Around p13, dramatic upregulations were observed for the oncogenes myc, k-ras, and Bcl-2, each of which is associated with vast number of human cancers including many lung cancers (Salgia and Skarin 1998) (FIG. 6A). Most prominently, myc expression in MLF-MLF p13 cells was seen to be upregulated 1200-fold over that of MLF cells. myc was, by far, the most differentially regulated of the fifteen genes examined in these cells, with k-ras upregulated 62× and Bcl-2 upregulated 150×. The tumor suppressor gene CDKn2a (p16) (Yaswen and Stampfer 2002, Stampfer and Yaswen 2003, Beauséjour et al. 2003) was oppositely regulated. CDKn2a was significantly downregulated through p13, after which the transcription of this tumor suppressor was essentially shut off (FIG. 6A) and remained off (observed through p27). This is consistent with the fact that CDKn2A is a critical tumor suppressor that becomes methylated and silenced in cancers including LLC (FIG. 6A).

In addition to the time-dependent up- and downregulation of oncogenes and tumor-suppressor genes observed, upregulation of the major tumor angiogenesis factor, VEGF (vascular endothelial growth factor) (Ferrara et al. 2007, Hlatky et al. 1989) was demonstrated. As was the case for the oncogenes examined, VEGF exhibited maximal upregulation around p13. When additional genes prominent in tumor invasion and metastasis were considered, these were also found to be upregulated in a time-dependent manner similar to VEGF and the set of oncogenes investigated (FIGS. 6A and 6B). It is noteworthy that although the classic cancer-related genes investigated demonstrated a marked differential in transcription around p13, this was not the case for all other genes examined. It may be concluded the differential regulation in these cultures at p13 was not a generalized, non-specific response of the cell population, but rather reflected the integrated molecular fingerprint of the transformation event. The culture model may thus offer a means of characterizing and dissecting the transformation process in a time-dependent manner up to and through cell transformation.

The time-dependent pattern of gene transcription observed further underscores the fact that spontaneously fused fibroblasts, under high density conditions, undergo a carcinogenic program which includes the up-regulation and down-regulation of genes analogous to that occurring in human and murine cancer cells in vivo. Invasion and metastasis genes investigated included: CD44 a membrane glycoprotein central in cell homing and adhesion (Sackstein et al. 2008); osteopontin (OPN, SPP1) a ligand of CD44 upregulated in lung, breast, colorectal, ovarian, melanoma, and other cancers and correlated with metastatic potential (Coppola et al. 2004); and the matrix metalloproteinase MMP9, whose elevated expression has been implicated in increased invasion, progression, metastasis and decreased patient survival, across a large spectrum of cancers and, importantly, is also a ligand of CD44 (Desai et al. 2007). Of particular importance with respect to the studies herein, CD44, OPN and MMP-9 are also involved in normal cell-cell fusion processes during development. MMP-9 protein expression increased in MLF-MLFp13 cells, and in parallel with the mRNA regulations, increased protein expressions for CD44 and OPN were also observed (FIGS. 6A-6D). Transcription of CD44 was noted to be upregulated 24-32 fold at p12. CD44 is of particular interest, not simply due to its involvement in tumor metastasis, but because it has also been determined to be a marker for cancer stem cells in breast, prostate, colon (Fillmore 2008 says as few as 100 CD44+/CD24/low/ESA+ cells make tumors), and head and neck tumors (Prince et al. 2007) also normal hematopoietic stem cell (Sackstein et al. 2008). Interestingly, CD44 also plays an integral role in the normal process of macrophage cell fusion (Cui et al. 2006). Vignery's lab has demonstrated that CD44 is highly and transiently expressed in macrophages under fusogenic conditions (Sterling et al. 1998).

On the other hand, osteopontin has been shown to prevent macrophage fusion (Sterling et al. 1998), suggesting that fusion may be a tightly-controlled process targeted to specific situations or times. In the MLF-MLF passages osteopontin transcription demonstrated periodic upregulation as a function of passage, in contrast to the essential lack of osteopontin transcription seen in all of the MLF passages. The regulation of OPN expression (observed out to MLF-MLF p33) expression provides information as to the dynamics of ongoing cell fusions during and beyond transformation. While MMP9 is well-known to be elevated in lung cancers (including LLC, FIGS. 6A-6D) and is correlated with poor clinical prognosis, it happens it is also highly expressed in both myocytes, formed by myoblast fusion, and in osteoclasts, formed by macrophage fusion (Pratap et al. 2005). Consistent with the observation of elevated MMP9 in cells formed by fusion, MMP9 levels were low in the primary fibroblasts (MLFs) but high in fused fibroblasts by passage 17 (FIG. 6B). Without wishing to be bound by theory, it is likely that the elevated MMP-9, CD44, and OPN expression detected in tumor populations, in metastatic cancer cells, and in cancer stem cells are all connected with an ongoing cell-cell exchange and fusion process occurring during carcinogenesis and tumor progression.

Example 7

Cell-Cell Fusion Gives Rise to Cancer Stem Cells

Figure 7:
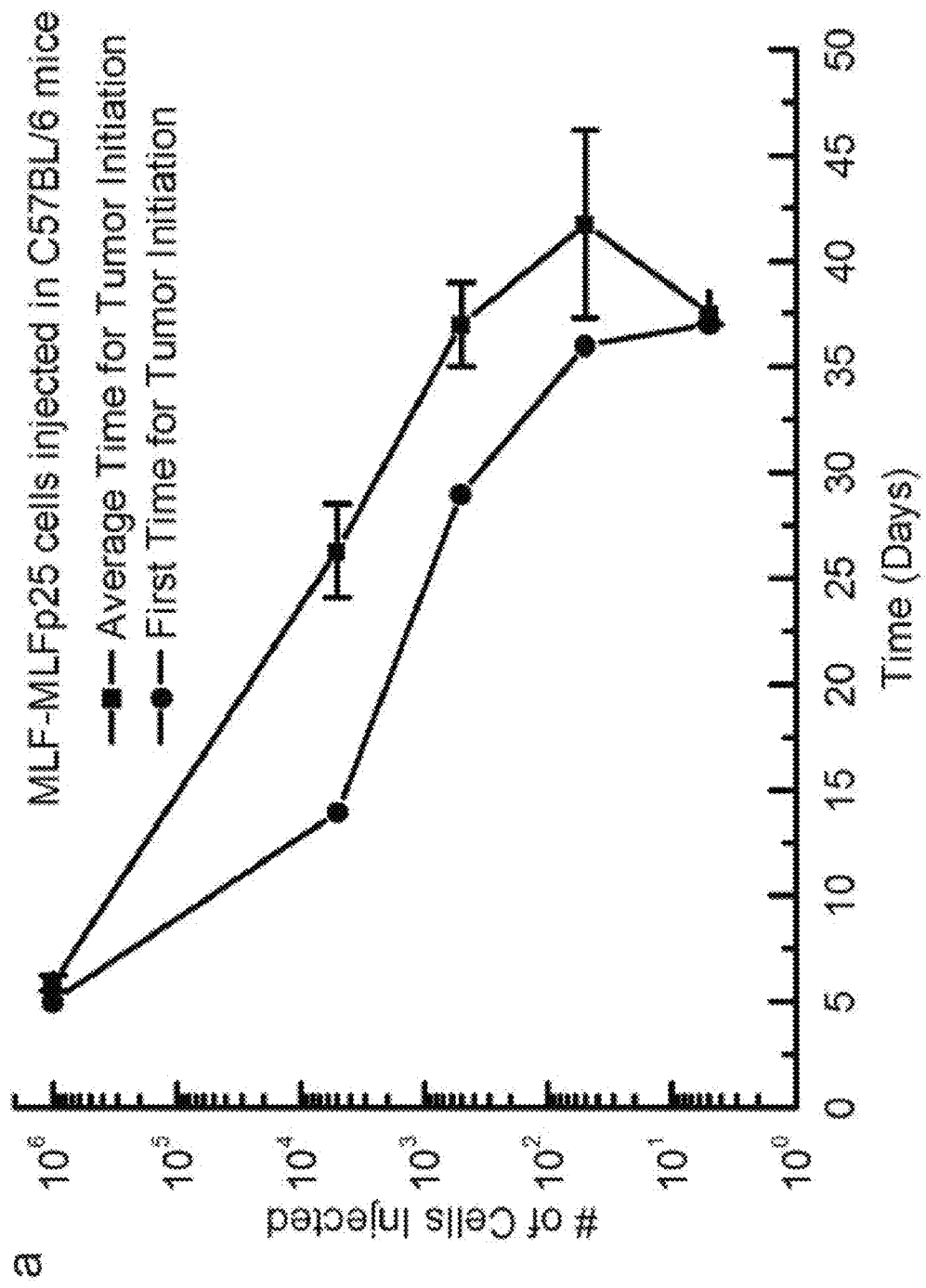
FIGS. 7A-7D shows the results of in vivo dilution assay to detect % of functional cancer stem cells in the MLF-MLF population (p25 cells) by measuring tumor growth in immune competent mice. Various numbers of MLF-MLF p25 cells were injected into p25 competent mice to promote tumor formation.
Figure 7:
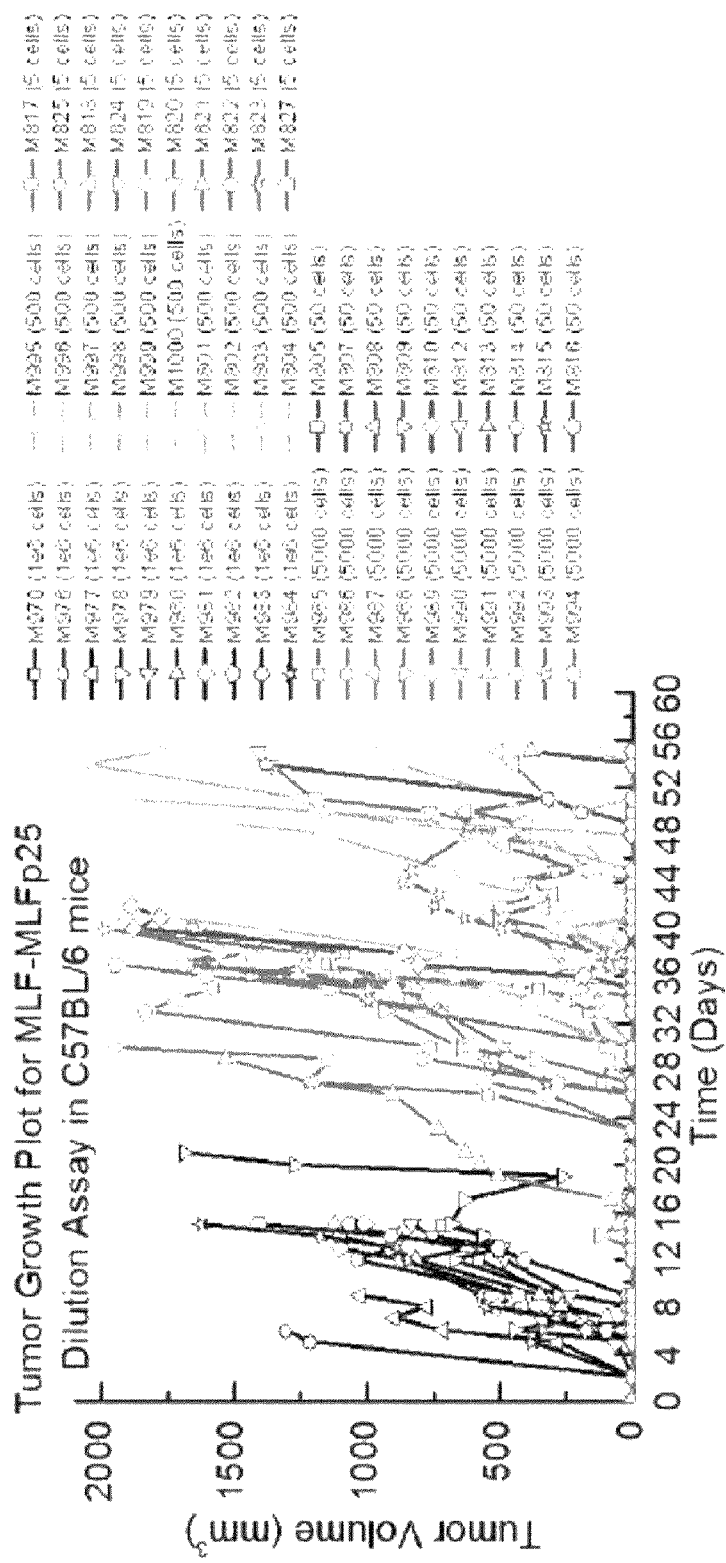
Figure 7:
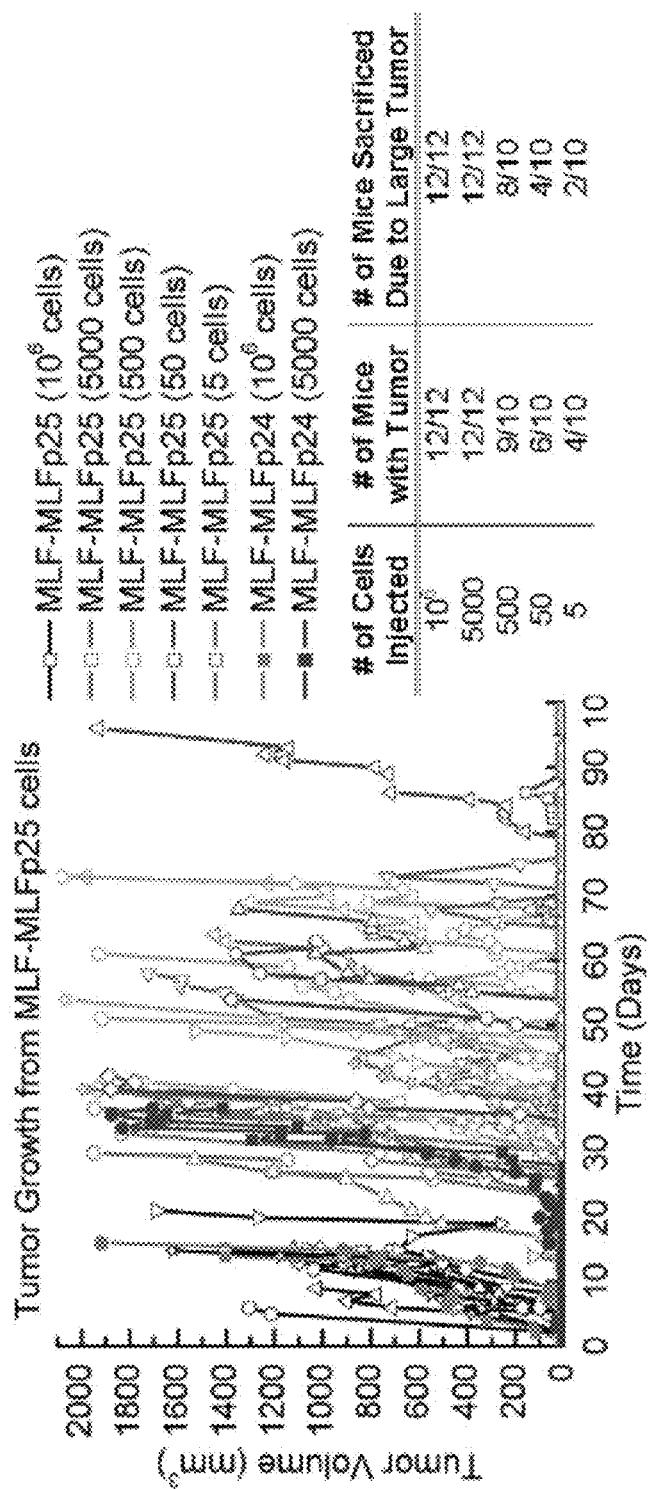
Figure 7:
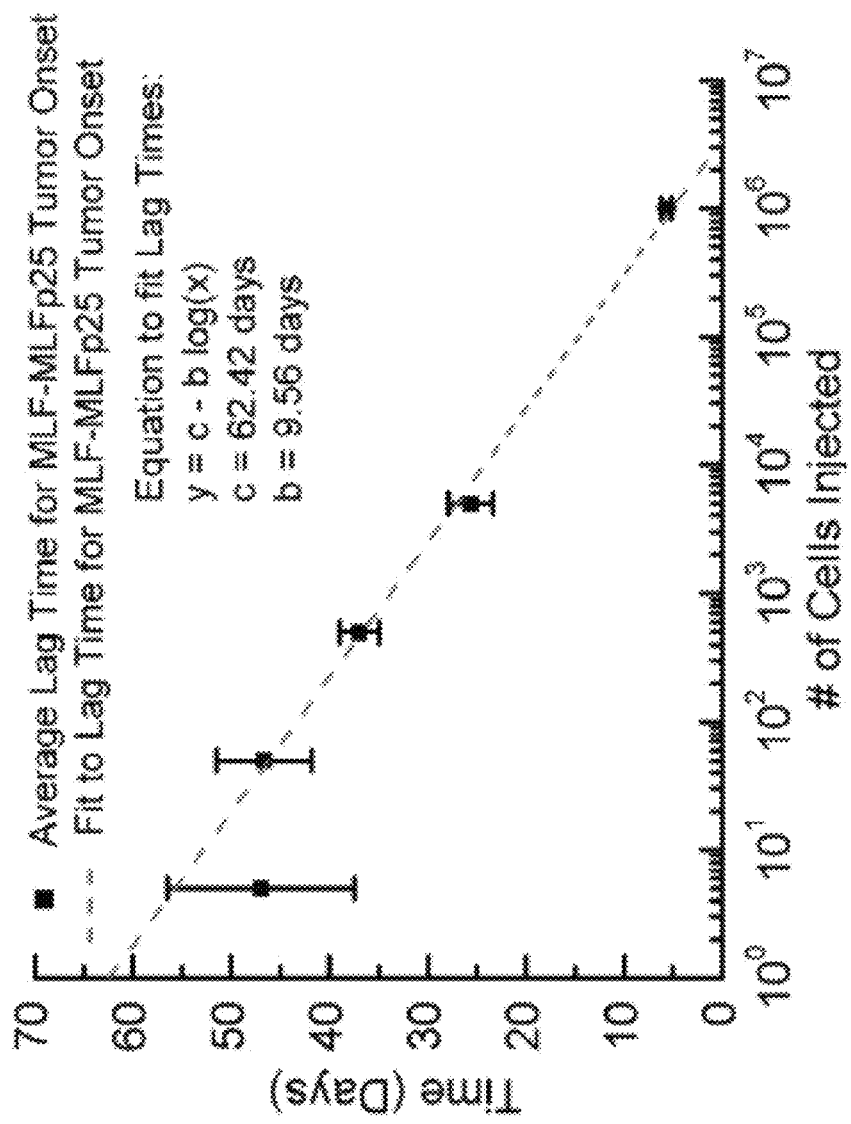

Fused MLF cells were tested for their ability to form cancer stem cells (CSCs). Without being bound to any particular theory, it was hypothesized that the intercellular exchanges and genomic mixing between fused MLF cells creates cancer stem cells (CSCs). As a functional test for CSCs, varying numbers ($10^6$, 5,000, 500, 50, and 5) of MLF-MLFp25 cells were injected in mice to determine the number of cells necessary to initiate tumor growth (FIGS. 7B and 7C). As a departure from standard assays that attempt to determine the potency of cancer populations by first sorting for a series of cell surface markers (e.g. CD44+/CD24$^{-/low}$/ESA+)[70] and then injecting various dilutions of cells expressing those markers, MLF-MLFp25 cells were not pre-selected for markers. Even so, it was demonstrated that 5 MLF-MLFp25 cells were sufficient to produce malignant invasive tumors. It is believed that this is the lowest number of cells found to successfully produce tumors in such assays, and that the ability to produce tumors from this few cancer cells without any pre-selection for surface markers is unprecedented. These results support the characterization of these cells as cancer stem cells.

The number of injected MLF-MLFp25 cells vs the lag time before tumor detection was plotted (FIG. 7B). The cell injection number ($10^6$, 5,000, 500, and 50) versus lag time is a straight line on a log plot ($R^2=0.997$). Aside from affirming the accuracy of the dilutions, this result demonstrated a new finding—that the individual CSCs grew at the same rate independent of number injected. This result suggests CSCs act more or less identically and independently in vivo over more than five orders of magnitude of injection sizes, supporting the assertion the cells are executing an orchestrated program of action. This result is also consistent with the observation in the cell fusion assays that MLF-MLFp25 cells are a tightly regulated population of cells, as indicated by the close reproducibility of the results (FIG. 1D). Using the plot of the number of injected MLF-MLFp25 cells vs the lag time before tumor detection to extrapolate back to one cancer stem cell, it is estimated that such tumors would be detectable approximately 62 mouse days following the creation of the first cancer stem cell. If human tumors were first detected at the same size this period would translate to roughly six human years, a period fairly consistent with time scales derived from human cancer epidemiology. Furthermore, plotting the growth rates of tumors as function of injection size (shown in FIGS. 7A and 7D) showed that the MLF-MLF cells retained potency independent of injection size. Without being bound to a particular theory, this observation suggests that, once created, the fused cells can independently execute cancer growth programs. One important dependence on injection count was noted. Despite the fact that all cells were injected subcutaneously, tumor growth for 5 cells was preferentially internal, and produced more invasive and metastatic tumors overall. Table 1 summarizes the data for all the subcutaneous tumor injections of MLF-MLF and of MLF cells to date. No tumor growth was detected for any of the MLF cell injections in general, in two instances animals injected with MLF-MLFp4 cells eventually developed internal tumor growth in the spleen after 482 days. In sum, transformation of the MLF-MLF cell population resulted in a high fraction of functional cancer stem cells as evidenced by the fact that 5 cells, unsorted for stem cell surface markers, induced tumor growth. In contrast, even sixteen months after injection of MLF passages in vivo, no tumors have been detected in any of the animals.

TABLE 1

| Cells Injected | Tumors |
| --- | --- |
| MLFp-3 | 0/10 |
| MLFp-2 | 0/10 |
| MLFp0 with 50 nM Qdots | 0/5 |
| MLFp0 with 100 nM Qdots | 0/5 |
| MLFp9 | 0/3 |
| MLFp19 | 0/5 |
| MLF-MLF p4 | 2/10* |
| MLF-MLFp8 | 2/4 |
| MLF-MLFp17 | 10/10 |
| MLF-MLFp24 ($10^6$ cells) | 2/2 |
| MLF-MLFp24 (5000 cells) | 2/2 |
| MLF-MLFp25 ($10^6$ cells) | 10/10 |
| MLF-MLFp25 (5000 cells) | 10/10 |
| MLF-MLFp25 (500 cells) | 8/10 |
| MLF-MLFp25 (50 cells) | 4/10 |
| MLF-MLFp25 (5 cells) | 2/10 |

TABLE 1-continued

| Cells Injected | Tumors |
| --- | --- |
| MLF-MLFp35 | 2/2 |
| MLF-MLFp58 (500,000 cells) | 2/2 |

*No subcutaneous tumors. Only internal tumor burden detected in the spleen 482 days after cells injected.

Example 8

Primary Human Fibroblasts for Tumor Initiating Precursor Cells and Progeny

Primary normal human fibroblasts were obtained and grown in culture using the methods used to generate tumor-initiating mouse fibroblasts. Primary human cells were observed to undergo the same program of cell fusion and cell fission to release single nucleate cells in a time frame similar to mouse fibroblasts.

Example 9

Cell-Cell Fusion Observed In Vitro

Figure 8:
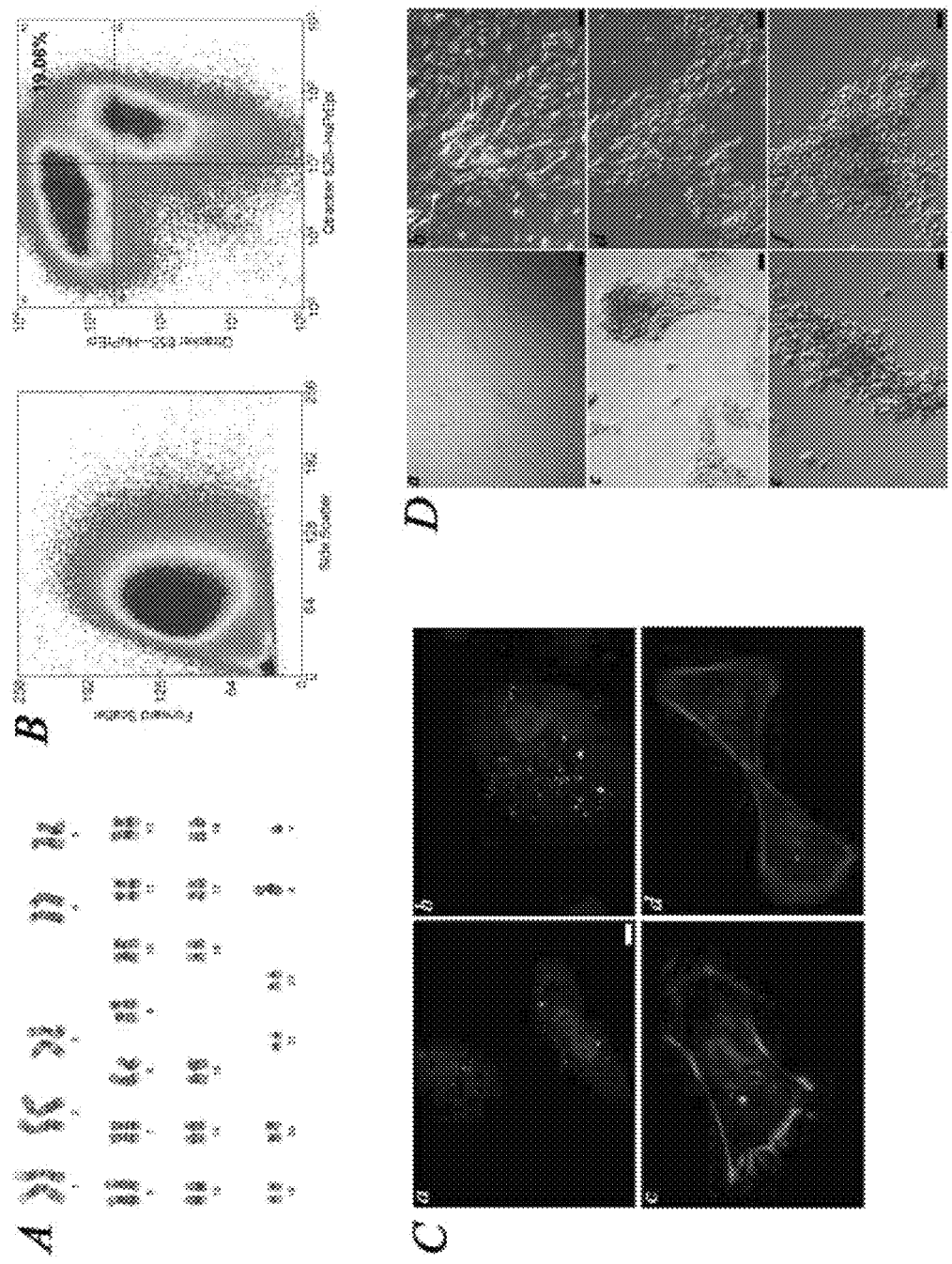
FIGS. 8A-8D demonstrates that human prostate epithelial cell populations undergo cell-cell fusion and fused human prostate epithelial cells are transformed.

Replicate cultures of primary human prostate epithelial cells displaying a normal karyotype (FIG. 8A), were separately labeled with either green (Qtracker 525) or with red (Qtracker 655) quantum dots. The labeled cells were then co-cultured for 24 hours. Following this co-culture period, the cells were sorted into three distinct subpopulations: a double-labeled green-red subpopulation, a single-labeled green subpopulation; and a single-labeled red subpopulation (FIGS. 8A-8D and 9A-9C). Sorting of the double-labeled cells provided a means to isolate a subpopulation of cells that had topologically merged and undergone horizontal exchange of cellular material, removing from the final isolate cells that had not actively exchanged over the last 24 hrs. Red and green Q dots along with double nuclei within a single cytoplasm were observed in confocal images (z-stacks) of representative cells in the double-labeled subpopulation several hours after the cell sort (FIG. 8C). Cells containing both red and green Q dots were observed, and among these, cells containing two nuclei in different cycle phases. The appearance of aberrant, multinucleate cells following sorting and isolation was interpreted as heralding the onset of abnormal nuclear transfers, cell engulfments, and/or cell fusion events presaging final carcinogenic conversion. Notably a significant fraction of the original primary population was seen to participate in exchange activity during a 24 hr period. Approximately 19% of the cells were identified by the sort as double-labeled, whereas 81% were identified as single-labeled (FIG. 8B).

Results from investigations with murine fibroblasts selected for active exchange were subcultured at a moderately high density, continued interactions between the cells could lead to a state of "population instability", resulting in carcinogenic transformation and the emergence of potent cancer cells. No such conversion was observed under the same culture conditions without prior selection for exchange activity. For the current studies, primary human epithelial cells were sorted and cultured following the methodology developed for the murine investigations. The double-labeled and single-labeled epithelial subpopulations were cultured and processed in parallel following the sort. The post-sort double-labeled cells, Epi-Epi p0, grew in vitro and were passaged twice (to Epi-Epi p2) before growth arrest. This was followed by a widespread alteration of cell morphology and of population organization overall. A range of varied cell shapes from extremely elongated to spherical were present. The monolayer character of the original epithelial culture was lost, with cell overgrowth evident, and three-dimensional (3D) colonies formed networks and connected via separate elongated cells and extended cellular processes. Individual linking cells were seen to span the distance between colonies (FIG. 8D). In contrast the control, single-labeled cell populations grown in parallel, did not demonstrate an abrupt transition in growth pattern, did not form 3D structures, and continued to propagate in culture for one additional passage (to Epi p3) beyond that of the Epi-Epi cells.

Example 10

Generation of an Animal Model of Metastatic Cancer

Metastatic animal models of disease are difficult and incredibly time consuming to establish. Typically, the time for the development of metastases exceeds the lifespan of a mouse (2-3 years). Moreover, the cost of maintaining animals for such an extended period of time is prohibitive. The use of highly tumorogenic cells of the invention allows for the reliable generation of metastatic tumors in mouse, rat, and other animal models. Moreover, using enriched populations of highly metastatic cells, a known and reproducible number of cells can be implanted in each animal to allow for comparisons between animals.

Primary mouse fibroblasts are cultured to generate an enriched population of tumor initiating cells. Highly tumorogenic cells are injected into immune competent mice or non-immune competent mice (e.g., nude mice, irradiated mice). Mice are monitored for the development of tumors at sites remote from the injection site.

Figure 9:
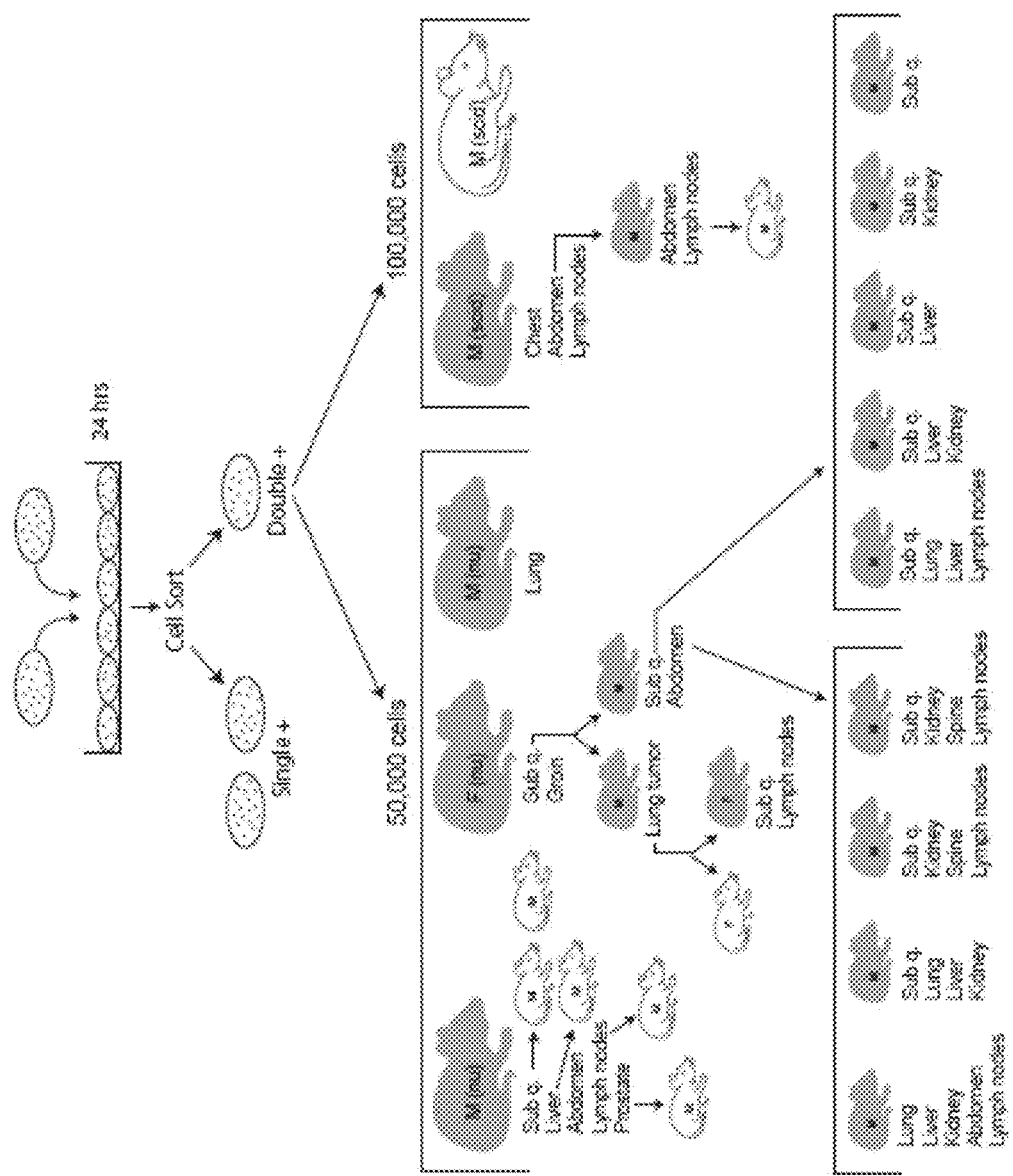
FIG. 9 depicts passage history for human prostate cancer cells in vitro and the first three generations in vivo. Schematic depicts primary prostate epithelial cells labeled with green (Qtracker 525) or red (Qtracker 655) quantum dots mixed in culture (24 hr), then sorted for the doubled-labeled cell population (Epi-Epi). Either 50,000 or 100,000 dual-labeled cells were implanted subcutaneously in adult nude or SCID mice. The description of tumor site (e.g. prostate, lung, lymph nodes, etc.) along with mouse type is given. Serial implants of tumor fragments mouse-to-mouse are depicted using the smaller mouse symbols. Arrows emanate from the tumor type transplanted. Shading indicates sacrificed animal due to tumor burden. To date, tumors have been serially passaged through eight generations of mice with tumor burden developing at multiple sites, attesting to the sustained tumorigenic capacity of these cancers.

Immunocompromised mice were subcutaneously injected with either control (Epi) or the transformed (Epi-Epi p2) cells. FIG. 9 shows a schematic of the fate of nude and SCID mice subcutaneously injected with the transformed (Epi-Epi p2) (50,000 cells or 100,000 cells, respectively). All mice injected with Epi-Epi p2 cells developed malignant cancers. As is characteristic for human prostate cancers, the initial tumor growth was slow. The time of sacrifice was determined by the physical condition of each individual animal rather than the size of any apparent tumor.

For standard tumor models, following the subcutaneous injections of cancer cells, tumors typically develop as subcutaneous masses at the injection site. Interestingly, when Epi-Epi p2 cancer cells were injected minimal or often no tumor developed at the site of injection. Instead, an unexpected ability of the tumor cells to migrate away from the implant site and metastatically colonize internal sites was observed. Tumors grew at orthotopic and metastatic sites typical for prostate cancer, including prostate, bone, liver, lung, and lymph nodes.

Figure 10:
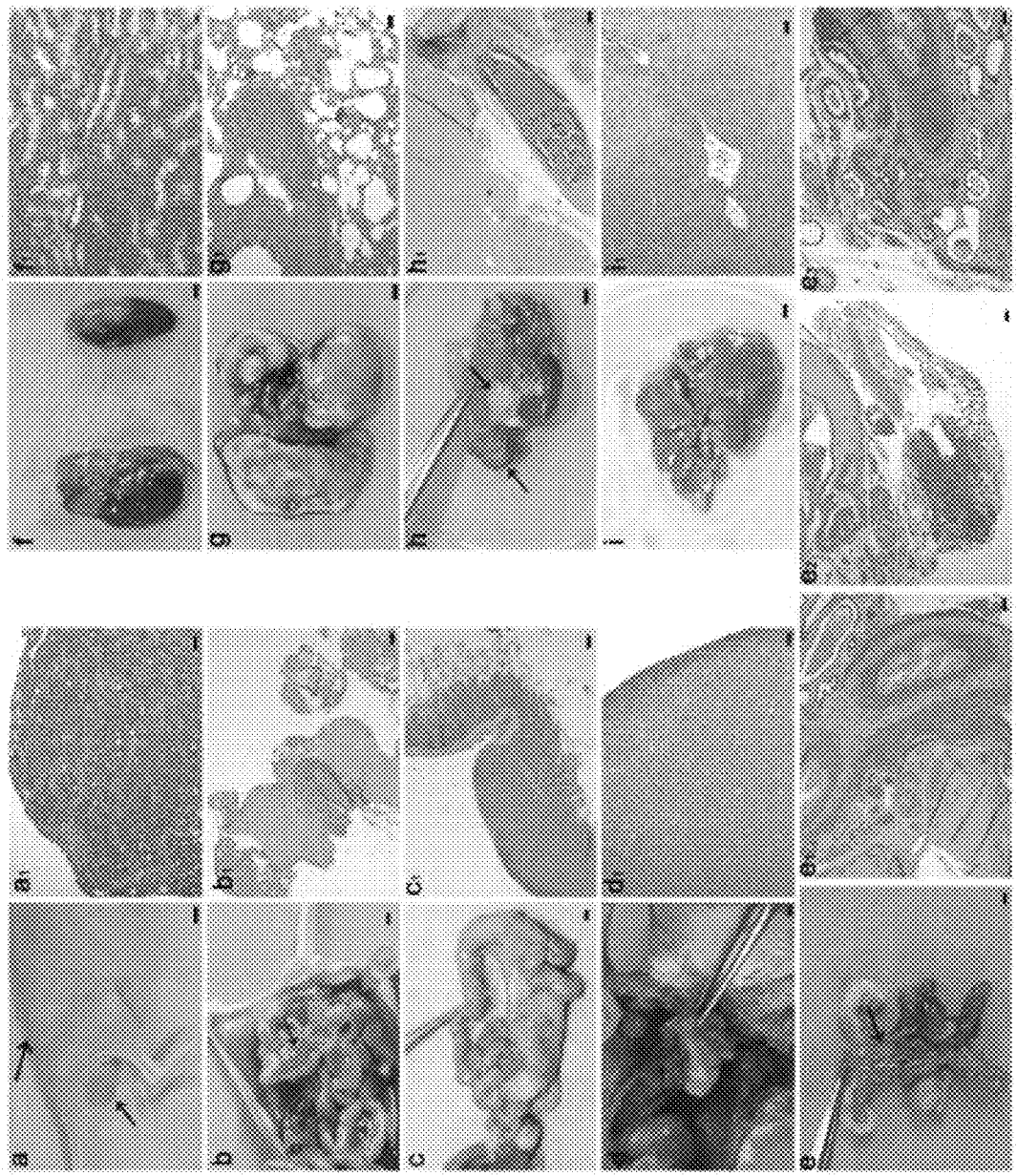
FIG. 10 depicts tumor tissue with respective histology.

In a nude mouse injected with 50,000 cells, a measurable slow-growing subcutaneous tumor (392 mm$^3$ in 29 days) did appear. But, even in this case, the tumor developed not at the site of injection (caudally at the dorsal midline), but rather in the genitourinary area (FIG. 10). A second nude mouse, also injected with 50,000 cells from the same cell aliquot, developed very minimal tumor at the site of injection yet displayed widespread internal tumor dissemination. This animal exhibited cancer in the lymph nodes, near the right kidney; and had a liver metastasis, but most notably, cancer was present in the prostate area and the prostate itself (FIGS. 9, 10, and 11A-11E). The fact that human prostate cancer cells homed to the normal uninjured mouse prostate after subcutaneous injection in the back of the animals, demonstrates a capability extending well beyond homing to sites of injury and may be reminiscent of that seen during embryogenesis and development. Without being bound to any particular theory, this result also points to the conservation between mouse and man of a mechanism driving the homing of these cells to internal sites.

Having established that these transformed prostate epithelial cells, Epi-Epi p2, were indeed highly carcinogenic and demonstrating extraordinary homing ability, it was important to determine if the cancer populations had the ability to perpetuate tumor growth indefinitely. To test this, tumors were passaged in vivo, animal to animal, over eight generations to date. Just as 100% of the mice injected with the transformed cells developed malignant tumors, the in vivo serial passaging of tumor fragments (1 mm$^3$) over generations also resulted in 100% of the animals developing malignant cancers (FIG. 9). To date, all tumor fragments passaged, regardless of the site of excision (e.g. prostate, lymph node, etc.), grew tumors in recipient immunocompromised animals. As expected, parallel studies with wild-type C57B16 mice demonstrated no tumor growth. The tumors exhibited patterns ranging from well-differentiated and glandular to more primitive and stem-cell-like (FIGS. 10 and 11A-11E). The majority displayed a more primitive morphology. In certain instances such variation in morphology was displayed over different regions within the same tumor mass. Taken together these results demonstrate a capacity of these cells to self-renew and to variably differentiate in vivo, extending on the observation that sustained self-renewal capacity observed for murine cancer cells generated by similar methods.

Analogous to the findings seen for injected cancer cells, subcutaneous implantation of tumor fragments also resulted in homing of the cancers to internal sites. The subcutaneous implantation of a tumor fragment did not guarantee subcutaneous tumor growth. Although some tumor implants did result in subcutaneous tumor growth, these tumors were also accompanied by cancers in the prostate and the prostate area, bone, lung, liver, kidney, and lymph nodes (FIGS. 9 and 10). Prostate cancer is well known to metastasize to bone, lymph nodes and, to a lesser extent, lungs and liver. Of patients with metastatic disease, about 50% have lung and about 25% have liver metastasis. Clinical prostate cancer metastasizing to the kidney is rarer, although known to occur.

Figure 11:
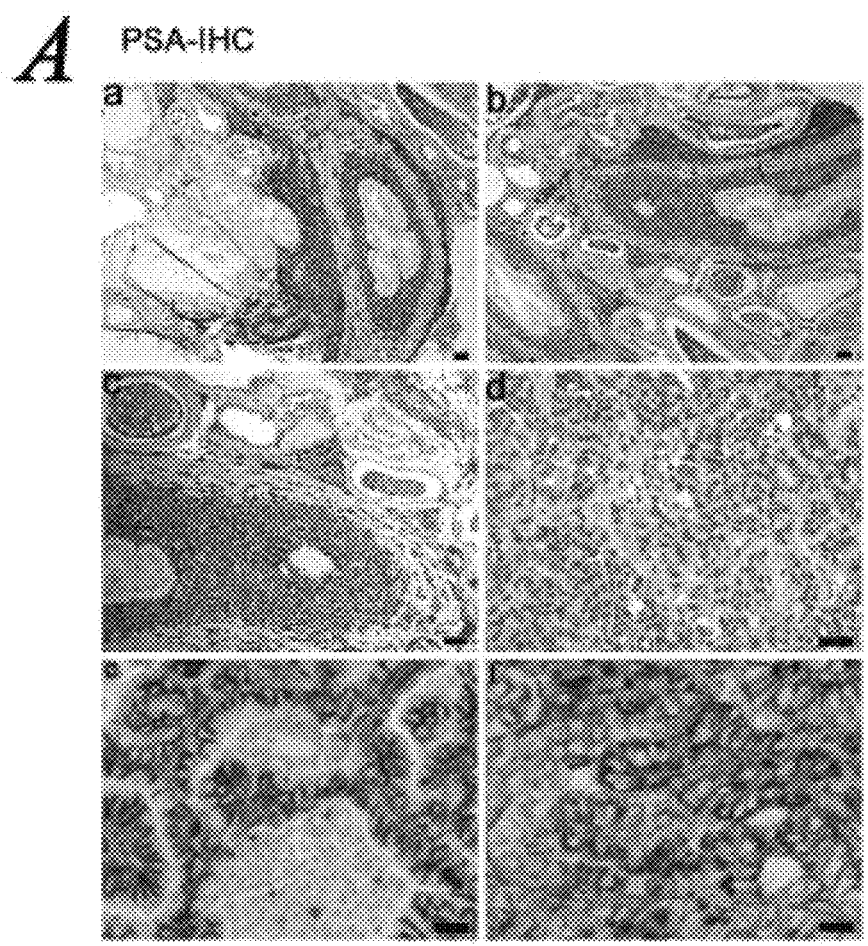
FIGS. 11A-11E demonstrate that PSA detection confirms human prostate cancer in a mouse model.
Figure 11:
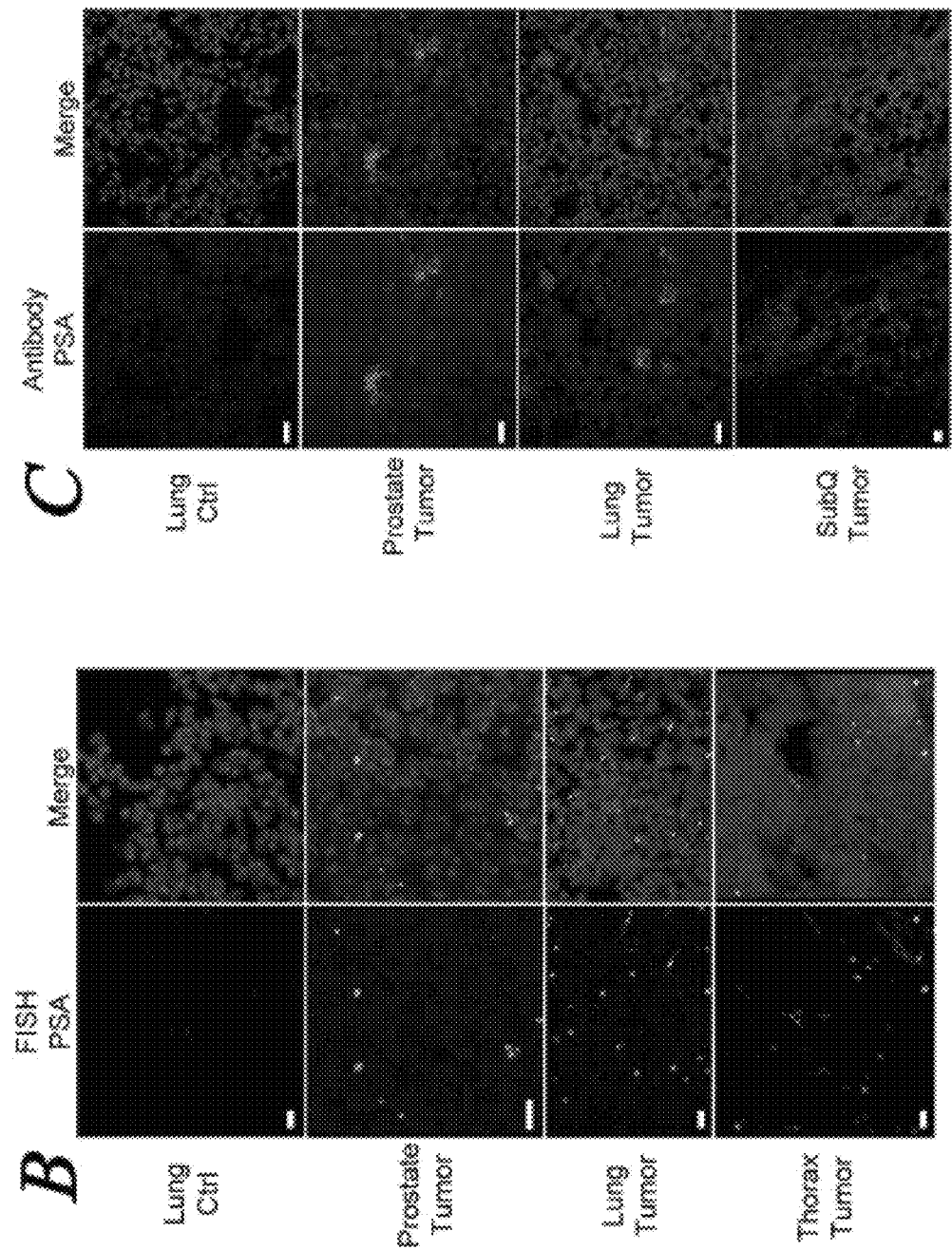
Figure 11:
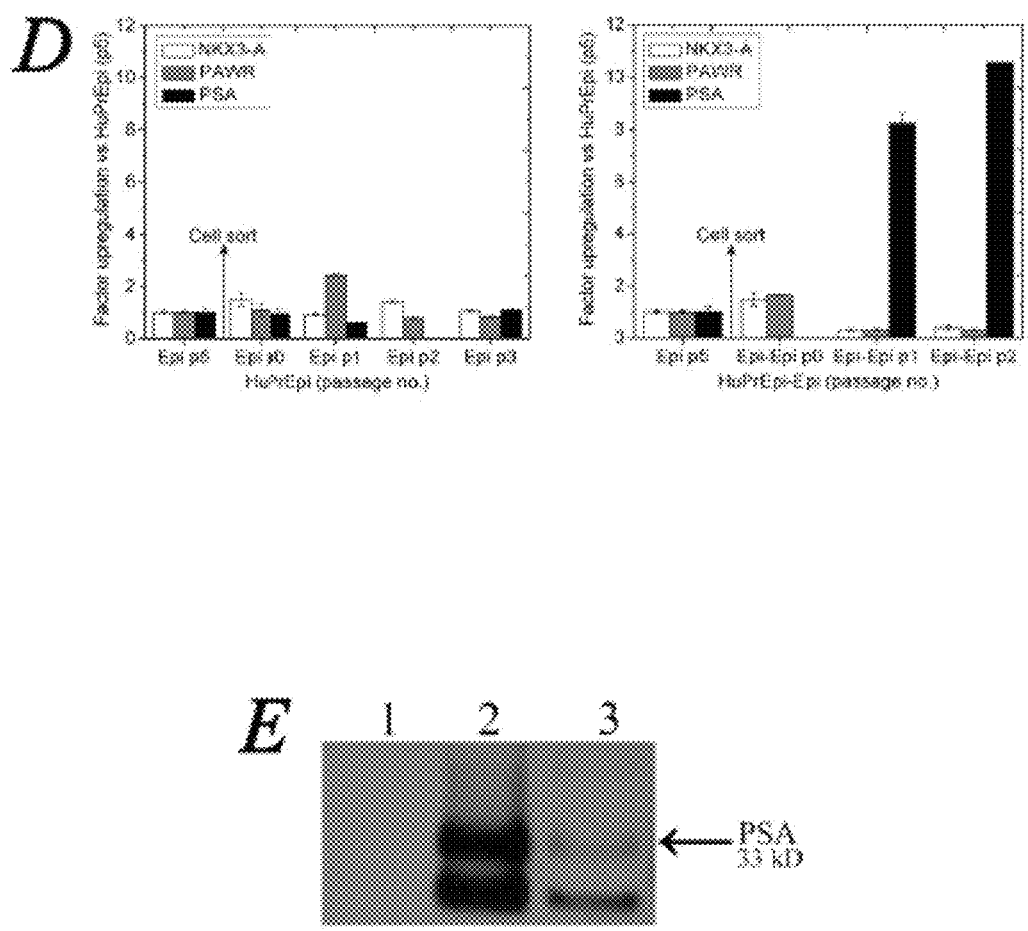

Prostate specific antigen, PSA, commonly used as a biomarker for human prostate carcinoma, is lacking in mice. The fact that PSA is elevated in human prostate cancers but does not present in mice makes this protein an attractive candidate marker for tracking human prostate cancers and their metastasis in murine xenograft models. However, it has proven problematic to develop human prostate models that maintain PSA, even when starting from primary prostate cancers. The Epi-Epi p2 prostate cancer cells expressed elevated PSA in culture, but continued to express significant PSA as tumors in murine xenograft models. PSA levels were sustained or even increased following serial tumor passaging in vivo (FIG. 11A-11E). Elevated PSA was also detected in the tumors that developed directly from injections of the transformed prostate epithelial cells and in all subsequent generations of tumors resulting from in vivo passaging. Expression did not depend on tumor site, and Western blot and antibody staining demonstrated human PSA expression in subcutaneous, orthotopic (prostate) and internal (e.g. lymph nodes, lung, etc) tumors sites. The positive detection of the human mRNA, DNA and protein PSA in these tumor tissues confirmed both the human and the prostate origin of all the cancers (FIGS. 11-11C).

The original population of karyotypically-normal prostate epithelial cells (FIG. 8) used expressed baseline levels of PSA, and it was not until the double-labeled subpopulation was selected and subcultured that PSA was seen to increase. RT-PCR analysis demonstrated that by post-sort passage 2 (Epi-Epi p2), the double-labeled cell subpopulation increased expression of PSA to >10-fold over that of the original unsorted prostate epithelial population (FIG. 11D). The high rate of PSA increase observed may be considered in light of clinical findings that a high rate of PSA increase in serum, high PSA velocity, is an established indicator of aggressive prostate cancer, and a negative prognostic indicator for cancer survival.

As expected, no increase in PSA expression was detected for the non-transforming, single-labeled control subpopulation following the sort and subsequent culturing. In addition to highly upregulated expression of PSA, the transforming Epi-Epi subpopulation also exhibited significantly decreased expression of two well-known tumor suppressors common in prostate cancer. Both NKX3-A, an androgen-regulated homeobox gene, and PAWR (prostate apoptosis gene 4), a pro-apoptotic protein first identified in prostate cancer cells, were down-regulated. Again, the control sorted single-labeled cell subpopulation, Epi, displayed no such decrease in expression of these tumor suppressors. In fact, there was a transient increase in PAWR expression detected in the single-labeled first passage cell population (Epi p1) after the sort.

In sum, human epithelial cancers were created without imposed genetic manipulation from karyotypically normal adult cells. By altering the constitutive cell-cell exchange dynamic of the cell population through selection of cells exhibiting a high level of recent exchange activity, a remarkably efficient tumorigenic transformation was accomplished. Escalated cell-cell exchanges gave way to a carcinogenesis course, with the creation of unstable cells that spontaneously transformed to a stable cancer-cell state. A population of cancer cells emerged that was highly malignant, possessing self-renewal capacity and metastatic character. During transformation in vitro the human prostate cancer cells upregulated PSA and downregulated well-known prostate tumor suppressor genes were produced. The transformed cells were 100% effective in developing malignant cancers in immunocompromised mice. The tumors exhibited high PSA expression and self renewal capacity was demonstrated by serial completely effective passage of tumors in vivo over eight generations to date. Most remarkable was the ability of the cells to spontaneously home to the prostate and to those sites that are established sites of metastasis in clinical prostate cancer patients. The fact that the reprogrammed human prostate cells were able to home to normal, uninjured, mouse prostate, places the homing capacity of these cancer cells beyond that currently ascribed to adult stem cells and suggests the triggering of programs related to homing in embryogenesis and development.

These results indicate that cell-cell fusions among primary fibroblasts, without genetic manipulation, viral infections or other predisposing alterations, can trigger a carcinogenesis program that transforms primary cells into cancer cells and drives their malignant progression in vivo. The isolation, sequestering and passaging of fused cells at densities optimized to promote further fusions gave rise to a population of cells that underwent a synchronized transformation. The transformation process itself was characterized by the breakdown of the actin cytoskeleton, the merging of nuclei, re-sorting of chromatin and the reapportionment of nuclear and cytoplasmic material of the syncytial cells into smaller cells with a high nuclear to cytoplasmic ratio. The resulting cancer cells were mononuclear, aneuploid cells that presented a classic cancer cell phenotype and genotype, both in vitro and in vivo.

Strikingly, spontaneous fusion among adult fibroblasts brought about a synchronous transformation of the cell population, in turn triggering the programmed regulation of the well-established cancer genes. The results reported herein demonstrate that in cancer cells, the hallmark oncogenesis gene dysregulations generally thought to derive from selection pressures acting on random mutations over time are likely the result of a well-orchestrated but inappropriately-triggered genetic program.

More specifically, the studies described herein suggest that the transformation event itself may be capitalizing on innate fusion-dependent programs meant to confer greater organismal fitness; for example, the fusion of bone-marrow-derived stem cells to sites of tissue damage to effect repair not otherwise possible or in sexual reproduction itself, where the fusion of gametes serves to introduce robustness through genetic mixing. If the genetic dysregulation, e.g. increased oncogene and decreased tumor-suppressor expression, common to cancer cells is indeed a programmed response rather than the result of selection of random mutations, the therapeutic ramifications would be considerable.

Tracking an aberrantly triggered cellular program that leads to cancer would greatly simplify and inform the search for therapeutic targets and strategies. Although many critically important and highly-regulated genes involved in cell transformation and subsequent tumor progression have been intensely investigated over decades, the vast majority of cancer gene regulations are still unknown. This is particularly true of the myriad of lesser-magnitude cancer-associated genetic regulations still unstudied that may prove vital both for understanding and thwarting tumor growth. By allowing cell transformation to unfold without introducing predisposing genetic alterations, conditions may be more favorable for assessing the combined effect of these gene regulations. Beyond genetic considerations, the roles of membrane, cytoskeletal, and nuclear modulations during the transformation event also assume a greater mechanistic importance in these investigations, insofar as membrane and nuclear activities define the reduction from syncytial to synkaryotic forms observed during transformation.

A fusion-initiated process of cancer induction lies well outside the classic carcinogenesis paradigm, which asserts that cancer originates from a single cell that has acquired oncogenic mutations. Cancers do not result from a single mutated cell gone awry, but rather from a multilevel process linking intercellular-interactions, nuclear and cytoskeletal modifications, chromosomal aberrations and genomic mixing among cells. Primary mammalian cells in vitro, removed from the three-dimensional attachments which dictate cooperative interaction in vivo, can undergo significant levels of cell-cell fusions. It is likely that the propensity to fuse may be a general feature of the single-cell state, and that the cancer cell, no longer constrained to be a cooperating cell in a tissue, may invoke this single-cell program. If true, the three-dimensional tissue organization of multi-cellular organisms would act to thwart cell-cell fusion and suppress the oncogenic process. From this perspective, a role for cell fusion in oncogenesis could lend additional mechanistic insight to numerous studies that have demonstrated carcinogenesis suppression with the proper maintenance of tissue architecture, extracellular matrix attachments and 3-D contacts and constraints. The cooperative nature of an organized tissue may serve to suppress carcinogenesis by limiting the cell mobility needed for fusions to occur.

At the other extreme, cell overgrowth may encourage cell-cell fusion. This would be consistent with the transformation occurring in areas of hyperplasia in patients. It has been shown that activations of oncogenes associated with proliferation and cell overgrowth are often the first oncogenic genes to be dysregulated, frequently leading to neoplasia and hyperplasia, but not directly to frank cancer and genomic instability. Without wishing to be bound by theory, it may be that aberrant cell juxtapositions and tissue organization which occur within sites of hyperplasia are also permissive of cell-cell fusion and act in concert with the well-documented genetic dyregulations to further promote oncogenesis.

In sum, this work provides a unified carcinogenesis paradigm linking both genetic and non-genetic processes. Knowing cell-cell interactions alone can orchestrate cancer gene dysregulations may help better define mechanistic linkages between tissue architecture, stromal-epithelial interactions, aneuploidy, and genomic instability. Cancer may be interpreted as an emergent process where loosening of cell-cell and tissue constraints and tissue architectural disruptions can directly regulate oncogenic signaling. This calls for linking current genetic and non-genetic investigations through a systems-wide approach to better dissect underlying carcinogenesis mechanisms and designing therapeutic strategies. In particular, the fact that profound modulations in membrane, nuclear and cytoskeletal characteristics of these cells was observed simultaneous with their transition from a multinuclear to single nuclear state indicates that it would be fruitful to invest more effort in establishing the role these subcellular activities play in the transformation process.

Results reported herein were obtained using the following methods and materials.

Cell Culture.

Lewis lung cell (LLC) murine lung carcinoma was obtained from American Type Culture Collection (Manassas, Va.). Lewis lung cells were cultured in DMEM, high glucose (Gibco Invitrogen Cell Culture, Carlsbad, Calif.) with 10% FBS (Gibco Invitrogen Cell Culture). Murine lung fibroblasts (MLF) were harvested from the lung of 40-60-day-old non-tumor bearing mice as described by Kumar et al. (1991). Mice were overdosed with 0.8 cc of Avertin (Sigma, St. Louis, Mo.). Lungs were removed and placed in 1×PBS in sterile conditions. Lungs were then diced into small chunks (1-2 $mm^2$) and spread out on 1-10 $cm^2$ plates. They were then covered with a minimal amount of DMEM, low glucose with 10% FBS and 100 µg/ml of penicillin/streptomycin and placed gently in cell incubators. The media was gently replaced on the plates after 2 days. The MLF cell outgrowth from the chunks was trypsinized when 80% confluent using 0.05% Trypsin-EDTA (Gibco Invitrogen Cell Culture, Carlsbad, Calif.) and placed back in culture. MLF cells were maintained in the same media used to isolate the cells.

Human adult normal prostate epithelial cells and specified optimal growth media were obtained from Clonetics-Lonza (PrEC, Cat #CC-2555). Cryovials were thawed at 37° C., 2 min, cells seeded at 2500 cells/$cm^2$ in 25 $cm^2$ and 75 $cm^2$ flasks (Corning, USA) incubated under 5% $CO_2$. Cells passed at 80% confluence.

Cocultures.

For the studies with mouse lung cells, the following procedures were used. All primary cells were cocultured through passage 8. All cells were detached from flasks using standard methods. Cells were counted for each population with a hemocytometer, and were separated into three 15 ml centrifuge tubes. One tube was labeled with 50 nM of Qtracker® 525 (Green) cell labeling dye (Invitrogen, Carlsbad, Calif.) and another with 45 nM of Qtracker® 655 cell labeling dye (Red) (Invitrogen). The third tube, with 2×10⁵ cells, was not labeled. All tubes were incubated at 37° C. in a cell incubator for one hour and cells labeled with Qtrackers® were washed three times with the appropriate media. After the final wash all cells were resuspended in the appropriate media with supplements. Tubes labeled with no dye were plated in T25 flasks. Approximately 2×10⁵ cells with Qtracker® 525 and with Qtracker® 655 were plated in separate T25 flasks. Approximately 5×10⁵ cells with Qtracker® 525 and Qtracker® 655 were combined and placed in T75 flasks in triplicates. All flasks were incubated at 37° C., 5% $CO_2$, for 24 hours with the appropriate media.

For the studies with human prostate epithelial cells, the following procedures were used. At four passages in culture, 3×10⁶ cells were placed in 15 ml centrifuge tubes with either 50 nM of Qtracker 525 (Green) cell labeling dye (Molecular Probes, CA), or 45 nM of Qtracker 655 (Red) cell labeling dye (Molecular Probes, CA). The third tube containing 2×10⁵ cells with no Qtracker was used as an additional control. Tubes were incubated 1 hours at 37° C. one hour, and cells washed three times with appropriate media. Cells then resuspended in appropriate media with supplements. Cells (2×10⁵) from each of the three tubes were plated in three T25 flasks. Cells (5×10⁵) from tubes with Qtracker 525 and with Qtracker 655 were combined for co-culture and placed in T75 flasks in triplicate. All flasks were placed in a cell incubator at 37° C. with 5% $CO_2$ for 24 h.

Cell Sorting.

Cells were washed once with 1×PBS, trypsinized and suspended into 15-ml centrifuge tubes, and pelleted at room temperature for 5 minutes (e.g., at 300×g). The supernatant was removed and cells were resuspended in approximately 0.5 ml of the appropriate media in 5 ml polypropylene round-bottom tubes (Becton Dickinson, Franklin Lakes, N.J.). Cells were sorted using a MoFlos (Dako, ne Cytomation) cell sorter. Cells which detached from T25 flasks were used as controls to optimize the gates for the cell sorter. Double-labeled cells possessing both red and green Qtrackers were collected and defined as functionally exchanging cells. Single-labeled cells with either red or green Qtrackers alone were collected and these populations used as controls for the studies. A small portion of sorted cells were placed on cover slips that were treated with ECL cell attachment matrix (entacin-collagen IV-laminin) from Upstate (Temecula, Calif.) for microscopy. The rest of the sorted cells were placed in the appropriate sized flask for culture.

RNA Isolation.

RNA was isolated from cultures pre- and post-sort (e.g., MLF, LLC, and MLF-MLF fused cells). Cells were placed in TRIzol (Invitrogen) for 5 min at room temperature. Cells in TRIzol® were incubated for 5 minutes at room temperature. Chloroform (0.2 ml per 1 ml of TRIzol®) was added to each sample (containing 0.5-1.0×10⁶ cells) and incubated at room temperature for 5 minutes. The samples were centrifuged at 10,000×g for 15 minutes at 4° C. The aqueous phase which contains the RNA was transferred to a clean 1.5 ml eppendorf tube. Isopropyl alcohol (0.5 ml per 1 ml of aqueous phase) was gently added. Samples were incubated at room temperature for 10 minutes and centrifuged at 10,000×g for 10 minutes at 4° C. The supernatant was discarded and the RNA pellet was washed once with 70-75% ethanol. The RNA from the cells (e.g., MLF, LLC, and MLF-MLF cells) was resuspended in 10 µl RNase-free water. The RNA from human prostate epithelial cells was resuspended in 5 µl in RNase-free water. The RNA from LLC-LLC cells was resuspended in 100 µl in RNase-free water. 1 µl from each sample was put aside for RNA integrity testing. The rest of the RNA was stored at −80° C. Quality and quantity of total RNA isolated was measured by using an Agilent 2100 bioanalyzer.

cDNA Generation.

Total RNA from MLF, LLC, and different passages of MLF-MLF was isolated using TRIzol®. RNA integrity was confirmed by lab-on chip technology, using an Agilent 2100 bioanalyzer in combination with the RNA 6000 Lab Chip kit according to the manufacturer's instructions (Agilent Technologies, Boeblingen, Germany). cDNAs were synthesized from 1 µg total RNA using High Capacity cDNA Reverse Transcription kit (ABI, Applied Biosystems) and stored at −20° C. or −80° C. until use.

Real-Time Quantitative PCR.

Expression levels of RNA transcripts were quantitated by real-time PCR using a 7300 Real Time PCR System from Applied Biosystems. Complementary DNAs were mixed with TaqMan universal PCR master mix (Applied Biosystems) and primers (CDKn2a, Spp1, p53, MYC, Bcl-2, Kras, CD44, and VEGFa) for mouse lung cell studies or primers (PSA, NKX3-A and PAWR) for human epithelial prostate cell studies before performing real-time PCR. PCR conditions for all RT-PCRs were preformed as follows: denaturation at 95° C. for 30 sec, annealing at 60° C. for 30 seconds and extension at 72° C. for 1 minute. In addition to profiling all samples for the target sequence, samples were profiled for 18S (ribosomal RNA) expression as endogenous control. For each single well amplification reaction a threshold cycle (CT) was observed in the exponential phase of amplification and the quantitation of relative expression levels was achieved using standard curves for both the target and endogenous controls. All assays were performed in triplicate.

Proliferation Assay.

The CyQUANT® Cell Proliferation Assay was performed using the standard protocol recommended by Invitrogen. For the cell proliferation standard curve, a concentrated cell suspension in medium with a density of 10⁵ cells/ml was prepared. Serial dilutions in the wells of a 96 well plate (black, clear bottom, Costar 3603) were performed such that 200 µvolumes of growth medium contain cell numbers ranging from 1000 to 20,000. A control well with no cells was also included. After 48-72 hours cells were centrifuged, the supernatant removed and the plates frozen at −80° C. overnight. The cells were thawed the next day, 200 µl of the CyQUANT®GR dye/lysis buffer (Invitrogen) was added to each well and incubated for 2-5 min at room temperature. The 96-well plates were read at 485 nm on a Victor 2 fluorescence plate reader to quantify total fluorescence from each well.

Nuclear and Cell Area Quantification.

Cells were prepared and stained on the same day for quantification. Cells were detached from the flasks and 1×10⁷ cells (in form of a cell pellet) were resuspended in 4% paraformaldehyde for 15 minutes at room temperature for fixation. Cells were washed once with 1× Tris-buffered saline, pH 7.4 (1×TBS) and resuspended in Hoechst nuclear stain (Invitrogen) at a concentration 4 µg/ml in 1 ml of 1×TBS for 15 minutes at room temperature. Cells were washed once again with 1×TBS. Cells were then resuspended in 60 µl of 1×TBS and kept at 4° C. until ready to use. An ImageStream® cell analysis system (Amnis, Seattle, Wash.) was used to image and quantify 10,000 to 20,000 cells for each cell type. IDEAS Application© software was used to analyze the nuclear and cell area for each cell type.

Soft Agar Assay.

1% Agar (DNA grade) in 1×PBS was autoclaved and cooled to 40° C. in a water bath. An equal volume of the appropriate 2× media and the 1% agar was mixed to give 0.5%. 4 ml of the new agar mix was poured in 60 mm×15 mm cell culture dish from Corning (Corning, N.Y.) and allowed to set. 0.7% agar in 1×PBS was autoclaved and allowed to cool to 40° C. 5000 cells/plate is needed for this assay, so cells were prepared at a concentration of 2×10$^5$ cells/ml. 0.1 ml of cell solution or 20,000 cells were placed in a 15 ml centrifuge tube and 3 ml of the appropriate 2× media was added to the tube. 3 ml of 0.7% agar was mixed with 3 ml of the cells in the 15 ml tube. 1.5 ml of the cell and agar solution was added to each culture dish containing 0.5% agar prepared earlier. The assay was incubated at 37° C. in a cell incubator for 10 to 14 days. Cultures were stained with 0.005% Crystal Violet (Sigma-Aldrich) for 1 hour and colonies were quantified using a dissecting microscope.

mFISH.

For the studies with mouse lung cells, the following procedures were used. Slides were made using a single-cell suspension in 3:1 methanol:acetic acid fixative, then dehydrated. Metaphase chromosome preparations were pretreated and denatured in a series of solutions including saline sodium citrate and sodium hydroxide. Chromosome preparations were then dehydrated and air dried. A 10 μl aliquot of Mouse m-FISH probe cocktail (Metasystems, Altlussheim, Germany) was denatured at 75° C., quickly cooled, and prehybridized at 37° C. for 30 minutes. The probe was added to the slide, coverslipped and sealed with rubber cement for incubation over the course of 4 days at 37° C. Posthybridization washes were performed using saline sodium citrate and Tween-20 solutions. The chromosomes were counterstained with DAPI and an Olympus AX-70 microscope with appropriate filter sets were used to visualize the probe hybridization on the chromosomes.

For the studies with human prostate epithelial cells, the following procedures were used. Mounted frozen tissue removed from −80° C. for 30 min room temp prior to staining. Sections were rinsed in PBS, fixed in 100% methanol at −20° C. for 10 min, washed PBS, and placed in 4% PFA 3 min at room temp. Slides washed 2×. Total protein was extracted from frozen sample by standard extraction protocol. A 50 μg quantity of total protein from each tissue extract was separated on 12% SDS gels (Bio-Rad) and transferred to nitrocellulose membranes (Amersham Biosciences). The membranes were treated in PBS containing 0.05% Tween 20 and 5% nonfat dry milk for 1 h, then probed with monoclonal antibody to PSA (Scripps Laboratories) at 1:1000 4° C. overnight. After wash, membranes were incubated with horseradish peroxidase-conjugated secondary antibody (diluted 1:2000, DAKO) 1 hours room temp. An ECL Plus detection kit (Amersham Biosciences) was used to visualize the reaction by chemiluminescence with PBS for 5 min each at room temperature. To each tissue section hybridization buffer was added containing 20 mM Tris-HCl [pH 7.2], 0.01% SDS, 0.9M NaCl, and 15% formamide. An oligonucleotide was labeled with Alexa 488 (Eurofins MWG Operon, Huntsville, Ala., USA) for the PSA probe (sequence obtained from NCBI Accession: BC005301 and probe sequence used: 3' GCA GGG CAG TCT GCG GCG GTG TTC TGG TGC ACC CCC AGT GGG TCC TCA CAG CTG CCC ACT GC 5'). Hybridization on the slide was at 46° C., 16 hr, in dark. After hybridization, slides were rinsed PBS, 46° C., and placed in wash buffer (20 mM Tris-HCl [pH 7.2], 0.01% SDS, 0.318M NaCl) at 48° C., 15 min, in dark. Slides were quickly immersed in PBS. For nuclear staining, 1 mM To-Pro-3 (Molecular Probes) diluted to 2 μM in PBS and incubated on tissue sections for 15 min room temp in dark. Tissue was rinsed in PBS 5 min, and anti-fade mounting solution added. Slides were coverslipped, sealed and stored at −20° C.

Immunofluorescence Antibodies.

For immunofluorescence Anti-CD44 (A020), Human (Rat) (Calbiochem, San Diego, Calif.) was used at a dilution of 1:400 for dual stain, goat polyclonal MMP-9 (C-20) (Santa Cruz Biotechnology, Inc, Santa Cruz, Calif.) was used at a dilution of 1:100 for dual stain, and monoclonal anti-rabbit monoclonal OPN antibody (this antibody was generously and kindly provided by Dr. Larry Fisher from NIH) at a dilution of 1:400 for dual stain.

Immunofluorescence Staining.

For the studies with mouse lung cells, the following procedures were used. Cells were placed on 22×22 mm glass cover slips (Brain Research Laboratories, Cambridge, Mass.) in 6-well plates from Corning (Corning, N.Y.). The cover slips were prepared for cells by sterilizing under UV light for 1 hour. 1 ml of ECL cell attachment matrix (entacin-collagen IV-laminin) from Upstate (Temecula, Calif.) was added to each well at a concentration of 20 μg/ml. The 6-well plates were placed at 37° C. for one hour. The ECL cell attachment matrix was removed from each well. The cover slips were rinsed with DMEM, low glucose with 10% FBS. Cells were added to the coverslips and incubated at 37° C. until the desired cell density was reached. Media from the cells on cover slips in 6 well-plates were removed and cells were washed once with 1×PBS. 4% paraformaldehyde (PFA) was added for 15 minutes at 20° C. PFA was removed and cells were washed twice with 1×PBS, and incubated with 1% bovine serum albumin (BSA) (Sigma, St. Louis, Mo.) for 1 hour at room temperature. Another blocking step for 1.5 hours incubation at room temperature was done using Mouse Detective from Biocare Medical (Concord, Calif.). For dual antibody stains, cells were incubated at room temperature for 2 hours with a mix of the appropriate antibodies in 1% BSA. The cells were washed once with 10% goat serum (Gibco Invitrogen Cell Culture) after two hours. For CD44 stain, the cells were first stained with anti-rat Alexa 488 secondary antibody (Molecular Probes, Carlsbad, Calif.) at a dilution of 1:300 in 10% goat serum for 1 hour in the dark. For MMP-9 stain, the cells were first stained with anti-goat Alexa 488 secondary antibody (Molecular Probes) at a dilution of 1:300 in 10% donkey serum for 1 hour in the dark. 1× wash in 1×PBS followed for 5 minutes at room temperature, and another hour incubation in the dark occurred for OPN stain with anti-rabbit Alexa 555 secondary antibody (Molecular Probes) at a dilution of 1:300 in 10% goat serum. After last secondary antibody step, 2 washes with 1×PBS was done for 5 minutes each at room temperature. To stain the nucleus, 1 mM of To-Pro®-3 (Molecular Probes) was diluted to 2 μM in 1×PBS and incubated on the cells for 10 minutes at room temperature in the dark. The cells were rinsed once with 1×PBS and Vectashield® anti-fade mounting solution (Vector Laboratories, Burlingame, Calif.) was added. The cover slips were placed on slides and sealed with nail polish. The slides were stored at −20° C. until evaluation.

For the studies with human prostate epithelial cells, the following procedures were used. Frozen tissue sections removed from −80° C. and placed 30 min room temp for prior to staining. Sections rinsed PBS, fixed: 10 min at −20° C. in 80% methanol and 3 min room temperature in 4% PFA. Slides washed 3×PBS (5 min) at room temp. Nonspecific sites blocked by incubation with 1% BSA room temp. 1 hr. Additional blocking done using mouse detective (Biocare Medical, Concord, Calif.) 4 hours room temp. For PSA immunofluorescence, sections incubated with rabbit monoclonal Prostate Specific Antigen (PSA) antibody (Abcam Inc., Cambridge, Mass., USA) at 1:100 dilution in 1% BSA at 4° C. overnight. Next day sections washed 10% goat serum 3× (5 min) at room temperature. Alexa Fluor® 555 goat anti-rabbit IgG secondary antibody (Molecular Probes, Carlsbad, Calif.) applied at 1:300 in 10% appropriate serum and placed 1 hour in the dark. Sections were washed 2× in PBS, 5 min room temp. For nuclear staining, 1 mM To-Pro-3 (Molecular Probes) diluted to 2 µM in PBS and incubated on sections for 15 minutes in darkness at room temperature. Sections rinsed PBS (5 min) and anti-fade mounting solution added. Slides coverslipped, sealed, stored at −20° C.

F-Actin Staining.

Cells were washed twice with 1×PBS on cover slips. 4% paraformaldehyde (PFA) was added for 15 minutes at room temperature. PFA was removed and cells were washed twice with 1×PBS. 0.1% Triton X-100 (Sigma-Aldrich) in 1×PBS was placed on cells to permeabalize membrane for 5 minutes. Cells were washed twice with 1×PBS. Cells were incubated with 1% bovine serum albumin (BSA) for 30 minutes at room temperature. Cells were washed again two more times with 1×PBS. Cells were stained with 10 µl Alexa Fluor 594 phalloidin (Molecular Probes) with 200 µl of 1×PBS per cover slip for 20 minutes. Cells were washed two more times with 1×PBS and stained with the same nuclear dye as the previous section.

Microscopy.

Cells or tissue sections were viewed using a Zeiss® LSM 510 Meta Confocal Scanning System (Carl Zeiss, Jena, Germany) equipped with an Argon laser, HeNe laser 543 nm, HeNe laser 633 nm, and 3 separate detectors that allow 3 sequential or simultaneous imaging using 3 different fluorophores. The third detector, referred to as the Meta detector, can be configured to capture up to 8 separate color channels. Images were captured using 3 separate photomultiplier tubes for each detector at $1024 \times 10^{24}$ pixels. Z-stacks were obtained when necessary. Reconstruction of the z-stack was done using Zeiss software.

Murine Skin Xenograft Model.

For the studies with mouse lung cells, the following procedures were used. Mice were not less than 8 weeks of age at the time of injection. In preparation for injection, the caudal half of the back was shaved and swabbed with antiseptic solution. Mice were anesthetized with a 0.5 mg/g intra-peritoneal dose of Avertin, marked with an ear tag, and marked at the tail for easy short-term identification. Tumor cells and sorted fused cells were suspended in a solution of PBS. Using a 1cc syringe and a 27G needle, $1 \times 10^6$ tumor cells or fused cells were injected subcutaneously in 0.2 cc PBS.

Following injection, mice were monitored regularly. Tumor size was measured every day with calipers. Once tumors reached about 1500-2000 mm³, mice were sacrificed and the tissues processed.

For the studies with human prostate epithelial cells, the following procedures were used. Balb/c (CByJ.Cg-Foxn1nu/J) and SCID (NOD.CB17-Prkdcscid/J) mice, at least 8 weeks of age, were used (Jackson Labs, Bar Harbor, Me.). Subcutaneous cell injections (0.2 ml in PBS) and serial passaging of 1 mm³ tumor fragments was made into the caudal portion of the back. Mice were monitored and tumor size and animal weight measured daily. When subcutaneous tumors reached 1000-1500 mm³, mice were in distress, or have lost 20% of total body weight (indicative of internal tumor burden), animals were sacrificed. Full autopsy and tissue collection performed at sacrifice. Tissues were divided and aliquoted for assays. Samples were slow-frozen in OCT (Tissue Tek, Fisher Scientific) in the gas phase of liquid nitrogen. Tissue samples were placed in 10% formalin for not more than 24 hr, processed and paraffin-embedded.

Tissue Processing.

Mice were anesthetized with 0.5 mg/g intra-peritoneal dose of Avertin. Mice were sacrificed with an overdose of Avertin (1.2 mg/g). When the animal was unresponsive to tail pinch, and exhibited physiologic signs of deep anesthesia, the thoracic cavity was immediately opened by median sternotomy. Ice cold PBS and Heparin (Sigma) at 1000 U/L were flushed through the left ventricle and out a vent in the right atrium. A portion of the tissue was quickly dissected and slow-frozen in OCT (Tissue Tek, Fisher Scientific) in the gas phase of liquid nitrogen. The rest of the tissue was placed in 10% formalin and processed for paraffin embedding. The tissue was embedded in paraffin cassettes and stored until ready for staining.

Immunohistochemistry.

For the studies with mouse lung cells, the following procedures were used. Paraffin-embedded tissue was cut into 4 µm slices using a microtome and placed on positively charged slides (Fisher Scientific). Standard procedure was used to stain the tissue for H&E. All slides were stained with different antibodies using the Benchmark® XT IHC/ISH Staining Module from Ventana Medical Systems, Inc (Tucson, Ariz., USA). All antibodies and reagents were furnished at the correct final dilutions and concentrations, for the Benchmark® XT staining module, from Ventana Medical Systems. Freshly cut tissue sections on slides were placed in the Benchmark XT module and slides were stained with the appropriate antibody using the automated system. Once the staining was complete coverslips were applied to each slide.

For the studies with human prostate epithelial cells, the following procedures were used. Standard H&E staining was done on 4 µm sections from formalin-fixed paraffin-embedded tumor samples. PSA antibody staining was done using the Benchmark XT IHC/ISH Staining Module from Ventana Medical Systems, Inc (Tucson, Ariz.). Antibodies and reagents (Ventana Medical Systems) were furnished at the final concentrations used in the Benchmark XT staining module. Tissue sectioning and staining done by clinical histology unit (EXCELL, Caritas St. Elizabeth's Medical Center, Tufts Univ. School of Med., Boston, Mass.). Histopathological staging was done by clinical pathologist Dr. Douglas Schneider, CSEMC.

Immunohistochemistry.

Total protein was extracted from frozen tissue samples by standard extraction protocol. A 50 µg quantity of total protein from each tissue extract was separated on a 12% SDS gels (Bio-Rad) and transferred to nitrocellulose membranes (Amersham Biosciences). The membranes were treated in PBS containing 0.05% Tween 20 and 5% nonfat dry milk for 1 h, then probed with monoclonal antibody to PSA (Scripps Laboratories) at 1:1000 overnight, 4° C. After washing, the membranes were incubated with horseradish peroxidase-conjugated secondary antibody (diluted 1:2000, DAKO) for 1 hr, room temp. An ECL Plus detection kit (Amersham Biosciences) was used to visualize the reaction by chemiluminescence.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

1. Abdollahi, A., Lipson, K. E., Han, X., Krempien, R., Trinh, T., Weber, K. J., Hahnfeldt, P., Hlatky, L., Debus, J., Howlett, A. R. & Huber, P. E. SU5416 and SU6668 attenuate the angiogenic effects of radiation-induced tumor cell growth factor production and amplify the direct anti-endothelial action of radiation in vitro. Cancer Res. 63(13), 3755-3763 (2003).
2. Adams, J. M. & Cory, S. The Bcl-2 apoptotic switch in cancer development and therapy. Oncogene 26(9), 1324-37 (2007).
3. Aharon, R. & Bar-Shavit, Z. Involvement of aquaporin 9 in osteoclast differentiation. J Biol. Chem. 281(28), 19305-19309 (2006).
4. Alvarez-Dolado, M., Pardal, R., Garcia-Verdugo, J. M., Fike, J. R., Lee, H. O., Pfeffer, K., Lois, C., Morrison, S. J. & Alvarez-Buylla, A. Fusion of bone-marrow-derived cells with Purkinje neurons, cardiomyocytes and hepatocytes. Nature 425(6961), 968-973 (2003).
5. Anderson, A. R. & Quaranta, V. Integrative mathematical oncology. Nature Rev Cancer 8(3), 227-234 (2008).
6. Barcellos-Hoff, M. H. Cancer as an emergent phenomenon in systems radiation biology. Radiat Environ Biophys. 47(1), 33-38 (2008).
7. Barcellos-Hoff, M. H., Park, C. & Wright, E. G. Radiation and the microenvironment—tumorigenesis and therapy. Nature Rev Cancer 5(11), 867-875 (2005).
8. Barski, G., Sorieul, S. & Cornefert, F. Production dans des cultures in vitro de deux souches cellulaires en association de cellules de caratere hybride. C. R. Hebd. Seances Acad. des Sci. 251, 1825-1827 (1960).
9. Beauséjour, C. M. & Campisi, J. Balancing regeneration and cancer. Nature 443, 404-405 (2006).XXX
10. Beauséjour, C. M., Krtolica, A., Galimi, F., Narita, M., Lowe, S. W., Yaswen, P. & Campisi, J. Reversal of human cellular senescence: roles of the p53 and p16 pathways. EMBO J. 22(16), 4212-4222 (2003).
11. Bhatia, B., Multani, A. S., Patrawala, L., Chen, X., Calhoun-Davis, T., Zhou, J., Schroeder, L., Schneider-Broussard, R., Shen, J., Pathak, S., Chang, S. & Tang, D. G. Evidence that senescent human prostate epithelial cells enhance tumorigenicity: cell fusion as a potential mechanism and inhibition by p16INK4a and hTERT. Int J Cancer 122(7), 1483-1495 (2008).
12. Bhowmick, N. A., Chytil, A., Plieth, D., Gorska, A. E., Dumont, N., Shappell, S., Washington, M. K., Neilson, E. G. & Moses, H. L. TGF-beta signaling in fibroblasts modulates the oncogenic potential of adjacent epithelia. Science 303(5659), 848-851 (2004).
13. Bissell, M. J., Kenny, P. A. & Radisky, D. C. Microenvironmental regulators of tissue structure and function also regulate tumor induction and progression: the role of extracellular matrix and its degrading enzymes. Cold Spring Harb Symp Quant Biol. 70, 343-356 (2005).
14. Boveri T. On multipolar mitosis as a means of analysis of the cell nucleus. In: Willier B. H. and Oppenheimer J. M., editors. Foundations of experimental embryology. Englewood Cliffs, N.J.: Prentice-Hall. p 74-97 (1964).
15. Bugge, T. H., Kombrinck, K. W., Xiao Q., Holmbäck, K., Daugherty, C. C., Witte, D. P. & Degen, J. L. Growth and dissemination of Lewis lung carcinoma in plasminogen-deficient mice. Blood 90(11), 4522-4531 (1997).
16. Chen, E. H., Grote, E., Mohler, W. & Vignery, A. Cell-cell fusion. FEBS Letters 581, 2181-2193 (2007)
17. Ciardiello, F. & Tortora, G. Inhibition of bcl-2 as cancer therapy. Ann Oncol. 13(4), 501-502 (2002).
18. Coppola, D., Szabo, M., Boulware, D., Muraca, P., Alsarraj, M., Chambers, A. F. & Yeatman, T. J. Correlation of osteopontin protein expression and pathological stage across a wide variety of tumor histologies. Clin Cancer Res. 10(1 Pt 1), 184-190 (2004).
19. Coussens, L. M., Fingleton, B. & Matrisian, L. M. Matrix metalloproteinase inhibitors and cancer: trials and tribulations. Science 295, 2387-2394 (200)??
20. Cui, W., Ke, J. Z., Zhang, Q., Ke, H-Z., Chalouni, C. & Vignery, A. The intracellular domain of CD44 promotes the fusion of macrophages. Blood 107, 796-805 (2006)X
21. Cunha, G. R., Hayward, S. W., Wang, Y. Z. & Ricke, W. A. Role of the stromal microenvironment in carcinogenesis of the prostate. Int J Cancer 107(1), 1-10 (2003).
22. De Baetselier, P., Roos, E., Brys, L., Remels, L., Gobert, M., Dekegel, D., Segal, S. & Feldman, M. Nonmetastatic tumor cells acquire metastatic properties following somatic hybridization with normal cells. Cancer Metastasis Rev. 3(1), 5-24 (1984)
23. DeFife, K. M. & Jenney, C. R. Disruption of filamentous actin inhibits human macrophage fusion. FASEB J 13, 823-832 (1999)
24. Desai, B., Rogers, M. J. & Chellaiah, M. A. Mechanisms of osteopontin and CD44 as metastatic principles in prostate cancer cells. Molec. Cancer 6(18), 1-16 (2007)
25. Duelli, D. M., Padilla-Nash, H. M., Berman, D., Murphy, K. M., Ried, T. & Lazebnik, Y. A virus causes cancer by inducing massive chromosomal instability through cell fusion. Curr Biol. 17, 431-437 (2007).
26. Duelli, D. & Lazebnik, Y Cell-to-cell fusion as a link between viruses and cancer. Nat Rev Cancer 7(12), 968-976 (2007).
27. Duesberg, P., Li, R., Sachs, R., Fabarius, A., Upender, M. B. & Hehlmann, R. Cancer drug resistance: the central role of the karyotype. Drug Resist Updat. 10(1-2), 51-58 (2007).
28. Dvorak, H. F. Tumors: wounds that do not heal. Similarities between tumor stroma generation and wound healing. N Engl J. Med. 315(26), 1650-1659 (1986).
29. Egeblad, M. & Werb, Z. New Functions for the matrix metalloproteinases in cancer progression. Nature Revs Cancer 2, 161-74 (2002)
30. Enderling, H., Hlatky, L. & Hahnfeldt, P. Tumors are conglomerates of self-metastases. Submitted, 2008. XXX
31. Fabarius, A., Hehlmann, R. & Duesberg, P. H. Instability of chromosome structure in cancer cells increases exponentially with degrees of aneuploidy. Cancer Genet Cytogenet. 143(1), 59-72 (2003)
32. Fabarius, A., Li, R., Yerganian, G., Hehlmann, R. & Duesberg, P. Specific clones of spontaneously evolving karyotypes generate individually of cancers. Cancer Genet Cytogenet 180, 89-99 (2008)
33. Feinendegen, L., Hahnfeldt, P., Schadt, E. E., Stumpf, M. & Voit, E. O, Systems biology and its potential role in radiobiology. Radiat Environ Biophys. 47(1), 5-23 (2008).
34. Ferrara, N. & Henzel, W. J. Pituitary follicular cells secrete a novel heparin-binding growth factor specific for vascular endothelial cells. Biochem Biophys Res Commun. 161(2), 851-858 (1989)

35. Fillmore, C. M. & Kuperwasser, C. Human breast cancer cell lines contain stem-like cells with the capacity to self-renew, give rise to phenotypically diverse progeny and survive chemotherapy. Breast Cancer Res. 10(2), R25 (2008).
36. Folger, P. A., Berg, W. J., DeJesus, Z., Fong, Y. & Pardee, J. D. A mammalian severin replaces gelsolin in transformed epithelial cells. Cancer Res. 59(20), 5349-5355 (1999).X
37. Folkman, J., Hahnfeldt, P. & Hlatky, L. Cancer: looking outside the genome. Nature Rev Mol Cell Biol. 1(1), 76-79 (2000).
38. Fortuna, M. B., Dewey, M. J. & Furmanski, P. Cell fusion in tumor development and progression: occurrence of cell fusion in primary methylcholanthrene-induced tumorigenesis. Int J Cancer 44(4), 731-737 (1989).
39. Franklin, W. A. Pathology of invasive and preinvasive neoplasia. Chest 117, 80-89 (2000)
40. Glinsky, G. V., Glinskii, A. B., Berezovskaya, O., Smith, BA, Jiang, P., Li, X. M., Yang, M. & Hoffman, R. M. Dual-color-coded imaging of viable circulating prostate carcinoma cells reveals genetic exchange between tumor cells in vivo, contributing to highly metastatic phenotypes. Cell Cycle 5(2), 191-197 (2006).
41. Goldenberg, D. M., Pavia, R. A. & Tsao, M. C. In vivo hybridisation of human tumour and normal hamster cells. Nature 250(5468), 649-651 (1974).
42. Hahn, W. C., Counter, C. M., Lundberg, A. S., Beijersbergen, R. L., Brooks, M. W. & Weinberg, R. A. Creation of human tumour cells with defined genetic elements. Nature 400, 464-468 (1999).
43. Hahnfeldt, P., Panigrahy, D., Folkman, J. & Hlatky, L. Tumor development under angiogenic signaling: a dynamical theory of tumor growth, treatment response, and postvascular dormancy. Cancer Res. 59(19), 4770-4775 (1999).
44. Hanahan, D. & Weinberg, R. A. The hallmarks of cancer. Cell 100, 57-70 (2000)X
45. Harris, H., Miller, O. J., Klein, G., Worst, P. & Tachibana, T. Suppression of malignancy by cell fusion. Nature 223 (5204), 363-368 (1969).
46. Hlatky, L., Ring, C. S. & Sachs, R. K. Detection of an intrinsic marker in hypoxic cells. Cancer Res. 49(18), 5162-5166 (1989).
47. Houghton, J., Stoicov, C., Nomura, S., Rogers, A. B., Carlson, J., Li, H., Cai, X., Fox, J. G., Goldenring, J. R. & Wang, T. C. Gastric cancer originating from bone marrow-derived cells. Science 306(5701), 1568-71 (2004).
48. Johansson, C. B., Youssef, S., Koleckar, K., Holbrook, C., Doyonnas, R., Corbel, S. Y., Steinman, L., Rossi, F. M. V. & Blau, H. M. Extensive fusion of haematopoietic cells with Purkinje neurons in response to chronic inflammation. Nature Cell Biol., 10(5), 575-583 (2008).
49. Kao, F-T., Johnson, R. T. & Puck, T. T. Complementation analysis on virus-fused chinese hamster cells with nutritional markers. Science 164, 312-314 (1969).
50. Kass, L., Erler, J. T., Dembo, M. & Weaver, V. M. Mammary epithelial cell: Influence of extracellular matrix composition and organization during development and tumorigenesis Int. J. Biochem. Cell Biol. 39, 1987-1994.
51. Kenny, P. A. & Bissell, M. J. Tumor reversion: correction of malignant behavior by microenvironmental cues. Int J Cancer 107(5), 688-695 (2003).
52. Körbling, M., de Lima, M. J., Thomas, E., Khanna, A., Najjar, A. M., Gu, J., Gelovani, J. G. & Broaddus, R. Fusion of circulating blood cells with solid-organ tissue cells in clinical stem cell transplants: a potential therapeutic model? Regen Med 2, 157-64 (2008).
53. Kumar, R. K., O'Grady, R., Li, W., Smith, L. W. & Rhodes, G. C. Primary culture of adult mouse lung fibroblasts in serum-free medium: responses to growth factors. Exp Cell Res 193, 398-404 (1991).
54. Land, H., Chen, A. C., Morgenstern, J. P., Parada, L. F. & Weinberg, R. A. Behavior of myc and ras oncogenes in transformation of rat embryo fibroblasts. Molec Cell Biol. 6(6), 1917-1925 (1986).
55. Land, H., Parada, L. F. & Weinberg, R. A. Tumorigenic conversion of primary embryo fibroblasts requires at least two cooperating oncogenes. Nature 304(5927), 596-602 (1983).
56. Lelièvre, S. A., Weaver, V. M., Nickerson, J. A., Larabell, C. A., Bhaumik, A., Petersen, O. W. & Bissell, M. J. Tissue phenotype depends on reciprocal interactions between the extracellular matrix and the structural organization of the nucleus. Proc. Natl. Acad. Sci. USA 95(25), 14711-14716 (1998).
57. Lengauer, C., Kinzler, K. W. & Vogelstein, B. Genetic instabilities in human cancers. Nature 396(6712), 643-649 (1998).
58. Li, J., Viallet, J. & Haura, E. B. A small molecule pan-Bcl-2 family inhibitor, GX15-070, induces apoptosis and enhances cisplatin-induced apoptosis in non-small cell lung cancer cells. Cancer Chemother Pharmacol. 61(3), 525-534 (2008).
59. Loeb, L. A., Loeb, K. R. & Anderson, J. P. Multiple mutations and cancer. Proc Natl Acad Sci USA 100(3), 776-781 (2003).
60. Luth, E. S., Jun, S. J., Wessen, M. K., Liadaki, K., Gusson, E. & Kunkel. L. M. Bone marrow side population cells are enriched for progenitors capable of myogenic differentiation J Cell Sci., Apr. 8, 2008 [Epub ahead of print].
61. Margolis, R. L. Tetraploidy and tumor development. Cancer Cell 8(5), 353-354 (2005).
62. Mathews, V., Hanson, P. T., Ford, E., Fujita, J., Polonsky, K. S. & Graubert, T. A. Recruitment of bone marrow-derived endothelial cells to sites of pancreatic beta-cell injury. Diabetes 53(1), 91-98 (2004).
63. Merlo, L. M. F., Pepper, J. W., Reid, B. J. & Maley, C. C. Cancer as an evolutionary and ecological process Nature Rev Cancer 6, 924-935 (2006)
64. Metro, G., Finocchiaro, G., Toschi, L., Bartolini, S., Magrini, E., Cancellieri, A., Trisolini, R., Castaldini, L., Tallini, G., Crino, L., Cappuzzo, F. Epidermal Growth Factor Receptor (EGFR) targeted therapies in Non-Small Cell Lung Cancer (NSCLC). Rev Recent Clin Trials 1(1), 1-13 (2006).
65. Meuwissen, R. & Berns, A. Mouse models for human lung cancer. Genes Devel 19, 643-664 (2005)
66. Mitelman, F., Johansson, B. & Mertens, F. The impact of translocations and gene fusions on cancer causation Nature Rev Cancer 7, 233-245 (2007)
67. Murasawa, S., Kawamoto, A., Horii, M., Nakamori, S. & Asahara, T. Niche-dependent translineage commitment of endothelial progenitor cells, not cell fusion in general, into myocardial lineage cells. Arterioscler Thromb Vasc Biol. 25(7), 1388-1394 (2005).
68. Murga, M. & Fernández-Capetillo, O. Genomic instability: on the birth and death of cancer. Clin Transl Oncol. 9(4), 216-220 (2007).
69. Norton, L. & Massague, J. Is cancer a disease of self-seeding? Nature Med 12(8), 875-878 (2006).
70. Nowell, P. C. The clonal evolution of tumor cell populations. Science 194(4260), 23-28 (1976)-

71. Nowell, P. C. Tumor progression: a brief historical perspective. Cancer Biol 12, 261-266 (2002)
72. Nygren, J. M., Liuba, K., Breitbach, M., Stott, S., Thorén, L., Roell, W., Geisen, C., Sasse, P., Kirik, D., Björklund, A., Nerlov, C., Fleischmann, B. K., Jovinge, S. & Jacobsen, S. E. W. Myeloid and lymphoid contribution to non-haematopoietic lineages through irradiation-induced heterotypic cell fusion. Nature Cell Biol. 10(5), 584-592 (2008).
73. Ogle, B. M., Cascalho, M. & Platt, J. L. Biological implications of cell fusion. Nature Rev Molec Cell Biol 6, 567-75 (2005)
74. Overholtzer, M., Mailleux, A. A., Mouneimne, G., Normand, G., Schnitt, S. J., King, R. W., Cibas, E. S. & Brugge, J. S. A nonapoptotic cell death process, entosis, that occurs by cell-in-cell invasion. Cell 131, 966-979 (2007).
75. Parkin, D. M., Bray, F., Ferlay, J. & Pisani, P. Estimating the world cancer burden: Globocan 2000. Int J Cancer 94(2), 153-156 (2001).
76. Parris, G. E. Clinically significant cancer evolves from transient mutated and/or aneuploid neoplasia by cell fusion to form unstable syncytia that give rise to ecologically viable parasite species. Med Hypoth 65(5), 846-850 (2005a)
77. Parris, G. Some experimental observations consistent with cell fusion hypothesis of cancer evolution. Med Hypoth 65(5), 993-994 (2005b)
78. Parris, G. E. The cell clone ecology hypothesis and the cell fusion model of cancer progression and metastasis: history and experimental support. Med Hypoth 66(1), 76-83 (2006a)
79. Parris, G. The cell clone ecology hypothesis and the cell fusion model of cancer progression and metastasis (II): three pathways for spontaneous cell-cell fusion and escape from the intercellular matrix. Med Hypoth 67(1), 172-176 (2006b)
80. Pawelek, J. M. Tumour-cell fusion as a source of myeloid traits in cancer. Lancet Oncol. 6(12), 988-993 (2005).
81. Pawelek, J. M. & Chakraborty, A. K. Fusion of tumour cells with bon marrow-derived cells: a unifying explanation for metastasis. Nature Rev Cancer 8, 1-10 (2008).X
82. Pratap, J., Javed, A., Languino, L. R., van Wijnen, A. J., Stein, J. L., Stein, G. S. & Lian, J. B. The Runx2 osteogenic transcription factor regulates matrix metalloproteinase 9 in bone metastatic cancer cells and controls cell invasion. Mol Cell Biol. 25(19), 8581-8591 (2005).
83. Prince, M. E., Sivanandan, R., Kaczorowski, A., Wolf, G. T., Kaplan, M. J., Dalerba, P., Weissman, I. L., Clarke, M. F. & Ailles, L. E. Identification of a subpopulation of cells with cancer stem cell properties in head and neck squamous cell carcinoma. Proc Natl Acad Sci USA 104(3), 973-978 (2007).
84. Rafii, S., Meeus, S., Dias, S., Hattori, K., Heissig, B., Shmelkov, S., Rafii, D. & Lyden, D. Contribution of marrow-derived progenitors to vascular and cardiac regeneration. Semin Cell Dev Biol. 13(1), 61-67 (2002).
85. Rasnick, D. & Duesberg, P. H. How aneuploidy affects metabolic control and causes cancer Biochem J 340, 621-630 (1999)
86. Rizvi, A. Z., Swain, J. R., Davies, P. S., Bailey, A. S., Decker, A. D., Willenbring, H., Grompe, M., Fleming, W. H. & Wong, M. H. Bone marrow-derived cells fuse with normal and transformed intestinal stem cells. Proc Natl Acad Sci USA 103(16), 6321-6325 (2006).
87. Rubin, H. Ordered heterogeneity and its decline in cancer and aging. Adv Cancer Res 98, 117-147 (2007)
88. Rubin, H. What keeps cells in tissues behaving normally in the face of myriad mutations?Bioessays 28(5), 515-524 (2006).
89. Rubin, H. Cell-cell contact interactions conditionally determine suppression and selection of the neoplastic phenotype. Proc Natl Acad Sci USA 105(17), 6215-6221 (2008).
90. Sachs, R. K., Levy, D., Hahnfeldt, P. & Hlatky, L. Quantitative analysis of radiation-induced chromosome aberrations. Cytogenet Genome Res 104(1-4), 142-148 (2004)
91. Sackstein, R., Merzaban, J. S., Cain, D. W., Dagia, N. M., Spencer, J. A., Lin, C. P. & Wohlgemuth, R. Ex vivo glycan engineering of CD44 programs human multipotent mesenchymal stromal cell trafficking to bone. Nature Med. 14(2), 181-187 (2008).
92. Salgia, R. & Skarin, A. T. Molecular abnormalities in lung cancer. J Clin Oncol. 16(3), 1207-1217 (1998).
93. Senger, D. R., Perruzzi, C. A., Feder, J. & Dvorak, H. F. A highly conserved vascular permeability factor secreted by a variety of human and rodent tumor cell lines. Cancer Res. 46(11), 5629-5632 (1986)
94. Sithanandam, G. & Anderson, L. M. The ERBB3 receptor in cancer and cancer gene therapy. Cancer Gene Ther., Apr. 11, 2008 [Epub ahead of print]
95. Stampfer, M. R. & Yaswen, P. Human epithelial cell immortalization as a step in carcinogenesis. Cancer Lett. 194, 199-208 (2003).
96. Sterling, H., Saginario, C. & Vignery, A. CD44 occupancy prevents macrophage multinucleation. J. Cell Biol. 143, 837-847 (1998)
97. Stoler, D. L., Chen, N., Basik, M., Kahlenberg, M. S., Rodriguez-Bigas, M. A., Petrelli, N. J. & Anderson, G. R. The onset and extent of genomic instability in sporadic colorectal tumor progression. Proc Natl Acad Sci USA 96(26), 15121-15126 (1999)
98. Stolzing, A., Hescheler, J. & Sethe, S. Fusion and regenerative therapies: is immortality really recessive? Rejuvenation Res. 10(4), 571-586 (2007).
99. Terada, N., Hamazaki, T., Oka, M., Hoki, M., Mastalerz, D. M., Nakano, Y., Meyer, E. M., Morel, L., Petersen, B. E. & Scott, E. W. Bone marrow cells adopt the phenotype of other cells by spontaneous cell fusion. Nature 416(6880), 542-545 (2002).
100. Thompson, S. L. & Compton, D. A. Examining the link between chromosomal instability and aneuploidy in human cells. J. Cell Biol. 180(4), 665-672 (2008)
101. Trimboli, A. J., Fukino, K., de Bruin, A., Wei, G., Shen, L., Tanner, S. M., Creasap, N., Rosol, T. J., Robinson, M. L., Eng, C., Ostrowski, M. C. & Leone, G. Direct evidence for epithelial-mesenchymal transitions in breast cancer. Cancer Res. 68(3), 937-945 (2008).
102. Vignery, A. Macrophage fusion: the making of osteoclasts and giant cells. J Exp Med 202, 337-340 (2005)
103. Vogelstein, B. & Kinzler, K. W. Cancer genes and the pathways they control. Nature Med 10(8), 789-799 (2004)
104. Wai, P. Y., Mi, Z., Gao, C., Guo, H., Marroquin, C. & Kuo, P. C. Ets-1 and runx2 regulate transcription of a metastatic gene, osteopontin, in murine colorectal cancer cells. J Biol. Chem. 281(28), 18973-18982 (2006).
105. Wang, F., Weaver, V. M., Petersen, O. W., Larabell, C. A., Dedhar, S., Briand, P., Lupu, R. & Bissell, M. J. Reciprocal interactions between beta1-integrin and epidermal growth factor receptor in three-dimensional basement membrane breast cultures: a different perspective in epithelial biology. Proc Natl Acad Sci USA 95(25), 14821-14826 (1998).

106. Wong, D. J., Liu, H., Ridky, T. W., Cassarino, D., Segal, E. & Chang, H. Y. Module map of stem cell genes guides creation of epithelial cancer stem cells. Cell Stem Cell 2, 333-344 (2008).

107. Harris, H., Wiener, F. & Klein G. The analysis of malignancy by cell fusion. 3. Hybrids between diploid fibroblasts and other tumour cells. J Cell Sci. 8(3), 681-92 (1971).

108. Wood, L. D., Parsons, D. W., Jones, S., Lin, J., Sjöblom, T., Leary, R. J., Shen, D., Boca, S. M., Barber, T., Ptak, J., Silliman, N., Szabo, S., Derso, Z., Ustyanksky, V., Nikolskaya, T., Nikolsky, Y., Karchin, R., Wilson, P. A., Kaminker, J. S., Zhang, Z., Croshaw, R., Willis, J., Dawson, D., Shipitsin, M., Willson, J. K., Sukumar, S., Polyak, K., Park, B. H., Pethiyagoda, C. L., Pant, P. V., Ballinger, D. G., Sparks, A. B., Hartigan, J., Smith, D. R., Suh, E., Papadopoulos, N., Buckhaults, P., Markowitz, S. D., Parmigiani, G., Kinzler, K. W., Velculescu, V. E., Vogelstein, B. The genomic landscapes of human breast and colorectal cancers. Science 318(5853), 1108-1113 (2007).

109. Yaswen, P. & Stampfer, M. R. Molecular changes accompanying senescence and immortalization of cultured human mammary epithelial cells. Int J Biochem Cell Biol. 34(11), 1382-1394 (2002).

110. Zink, D., Fischer, A. H. & Nickerson, J. A. Nuclear structure in cancer cells. Nature Rev Cancer 4(9), 677-687 (2004).

111. The Scientist 2004, 18(16):38; Published 30 Aug. 2004

112. U.S. Pat. No. 6,004,528

113. U.S. Pat. No. 6,984,522

114. U.S. Pat. No. 7,115,360

115. Jacobsen, B. M., Harrell, J. C., Jedlicka, P., Borges, V. F., Varella-Garcia, M. & Horwitz, K. B. Spontaneous fusion with, and transformation of mouse stroma by, malignant human breast cancer epithelium. Cancer Res. 66(16), 8274-8279 (2006).

116. Harris, H., Wiener, F. & Klein G. The analysis of malignancy by cell fusion. 3. Hybrids between diploid fibroblasts and other tumour cells. J Cell Sci. 8(3), 681-692 (1971).

117. Kerbel, R. S., Lagarde, A. E., Dennis, J. W. & Donaghue, T. P. Spontaneous fusion in vivo between normal host and tumor cells: possible contribution to tumor progression and metastasis studied with a lectin-resistant mutant tumor. Mol Cell Biol. 3(4), 523-538 (1983).

118. Nelson, W. G., De Marzo, A. M. & Isaacs, W. B. Prostate cancer. N Engl J. Med. 349(4), 366-381 (2003).

119. Bubendorf, L., Schöpfer, A., Wagner, U., Sauter, G., Moch, H., Willi, N., Gasser, T. C. & Mihatsch, M. J. Metastatic patterns of prostate cancer: an autopsy study of 1,589 patients. Hum Pathol. 31(5), 578-583 (2000).

120. Denti, F., Wisard, M., Guillou, L., Francke, M. L. & Leisinger, H. J. Renal metastasis from prostatic adenocarcinoma: a potential diagnostic pitfall. Urol Int. 62(3), 171-173 (1999).

121. Carter, H. B., Ferrucci, L., Kettermann, A., Landis, P., Wright, E. J., Epstein, J. I., Trock, B. J. & Metter, E. J. Detection of life-threatening prostate cancer with prostate-specific antigen velocity during a window of curability. J Natl Cancer Inst. 98(21), 1521-1527 (2006).

122. Mayo, J. G. Biologic characterization of the subcutaneously implanted Lewis lung tumor. Cancer Chemother Rep 2 3(1), 325-30 (1972).

123. Gopalakrishnan, G., Danelon, C., Izewska, P., Prummer, M., Bolinger, P. Y., Geissbühler, I., Demurtas, D., Dubochet, J. & Vogel, H. Multifunctional lipid/quantum dot hybrid nanocontainers for controlled targeting of live cells. Angew Chem Int Ed Engl. 45(33), 5478-5483 (2006).

124. Podbilewicz, B. Cell fusion. WormBook. January 6, 1-32 (2006).

125. Orien-Suissa, M. & Podbilewicz, B. Cell fusion during development. Trends Cell Biol. 17(11), 537-546 (2007).

126. Chow, M., Yao, A. & Rubin, H. Cellular epigenetics: topochronology of progressive "spontaneous" transformation of cells under growth constraint. Proc Natl Acad Sci USA 91(2), 599-603 (1994).

127. Evan, G. I., Christophorou, M., Lawlor, E. A., Ringshausen, I., Prescott, J., Dansen, T., Finch, A., Martins, C. & Murphy, D. Oncogene-dependent tumor suppression: using the dark side of the force for cancer therapy. Cold Spring Harb Symp Quant Biol. 70, 263-273 (2005).

128. Coffey, D. S, Nuclear matrix proteins as proteomic markers of preneoplastic and cancer lesions. Clin Cancer Res. 8, 3031-3033 (2002).

129. Rustom, A., Saffrich, R., Markovic, I., Walther, P. & Gerdes, H. H. Nanotubular highways for intercellular organelle transport. Science 303(5660), 1007-10 (2004).

130. Gerdes, H. H. & Carvalho, R. N. Intercellular transfer mediated by tunneling nanotubes. Curr Opin Cell Biol. 20(4), 470-5 (2008).

131. Parangi, S., Dietrich, W., Chistofori, G., Lander, E. S., & Hanahan, D. Tumor suppressor loci on mouse chromosome 9 and 16 are lost at distinct stages of tumorigenesis in a transgenic model of islet cell carcinoma. Cancer Res. 55(24), 6071-6076 (1995).

132. Illmensee, K & Mintz, B. Totipotency and normal differentiation of single teratocarcinoma cells cloned by injection into blastocysts. Proc Natl Acad Sci USA 73(2), 549-53 (1976).

133. Radisky, D. C. & Bissell, M. J. Cancer. Respect thy neighbor! Science 303(5659), 775-7 (2004).

134. Bergsmedh, A., Szeles, A., Henriksson, M., Bratt, A., Folkman, M. J., Spetz, A. L. & Holmgren, L. Horizontal transfer of oncogenes by uptake of apoptotic bodies. Proc Natl Acad Sci USA 98(11), 6407-11 (2001).

135. Zhao, J. J., Gjoerup, O. V., Subramanian, R. R., Cheng, Y., Chen, W., Roberts, T. M. & Hahn, W. C. Human mammary epithelial cell transformation through the activation of phosphatidylinositol 3-kinase. Cancer Cell 3(5), 483-95 (2003).

136. Ince, T. A., Richardson, A. L., Bell, G. W., Saitoh, M., Godar, S., Karnoub, A. E., Iglehart, J. D. & Weinberg, R. A. Transformation of different human breast epithelial cell types leads to distinct tumor phenotypes. Cancer Cell 12(2), 160-70 (2007).

137. Jiang, Y., Jahagirdar, B. N., Reinhardt, R. L., Schwartz, R. E., Keene, C. D., Ortiz-Gonzalez, X. R., Reyes, M., Lenvik, T., Lund, T., Blackstad, M., Du, J., Aldrich, S., Lisberg, A., Low, W. C., Largaespada, D. A. & Verfullie, C. M. Pluripotency of mesenchymal stem cells derived from adult marrow. Nature 418, 41-9 (2002).

138. Krause, D. S., Theise, N. D., Collector, M. I., Henegariu, O., Hwang, S., Gardner, R., Neutzel, S. & Sharkis, S. J. Multi-organ, multi-lineage engraftment by a single bone marrow-derived stem cell. Cell 105(3), 369-77 (2001).

What is claimed is:

1. An isolated self-renewing cell selected as the product of a spontaneous cell-cell fusion or a descendant thereof, wherein the spontaneous fusion is between a non-neoplastic cell and a non-neoplastic cell of the same cell type, wherein said cell is aneuploid, has periodically increased expression of an oncogene selected from the group consisting of VEGF, MMP-9, k-ras, myc and Bcl-2 relative to a reference cell, and has periodically reduced expression of CDKn2A, p53, and CD44 relative to a reference cell.

2. A tumor-initiating cell selected as the product of a spontaneous cell-cell fusion or a descendant thereof, wherein said cell gives rise to a neoplasia in vitro or in vivo under suitable growth conditions, wherein the spontaneous fusion is between a non-neoplastic cell and a non-neoplastic cell of the same cell type, wherein said cell is aneuploid, has periodically increased expression of an oncogene selected from the group consisting of VEGF, MMP-9, k-ras, myc and Bcl-2 relative to a reference cell, and has periodically reduced expression of CDKn2A, p53, and CD44 relative to a reference cell.

3. The cell of claim 1 or 2, wherein said cell exhibits a characteristic selected from the group consisting of:
   increased cellular proliferation rate relative to a corresponding reference cell,
   formation of a colony in soft agar in vitro, and
   formation of a tumor in vivo.

4. The cell of claim 1 or 2, wherein the cell is selected using two distinct detectable labels.

5. An isolated cell population comprising cells selected as the product of a spontaneous cell-cell fusion or descendants thereof, and cultured under conditions sufficient to promote further fusion, wherein at least one cell of said population is a self-renewing tumor-initiating cell, wherein the spontaneous fusion is between a non-neoplastic cell and a non-neoplastic cell of the same cell type, wherein said cell is aneuploid, has periodically increased expression of an oncogene selected from the group consisting of VEGF, MMP-9, k-ras, myc and Bcl-2 relative to a reference cell, and has periodically reduced expression of CDKn2A, p53, and CD44 relative to a reference cell.

6. The isolated cell population of claim 5, wherein at least about 50-75% of said population are tumor-initiating cells or highly tumorogenic cells.

7. The isolated cell population of claim 5, wherein said cell population exhibits a characteristic selected from the group consisting of:
   increased cellular proliferation rate relative to a corresponding reference cell,
   able to form a colony in soft agar in vitro, and
   able to form a tumor in vivo.

8. The isolated cell population of claim 5, wherein at least about 50% of said cells are aneuploid and show increased expression of an oncogene selected from the group consisting of k-ras, myc and Bcl-2, and show decreased expression of CDKn2A and p53 relative to a corresponding reference cell.

9. The isolated cell population of claim 5, wherein the population has a tumor producing efficiency that is at least about 10-fold greater than a reference cell.

10. The isolated cell population of claim 5, wherein injection of at least about 10-500 cells of said population forms a tumor of about 1 cm diameter in at least about 50% of nude mice within about 2-6 weeks.

11. The isolated cell population of claim 5, wherein at least about 50% of the cells in the population exhibit synchronous differential expression of at least two markers selected from the group consisting of Myc, K-ras, Bcl-2, p53, CDKn2a, CD44, SPP1, and VEGF relative to a corresponding reference population.

12. The isolated cell population of claim 5, wherein one of the non-neoplastic cells is a fibroblast or epithelial cell.

13. The isolated cell population of claim 5, wherein the cell-cell fusion does not give rise to a macrophage, muscle cell, hybridoma cell, or virus infected cell.

14. The isolated cell population of claim 5, wherein the cell is derived from a subject identified as having or having a propensity to develop a neoplasia.

15. The isolated cell population of claim 14, wherein the neoplasia is a solid tumor or blood tumor.

16. The isolated cell population of claim 5, wherein conditions sufficient to promote further fusion include culturing the cells at a density of about 80% confluence.

17. A method of generating the tumor-initiating cell of claim 2, comprising selecting a cell that is the product of a spontaneous cell-cell fusion or a descendant thereof and culturing said cells, thereby generating a tumor-initiating cell population, wherein the spontaneous fusion is between a non-neoplastic cell and a non-neoplastic cell, and wherein the selected cell is aneuploid, has periodically increased expression of an oncogene selected from the group consisting of VEGF, MMP-9, k-ras, myc and Bcl-2 relative to a reference cell, and has periodically reduced expression of CDKn2A, p53, and CD44 relative to a reference cell.

18. The method of claim 17, further comprising culturing said cells under conditions sufficient to promote further fusion.

19. The method of claim 17, wherein said cells comprise at least two nuclei.

20. The method of claim 17, wherein the method further comprises selecting a cell comprising at least 3 or 4 nuclei, and allowing said cell to proliferate.

21. The method of claim 17, wherein the cell that is a product of the spontaneous cell-cell fusion is identified using detectable cellular markers.

22. The method of claim 21, where said detectable cellular markers are cytoplasmic vital dyes.

23. The method of claim 17, wherein at least one of the cells that undergoes spontaneous cell-cell fusion is derived from a subject identified as having or having a propensity to develop a neoplasia.

24. An isolated tumor-initiating cell made by the process of claim 17.

25. The isolated cell of claim 24, wherein the cell or cell population is self-renewing, capable of forming a tumor when injected into a SCID mouse, a nude mouse, an immune competent mouse, or is resistant to exposure to radiation or chemotherapy.

26. The isolated cell of claim 24 or 25, wherein said cell exhibits a characteristic selected from the group consisting of:
  genomic instability,
  increased cellular proliferation rate relative to a corresponding reference cell,
  able to form a colony in soft agar in vitro, and
  able to form a tumor in vivo.

27. The isolated cell of claim 24 or 25, wherein said cell is aneuploid, has increased expression of k-ras, myc and Bcl-2, and has reduced expression of CDKn2A and p53 relative to a control cell.

28. The isolated cell of claim 24 or 25, wherein the cell is tumorogenic.

29. The isolated cell of claim 24 or 25, wherein said cell has a tumor producing efficiency that is at least 10-fold greater than a reference cell not the product of a cell-cell fusion event.

30. A composition comprising a population of tumor-initiating cells made by the process of claim 17.

31. The composition of claim 30, wherein injection of at least about 10-500 cells of said population forms a tumor of about 1 cm diameter in at least about 50% of nude mice within about 2-6 weeks.

32. The composition of claim 30 or 31, wherein at least about 50% of the cells in the population exhibit periodic differential expression of at least two markers selected from the group consisting of Myc, K-ras, Bcl-2, p53, CDKn2a, CD44, SPP1, and VEGF relative to a corresponding reference population.

33. A method for identifying an agent for the treatment or prevention of a neoplasia, hyperplasia or a hyperproliferative disorder comprising:
  contacting the tumor-initiating cell or cell population of claim 2 with an agent; and
  detecting a decrease in cell survival or proliferation relative to an untreated control cell or cell population.

34. A method for identifying an agent that inhibits cell-cell fusion comprising:
  contacting the isolated cell of claim 5 with an agent; and
  detecting a reduction in cell-cell fusion relative to an untreated control population.

35. The method of claim 34, wherein a reduction in multinucleate cell number in the treated population identifies an agent that inhibits cell-cell fusion.

36. The method of claim 33 or 34, wherein the agent increases cell death.

37. The method of claim 33 or 34, further comprising maintaining the cell in culture under conditions sufficient to generate mononucleate cells from a multinucleate cell, and identifying a reduction in the generation of said cells relative to a corresponding control culture.

38. The method of claim 34, wherein the cell is a fibroblast or epithelial cell.

39. A method of identifying an agent that prevents neoplasia relapse following chemotherapy, the method comprising:
  contacting the isolated cell population of claim 14 with an agent;
  detecting a decrease in cell survival, proliferation, or fusion relative to an untreated control cell or cell population, wherein said decrease identifies that agent as preventing neoplasia relapse following chemotherapy.

40. An immunogenic composition for the treatment or prevention of a neoplasia in a subject, the composition comprising an effective amount of a cell population of any one of claim 1, 2, or 5, and an excipient, wherein the cell population has been rendered non-viable.

41. The immunogenic composition of claim 40, further comprising an adjuvant.

42. The immunogenic composition of claim 40, wherein said cell population is derived from a subject identified as having or having a propensity to develop a neoplasia.

43. A method for inducing an immune response against a tumor-initiating cell or neoplasia, the method comprising administering the immunogenic composition of claim 40 to a subject.

44. The method of claim 43, wherein the immunogenic composition comprises a cell derived from the subject to be treated.

45. The method of claim 43, wherein the method treats or prevents a neoplasia.

46. The method of claim 43, wherein the method treats or prevents the relapse of a neoplasia.

47. The method of claim 43, wherein the method is administered prior to, concurrent with, or following chemotherapy or radiation therapy.

48. A method of immortalizing a primary cell in culture comprising:
  selecting the isolated self-renewing cell of claim 1 or the tumor-initiating cell of claim 2; and
  culturing the selected cell under conditions that promote further cell-cell fusions, thereby generating an immortalized cell.

49. The method of claim 48, wherein the selected cell is bi or multinucleate.

50. The method of claim 48, further comprising the step of maintaining the bi or multinucleate cells in culture for a time sufficient to generate a population comprising at least 50% mononucleate aneuploid cells.

51. A method for producing a differentiated cell from a tumor-initiating cell, the method comprising providing a cell according to claim 1 or 2, and contacting the cell with a differentiation agent, thereby producing a differentiated cell.

* * * * *